US009925173B2

(12) United States Patent
Blight et al.

(10) Patent No.: US 9,925,173 B2
(45) Date of Patent: *Mar. 27, 2018

(54) METHODS OF USING SUSTAINED RELEASE AMINOPYRIDINE COMPOSITIONS

(71) Applicant: Acorda Therapeutics, Inc., Ardsley, NY (US)

(72) Inventors: Andrew R. Blight, Mahopac, NY (US); Ron Cohen, Irvington, NY (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/482,426

(22) Filed: Apr. 7, 2017

(65) Prior Publication Data

US 2017/0209422 A1    Jul. 27, 2017

Related U.S. Application Data

(63) Continuation of application No. 15/344,096, filed on Nov. 4, 2016, which is a continuation of application (Continued)

(51) Int. Cl.
 *A61K 31/4409*    (2006.01)
(52) U.S. Cl.
 CPC ............................... *A61K 31/4409* (2013.01)
(58) Field of Classification Search
 CPC ....... A61K 31/44; A61K 31/4409; A61K 9/20
 See application file for complete search history.

(56) References Cited

U.S. PATENT DOCUMENTS

| 3,065,143 A | 11/1962 | Christenson et al. |
| 3,459,850 A | 8/1969 | Riva |

(Continued)

FOREIGN PATENT DOCUMENTS

| CA | 2085785 | 6/1994 |
| EP | 0 156 077 B1 | 5/1984 |

(Continued)

OTHER PUBLICATIONS

Defendants' Second Amended Joint Invalidity Contentions Pursuant to The Default Standard for Discovery, filed Jan. 8, 2016 in *Acorda Therapeutics, Inc.* v. *Alkem Laboratories, Ltd., et al.*, C.A. No. 1:14-cv-00882-LPS (Consolidated) (Redacted).

(Continued)

*Primary Examiner* — Savitha M Rao
(74) *Attorney, Agent, or Firm* — Jones Day

(57) ABSTRACT

A pharmaceutical composition which comprises a therapeutically effective amount of a aminopyridine dispersed in a release matrix, including, for example, a composition that can be formulated into a stable, sustained-release oral dosage formulation, such as a tablet which provides, upon administration to a patient, a therapeutically effective plasma level of the aminopyridine for a period of at about 12 hours and the use of the composition to treat various neurological diseases, including multiple sclerosis. A method of selecting individuals based on responsiveness to a treatment, including, for example, identifying individuals who responded to treatment with a sustained release fampridine composition.

29 Claims, 12 Drawing Sheets

Related U.S. Application Data

No. 15/079,010, filed on Mar. 23, 2016, now abandoned, which is a continuation of application No. 14/531,191, filed on Nov. 3, 2014, now abandoned, which is a continuation of application No. 13/829,221, filed on Mar. 14, 2013, now abandoned, which is a continuation of application No. 13/410,388, filed on Mar. 2, 2012, now abandoned, which is a continuation of application No. 11/102,559, filed on Apr. 8, 2005, now Pat. No. 8,354,437.

(60) Provisional application No. 60/560,894, filed on Apr. 9, 2004.

(56) References Cited

U.S. PATENT DOCUMENTS

| | | |
|---|---|---|
| 3,538,214 A | 11/1970 | Polli et al. |
| 4,386,095 A | 5/1983 | Gibson et al. |
| 4,508,715 A | 4/1985 | Booth et al. |
| 4,562,196 A | 12/1985 | Horn et al. |
| 4,695,467 A | 9/1987 | Uemura et al. |
| 4,716,040 A | 12/1987 | Panoz |
| 4,721,619 A | 1/1988 | Panoz et al. |
| 4,760,092 A | 7/1988 | Weinreb |
| 4,812,447 A | 3/1989 | Roberts |
| 4,832,957 A | 5/1989 | Demski et al. |
| 4,851,230 A | 7/1989 | Tencza et al. |
| 4,894,240 A | 1/1990 | Geoghegan et al. |
| 4,946,853 A | 8/1990 | Banon et al. |
| 4,948,581 A | 8/1990 | Sawayanagi et al. |
| 5,370,879 A | 12/1994 | Masterson et al. |
| 5,451,409 A | 9/1995 | Rencher et al. |
| 5,540,938 A | 7/1996 | Masterson et al. |
| 5,545,648 A | 8/1996 | Hansebout et al. |
| 5,580,580 A | 12/1996 | Masterson et al. |
| 5,597,827 A | 1/1997 | Miller et al. |
| 5,597,828 A | 1/1997 | Miller et al. |
| 5,849,240 A | 12/1998 | Miller et al. |
| 5,869,480 A | 2/1999 | Shutske et al. |
| 5,952,357 A | 9/1999 | Bliss et al. |
| 6,284,473 B1 | 9/2001 | Whitaker |
| 6,288,026 B1 | 9/2001 | Exner et al. |
| 7,179,486 B1 | 2/2007 | Mulye |
| 8,007,826 B2 | 8/2011 | Blight et al. |
| 8,354,437 B2 | 1/2013 | Blight et al. |
| 8,440,703 B2 | 5/2013 | Blight et al. |
| 8,663,685 B2 | 3/2014 | Blight et al. |
| 2005/0025744 A1 | 2/2005 | Lane |
| 2006/0276537 A1 | 12/2006 | Goren et al. |
| 2007/0037848 A1 | 2/2007 | Masters et al. |
| 2009/0150180 A1 | 6/2009 | Cohen et al. |
| 2010/0061935 A1 | 3/2010 | Blight et al. |
| 2010/0272795 A1 | 10/2010 | Cunningham |
| 2010/0272796 A1 | 10/2010 | Cunningham |
| 2010/0272807 A1 | 10/2010 | Cunningham |
| 2010/0324098 A1 | 12/2010 | Blight et al. |
| 2010/0324099 A1 | 12/2010 | Blight et al. |
| 2010/0324100 A1 | 12/2010 | Blight et al. |
| 2011/0166187 A1 | 7/2011 | Blight et al. |
| 2011/0166188 A1 | 7/2011 | Blight et al. |
| 2011/0166189 A1 | 7/2011 | Blight et al. |
| 2012/0029035 A1 | 2/2012 | Blight et al. |
| 2012/0041034 A1 | 2/2012 | Blight et al. |
| 2012/0164078 A1 | 6/2012 | Blight et al. |
| 2013/0045276 A1 | 2/2013 | Cunningham et al. |
| 2013/0267566 A1 | 10/2013 | Blight et al. |
| 2013/0310426 A1 | 11/2013 | Blight et al. |
| 2014/0018397 A1 | 1/2014 | Cunningham et al. |
| 2014/0039015 A1 | 2/2014 | Blight et al. |
| 2014/0206728 A1 | 7/2014 | Blight et al. |
| 2015/0080436 A1 | 3/2015 | Blight et al. |
| 2015/0313886 A1 | 11/2015 | Blight et al. |
| 2016/0081992 A1 | 3/2016 | Cunningham et al. |
| 2016/0175294 A1 | 6/2016 | Cunningham et al. |
| 2016/0199358 A1 | 7/2016 | Blight et al. |
| 2016/0324840 A1 | 11/2016 | Cunningham et al. |
| 2017/0027874 A1 | 2/2017 | Cunningham et al. |
| 2017/0056385 A1 | 3/2017 | Wessel et al. |
| 2017/0071924 A1 | 3/2017 | Blight et al. |

FOREIGN PATENT DOCUMENTS

| | | |
|---|---|---|
| EP | 0 113 562 B1 | 7/1984 |
| EP | 0 117 027 A1 | 8/1984 |
| EP | 0 325 843 A2 | 8/1989 |
| EP | 0 484 186 A1 | 5/1992 |
| EP | 2 377 536 A1 | 10/2011 |
| IE | 82916 B1 | 6/2003 |
| WO | WO 2004/082684 A1 | 9/2004 |
| WO | WO 2005/099701 A2 | 10/2005 |
| WO | WO 2007/035958 A2 | 3/2007 |
| WO | WO 2010/030755 A1 | 3/2010 |
| WO | WO 2010/093838 A1 | 8/2010 |
| WO | WO 2010/093839 A1 | 8/2010 |
| WO | WO 2010/090730 A1 | 9/2010 |
| WO | WO 2011/019845 A1 | 3/2011 |
| WO | WO 2011/029082 A1 | 3/2011 |

OTHER PUBLICATIONS

Opening Expert Report of Dr. Arthur H. Kibbe, filed Mar. 4, 2016 in *Acorda Therapeutics, Inc. v. Alkem Laboratories, Ltd. et al.*, C.A. No. 14-00882-LPS (Consolidated) (Redacted).

Opening Expert Report of Dr. Stephen J. Peroutka, filed Mar. 4, 2016 in *Acorda Therapeutics, Inc. v. Alkem Laboratories, Ltd. et al.*, C.A. No. 14-00882-LPS (Consolidated) (Redacted).

Reply Expert Report of Dr. Stephen J. Peroutka, filed May 20, 2016 in *Acorda Therapeutics, Inc. v. Alkem Laboratories, Ltd. et al.*, C.A. No. 14-00882-LPS (Consolidated) (Redacted).

Report of DeForest McDuff, Ph.D., filed May 20, 2016 in *Acorda Therapeutics, Inc. v. Alkem Laboratories, Ltd. et al.*, C.A. No. 14-00882-LPS (Consolidated) (Redacted).

U.S. Appl. No. 14/925,946, filed Oct. 28, 2015, Blight et al.

U.S. Appl. No. 14/925,950, filed Oct. 28, 2015, Blight et al.

U.S. Appl. No. 15/178,567 with Preliminary Amendment filed Jun. 9, 2016, filed Jun. 9, 2016, Blight et al.

U.S. Appl. No. 15/482,412 with Preliminary Amendment filed Apr. 25, 2017, filed Apr. 7, 2017, Blight et al.

U.S. Appl. No. 15/482,432 with Preliminary Amendment filed Apr. 25, 2017, filed Apr. 7, 2017, Blight et al.

U.S. Appl. No. 15/386,928, filed Dec. 21, 2016, Blight et al.

U.S. Appl. No. 15/386,982, filed Dec. 21, 2016, Blight et al.

U.S. Appl. No. 15/418,117 with Preliminary Amendment filed Jan. 27, 2017, filed Jan. 27, 2017, Blight et al.

U.S. Appl. No. 15/431,513, filed Feb. 13, 2017, Pardo et al.

U.S. Appl. No. 15/442,017, filed Feb. 24, 2017, Cunningham et al.

U.S. Appl. No. 15/441,706, filed Feb. 24, 2017, Wessel et al.

"Acorda chooses spasticity as fampridine lead indication," ProusScienceDailyEssentials, Jan. 17, 2002.

"Biotechnology Analysis: Ron Cohen—Acorda Therapeutics Inc | Round Table |," Interview, Wall Street Transcript, Oct. 14, 2002 (https://www.twst.com/interview/13880, last accessed Jun. 27, 2014).

"Fampridine-SR enters two phase III trials for chronic spinal cord injury," ProusScienceDailyEssentials, Jul. 3, 2002.

2nd Meeting of the Pharmacy Compounding Advisory Committee, May 6, 1999, Transcript (http://www.fda.gov/ohrms/dockets/ac/99/transcpt/3513t1.rtf (last accessed Nov. 18, 2010)).

Advisory Action Before the Filing of an Appeal Brief dated Aug. 20, 2014 for U.S. Appl. No. 12/626,085, filed Nov. 25, 2009.

Advisory Action Before the Filing of an Appeal Brief dated Mar. 13, 2009 for U.S. Appl. No. 11/102,559, filed Apr. 8, 2005.

Agoston et al., 1978, "Effects if 4-Aminopyridine in Eaton Lambert Syndrome," Br. J. Anesth., 50:383-385.

Agoston et al.,1980, "Antagonism of Ketamine-Diazepam anaesthesia by 4-Aminopyridine in Human Volunteers," Br. J. Anaesth., 52:367-369.

(56) References Cited

OTHER PUBLICATIONS

Aisen et al., 1995, "3,4-Diaminopyridine as a treatment for amyotrophic lateral sclerosis," J. of Neurological Sciences, 129:21-24.
Aisen et al., 1996, "A double-blind placebo-controlled study of 3,4-diaminopyridine in amytrophic lateral sclerosis patients on a rehabilitation unit," J. of Neurological Sciences, 138:93-96.
Albrecht et al., 2001, "Day-to-day variability of maximum walking distance in MS patients can mislead to relevant changes in the Expanded Disability Status Scale (EDSS): average walking speed is a more constant parameter," Multiple Sclerosis, 7:105-109.
Amendment filed Jul. 24, 1995 in U.S. Appl. No. 08/328,165, filed Oct. 24, 1994.
Amendment filed Sep. 3, 1992 in U.S. Appl. No. 7/786,400, filed Nov. 1, 1991.
AMPYRA® (dalfampridine), Acorda Therapeutics, Inc., Prescribing Information, Jan. 2010. http://ampyra.com/local/files/PI.pdf (last accessed Nov. 3, 2010).
Andreasen, 2002, "Inhibition of slow $Ca^{2+}$-activated $K^+$ current by 4-aminopyridine in rat hippocampal CA1 pyramidal neurones," British Journal of Pharmacology 135:1013-1025.
Ansel et al., 1995, "Pharmaceutical Dosage Forms and Drug Delivery Systems," 6th Edition, Williams & Wilkins, pp. 213-221.
Arhem et al., 1989, "A model for the fast 4-aminopyridine effects on amphibian myelinated nerve fibers. A study based on voltage-clamp experiments," Acta Physiol. Scan., 137:53-61.
Ashworth et al., 1964, "Preliminary Trial of Carisoprodol in Multiple Sclerosis," Practitioner, 192:540-542.
Aulton (Ed.), 2002, "Pharmaceutics—The Science of Dosage Form Design," Second Edition, Churchill Livingstone, New York, Chapter 19:275-288.
AVONEX® (interferon beta-1a), Biogen Idec Inc., Prescribing Information, Oct. 2008. http://www.avonex.com/pdfs/pi_luer_lock.pdf (last accessed Nov. 3, 2010).
Ball et al., 1979, "Human botulism caused by Clostridium Botulinum Type E: the Birmingham Outbreak," Quarterly Journal of Med. New Series XLVIII, 191:473-491.
Barker et al., 1991, "Alzheimer's disease," Pharmaceutical Journal, Jan. 26, 1991, pp. 116-118.
Berge et al., 1977, "Pharmaceutical Salts," J. Pharm. Sci., 66(1):1-19.
Beric et al., 1988, "Central dysesthesia syndrome in spinal cord injury patients," Pain, 34:109-116.
Beric, 1990, "Altered sensation and pain in spinal cord injury," Recent Achievements in Restorative Neurology, 3 Altered Sensation and Pain, Dimitrijevic et al., eds., Karger:Basel, pp. 27-36.
Bertelsmann et al., 1992, "Comparison between 4-aminopyridine and 3,4diaminopyridine in the treatment of multiple sclerosis," Annals of Neurology, 32(2):256 (Abstract P100).
BETASERON® (Interferon Beta-1b) for SC injection, Bayer HealthCare Pharmaceuticals Inc., Prescribing Information, May 2010. http://berlex.bayerhealthcare.com/html/products/pi/Betaseron_PI.pdf (last accessed Nov. 3, 2010) (pp. 1-10).
Bever et al., 1990, "Preliminary trial of 3, 4-diaminopyridine in patients with multiple sclerosis," Annals of Neurology, 27(4):421-427.
Bever et al., 1994, "The effects of 4-aminopyridine in multiple sclerosis patients: Results of a randomized, placebo-controlled, double-blind, concentration-controlled, crossover trial," Neurol., 44(6):1054-1059.
Bever et al., 1995, "Experience with slow release 4-aminopyridine in multiple sclerosis patients: Long term tolerability and safety," Journal of Neuroimmunology, 1 Suppl. 58.
Bever et al., 1995, "The brief repeatable battery of neuropsychological tests for multiple sclerosis: a preliminary serial study," Multiple Sclerosis, 1:165-169.
Bever et al., 1995, "The Pharmacokinetics and Tolerability of a Slow-Release Formulation of 4-Aminopyridine in Multiple Sclerosis Patients," Neurol., 45(Suppl 4):A351 (Abst. 684P).
Bever et al., 1996, "Treatment with oral 3,4 diaminopyridine improves leg strength in multiple sclerosis patients: Results of a randomized, double-blind, placebo-controlled, crossover trial," Neurol., 47:1457-1462.
Bever et al., 2009, "Sustained-release fampridine for multiple sclerosis," Expert Opin. Investig. Drugs, 18(7):1013-1024.
Bever, 1994, "The Current Status of Studies of Aminopyridines in Patients with Multiple Sclerosis," Ann Neurol, 36: S118-S121.
Biessels et al., 1984, "Comparison of the pharmacological actions of some new 4-aminopyridine derivatives," European J. of Pharmacology, 106:319-325.
Blight et al., 1983, "Axonal physiology of chronic spinal cord injury in the cat: Intracellular recording in vitro," Neuroscience, 10(4):1471-1486.
Blight et al., 1986, "Morphometric analysis of spinal cord injury in the cat: The relation of injury intensity of survival of myelinated axons," Neuroscience, 19(1):321-341.
Blight et al., 1987, "Augmentation by 4-aminopyridine of vestibulospinal free fall responses in chronic spinal-injured cats," J. of the Neurological Sciences, 82(1-3):145-159.
Blight et al., 1991, "The effects of 4-aminopyridine on neurological deficits in chronic cases of traumatic spinal cord injury in dogs: a phase I clinical trial," J. Neurotrauma, 8:103-119.
Blight et al., 2001, "Acute spinal cord injury: Pharmacotherapy and drug development perspectives," Curr. Opin. Investig. Drugs, 2(6):801-08.
Blight, 1983, "Cellular morphology of chronic spinal cord injury in the cat: analysis of myelinated axons by line-sampling," Neuroscience, 10(2):521-543.
Blight, 1987, "Effect of 4-aminopyridine on action potential conduction in myelinated axons of chronically injured spinal cord," Society of Neurosciences Abstracts, 13(1):62 (Abstract 21.15).
Blight, 1989, "Effect of 4-aminopyridine on axonal conduction-block in chronic spinal cord injury," Brain Res. Bull., 22(1):47-52.
Blight, 1991, "Morphometric analysis of a model of spinal cord injury in guinea pigs, with behavioral evidence of delayed secondary pathology," J. Neurol. Sci., 103(2):156-71.
Blight, 1991, "Morphometric analysis of blood-vessels in chronic experimental spinal-cord injury: hypervascularity and recovery of function," J of Neurol Sci., 106(2):158-174.
Blight, 1998, "Containing plasticity: neurite inhibitory factors of myelin," Nat. Neurosci., 1(2):87-88.
Blight, 2002, "Miracles and molecules—progress in spinal cord repair," Nature Neuroscience, 5:1051-1054.
Blight, 2004,"Just one word: plasticity," Nat. Neurosci., 7(3):206-08.
Booij et al., 1978, "Neostigmine and 4-Aminopyridine Antagonism of Lincomycin-Pancuronium Neuromuscular Blockade in Man," Anesth. Analg., 57:316-321.
Bostock et al., 1981, "The effects of 4-aminopyridine and tetraethylammonium ions on normal and demyelinated mammalian nerve fibres," J. Physiol., 313:301-15.
Bowe et al., 1987, "Physiological effects of 4-aminopyridine on demyelinated mammalian motor and sensory fibers," Ann. Neurol., 22(2):264-8.
Bowman et al., 1981, "Actions of 4-aminopyridine on the cardiovascular systems of anaesthetized cats and dogs," Br. J. Anaesth., 53:555-565.
Bowman et al., 1981, "Pharmacological actions of aminopyridines and related compounds," Rev. Pure Appl. Phamacol. Sci., 2(4):317-371.
Bresnahan et al., 1987, "A behavorial and anatomical analysis of spinal cord injury produced by a feedback-controlled impaction device," Exp. Neurol., 95:548-570.
Bronnum-Hansen et al., 2005, "Suicide among Danes with multiple sclerosis," J. of Neurol. Neurosurg. Psych., 76:1457-1459.
Bruckner et al., 2000, "Effects of standard anticonvulsant drugs on different patterns of epileptiform discharges induced by 4-aminopyridine in combined entorhinal cortex-hippocampal slices," Brain Res., 859(1):15-20.
Bugaresti et al., 2001, "Pharmacokinetics and safety of single oral doses of fampridine-SR (sustained-release 4-aminopyridine) tablets in patients with chronic spinal cord injury," Presented to the

(56) References Cited

OTHER PUBLICATIONS

American Academy of Physical Medicine and Rehabilitation, New Orleans, LA, Sep. 13-16, 2001 (Poster).
Burchiel et al., 1985, "Effects of potassium channel-blocking agents on spontaneous discharges from neuromas in rats," J. of Neurosurgery, 63:246-249.
Calabresi et al., 1993, "Progressive spinal multiple sclerosis," Seminars in Neurology, 13(4):322-332.
Capacio et al., 1997, "Pharmacokinetics and pharmacodynamics of 4-aminopyridine in awake guinea pigs," Drug Chem. Toxicol., 20(3):151-172.
Cardenas E et al., 2007, "Phase 2 trial of sustained-release fampridine in chronic spinal cord injury," Spinal Cord, 4592:158-168.
Carlsson et al., 1983, "Can 4-aminopyridine be used to reverse anaesthesia and muscle relaxation?" Acta Anaesth. Scand., 27:87-90.
CD-ROM in duplicate containg video-file "Today Show.mov," created Jul. 18, 2010, showing segment of the "Today Show" aired May 27, 2010 accompained by still image single frame photograph.
Chalk et al., 1990, "Response of the Lambert-Eaton myasthenic syndrome to treatment of associated small-cell lung carcinoma," Neurology, 40(10):1552-1556.
Chandy et al., 1984, "Voltage-gated potassium channels are required for human T-lymphocyte activation," J. Exp. Med., 160:369-385.
Choquet et al., 1988, "Modulation of voltage-dependent potassium channels in B-lymphocytes," Biochem. Pharmacol., 37(20):3797-3802.
Clinicaltrial.gov, Efficacy, safety, and tolerability of Nerispirdine in patients with multiple sclerosis, ClinicalTrials.gov. http://clinicaltrials.gov/show/NCT00811902 (last accessed Nov. 2, 2010).
Coetzee et al., 1999, "Molecular diversity of K+ channels," Ann. NY Acad. Sci., 868:233-285.
Cohen et al., 1999, "Utilization of the multiple sclerosis functional composite as an outcome measure in the phase 3 trial of interferon beta-1a (Avonex®) in secondary progressive multiple sclerosis (Impact)," Neurology, 62 (6 Suppl. 2):A548-S549 (Abstract S74.002).
Cohen et al., 2000, "Intrarater and interrater reliability of the MS functional composite outcome measure," Neurology, 54:802-806.
Cohen et al., 2000, "One-year change in the multiple sclerosis functional composite and expanded disability status scale in the phase 3 trial of interferon beta-1a in secondary progressive multiple sclerosis (Impact)," Neurology, 54 (7 Supp. 3):A215 (Abstract S30.02).
Cohen et al., 2001, "Results of Impact, a phase 3 trial of interferon beta-1a in secondary progressive multiple sclerosis," Neurology, 56 (8 Supp. 3):A148-149 (Abstract S20.003).
Cohen et al., 2001, "Use of the multiple sclerosis functional composite as an outcome measure in a phase 3 clinical trial," Arch. Neurol. 58:961-967.
Cohen et al., 2002, Benefit of interferon beta-1a on MSFC progression in secondary progressing MS (Abstract), Neurology, 59(5):679-687.
Cohen et al., 2004, "The two towers: Quest for drugs from discovery to approval," Top Spinal Cord Inj. Rehabil., 10(1):63-71.
Cohen et al., 2005, "Responder analysis of walking speed applied to a trial of fampridine in subjects with MS," 57th Annual Meeting of the American Academy of Neurology, Miami, FL, Apr. 9-16, 2005 (Poster).
Cohen et al., 2005, "Responder analysis of walking speed applied to a trial of fampridine in subjects with MS," Neurology, 64(Suppl. 1):A388, P06.169.
Compston, 2002, "Multiple sclerosis," Lancet 359:1221-1231.
Confavreux and Compston, 2005, "Disease-modifying treatments in multiple sclerosis," Chap. 18 in McAlpine's Multiple Sclerosis, 4th ed., Compston et al., (eds.), Churchill Livingstone Elsevier, pp. 765-770.
Confavreux and Compston, 2005, "The person with multiple sclerosis: a prospectus," Chap. 19, in McAlpine's Multiple Sclerosis 4th ed., Compston et al. (eds.), Churchill Livingstone Elsevier, pp. 805-810.
Confavreux and Compston, Dec. 2005, "The natural history of multiple sclerosis," Chap. 4 in McAlpine's Multiple Sclerosis, 4th Ed., Compston et al. (eds.) Churchill Livingstone Elsevier, pp. 193-196.
Conrad, 1984, "Innovations in Drug Delivery," Postgrad. Med. 76(5): 71-73, 75-79.
Consortium of Multiple Sclerosis Centers (CMSC), Annual Meeting, Jun. 7, 2002 (Poster).
Cooke et al., 1994, "Lambert-Eaton myasthenic syndrome: evaluation of movement performance following drug therapy," Electromyogr. Clin. Neurophysiol., 34(2):87-93.
Copaxone® (glatiramer acetate), TEVA Neuroscience, Inc., Prescribing Information, Feb. 2009. http://www.copaxone.com/pdf/PrescribingInformation.pdf (last accessed Nov. 3, 2010).
Cowen and Company—Acorda Therapeutics, Nov. 19, 2010 (p. 1-18).
Cowen and Company, "Acorda Therapeutics," Aug. 3, 2010 (pp. 1-5).
Crenshaw et al. 2006, "Gait variability in people with multiple sclerosis," Multiple Sclerosis, 12:613-691.
Darlington, 2000, "Fampridine Acorda Therapeutics," Curr. Opin. Investig. Drugs, 1(3):375-379.
Davidson et al., 1988, "4-Aminopyridine in the treatment of Alzheimer's Disease," Biol. Psychiatry, 23:485-490
Davis et al., 1990, "Orally Administered 4-Aminopyridine Improves Clinical Signs in Multiple Sclerosis," Ann. Neurol., 27:186-192.
Davis et al., 1995, "Mechanism of Action of 4-Aminopyridine in the Symptomatic Treatment of Multiple Sclerosis," Ann. Neurol., 37(5):684.
de Waal et al., 1994, "The treatment of multiple sclerosis (MS): 4-aminopyridine (4-AP)," J. of Neurology, 241:S102 (Abstract 11).
Declaration of Gerrit Voortman dated Dec. 6, 2013 (with Enclosures: Curriculum Vitae of Gerrit Voortman and Marinucci et al., 2007, "The Range Disparity Distribution and Its Application," Proceedings Am. Statistical Ass. Biopharmaceutical Section, Alexandria, VA, Am. Statistical Ass., 443-447).
DeForge et al., 2004, "Effect of 4-aminopyridine on gait in ambulatory spinal cord injuries: a double-blind, placebo-controlled, crossover trial," Spinal Cord, 42:674-685.
Dekkers et al., 2001, "Treatment of The Neuromuscular Junction With 4-Aminopyridine Results in Improved Reinnervation Following Nerve Injury in Neonatal Rats," Neuroscience 103(1):267-274.
Department of Health & Human Services, Mar. 29, 2010, Warning Letter, http://www.fda.gov/dowloads/ICECI/EnforcementActions/WarningLetters/2001/UCM069491.pdf (last accessed Nov. 16, 2010).
Dimitrijevic et al., 1986, "Spinal cord stimulation for the control of spasticity in patients with chronic spinal cord injury:I. Clinical observations," Cent. Nerv. Syst. Trauma,: J. Am. Paralysis Assoc., 3(2):129-144.
Dimitrijevic et al., 1986, "Spinal cord stimulation for the control of spasticity in patients with chronic spinal cord injury:II. Neurolophysiologic observations," Cent. New. Syst. Trauma,: J. Am. Paralysis Assoc., 3(2):145-152.
Ditunno et al., 2002, "Double-blinded, placebo-controlled, dose-escalating study evaluating the safety and efficacy of oral doses of fampridine-SR (sustained-release-aminopyridine) in patients with chronic spinal cord injury," First Meeting of the American Spinal Injury and the Intl Medical Society of Paraplegia, Vancouver, Canada, May 3-6, 2002 (Poster).
Ditunno et al., 2002, "Double-blind, placebo-controlled, dose-escalating study evaluating the safety and efficacy of oral doses of fampridine-SR (sustained-release 4-aminopyridine) in patients with chronic spinal cord injury," American Spinal Association Twenty-Eight Annual Meeting, p. S35 (Abstract # 78).
Donovan et al., 2000, "Intravenous infusion of 4-AP in chronic spinal cord injured subjects," Spinal Cord, 38:7-15.

(56) References Cited

OTHER PUBLICATIONS

Dubuc et al., 1986, "The effects of 4-aminopyridine on the spinal cord: rhythmic discharges recorded from the peripheral nerves," Brain Res., 369:243-259.
Edgley et al., 1991, "A survey of multiple sclerosis. Part 2: Determinants of employment status," Can. J. Rehab., 4(3):127-132.
Eidelberg et al., 1977, "Relationship between residual hindlimb-assisted locomotion and surviving axons after incomplete spinal cord injuries," Exp. Neurol., 56:312-322.
Eidelberg et al., 1981, "Anatomical correlates of return of locomotor function after partial spinal cord lesions in cats," Exp. Brain Res., 42:81-88.
Eidelberg et al., 1981, "Locomotor control in macaque monkeys," Brain, 104:647-663.
Eliasson et al., 1991, "Effects of 4-aminopyridine on protein phosphorylation in heat-blocked peripheral nerve," J. Neutrol. Sci., 105:175-182.
Eriksson et al., 2002, "Epileptic seizures, cranial neuralgias and paroxysmal symptoms in remitting and progressive multiple sclerosis," Mult. Scler., 8(6):495-499.
European Medicines Agency, ICH Topic E4, Dose Response Information to Support Drug Registration, Reference No. CPMP/ICH/378/95, published May 1994.
Evans, 2000, "Justified deception? The single blind placebo in drug research," J. Med. Ethics 26:188-193.
Evenhuis et al., 1981, "Pharmacokinetics of 4-aminopyridine in human volunteers," Br. J. Anaesth., 53:567-570.
EXTAVIA® (interferon beta-1b), Novartis Pharmaceuticals Inc., Prescribing Information, Aug. 2009. http://www.pharma.us.novartis.com/product/pi/pdf/extavia.pdf (last accessed Nov. 3, 2010).
Faculty, Doctors, Staff, Department of Neurology, Columbia University, New York, last updated Oct. 19, 2010, http://web.neuro.columbia.edu/members/profiles.php?id=91 (last accessed Nov. 17, 2010).
Fampridine Monograph, 1998, "Fampridine Neurelan(R) Agent for Multiple Sclerosis," Drugs Fut., 23(2):218-219.
Fampyra 10 mg prolonged-release tablets—(eMC), last updated Jul. 16, 2013, (http://www.medicines.org.uk/emc/printfriendlydocument.aspx?documentid=25003.
FDA Approval Letter NDA 022250, Jan. 22, 2010.
FDA Guidance for Industry: Bioanalytical Method Validation (May 2001) (pp. 1-22).
FDA Guidance for Industry: Bioavailability and Bioequivalence Studies for Orally Administered Drug Products—General Considerations (Mar. 2003) (pp. 1-23).
FDA Guidance for Industry: Extended Release Oral Dosage Forms: Development, Evaluation, and Application of In Vitro / In Vivo Correlations (Sep. 1997) (pp. 1-24).
FDA Guidance for Industry: Food-Effect Bioavailability and Fed Bioequivalence Studies (Dec. 2002) (pp. 1-9).
FDA, 1994,"Guideline for Industry Dose-Response Information to Support Drug Registration" (http://www.fda.gov/downloads/Drugs/GuidanceComplianceRegulatoryInformation/Guidances/ucm073115.pdf, last accessed Jul. 31, 2014).
Feinstein, 2004, "The neuropsychiatry of multiple sclerosis," Can. J. Psychiatry, 49:157-163.
Final Program, Abstract Listing and Meeting Information, ACTRIMS-ECTRIMS, 7th Annual Meeting of the Americas Committee for Treatment and Research in Multiple Sclerosis and 18th Congress of the European Committee for Treatment and Research in Multiple Sclerosis, Sep. 18-21, 2002, Baltimore, Maryland, USA available at http://main.nationalmssociety.org/docs/HOM/AE2002_program.pdf (last accessed Aug. 16, 2014).
Fingerman, et al., 2000, "The overactive bladder in multiple sclerosis," J. Am. Osteopath. Assoc., 100 (Suppl): S9-S12.
Fischer et al., 1999, "The Multiple Sclerosis Functional Composite measure (MSFC): an integrated approach to MS clinical outcome assessment," Mult. Scler., 5:244-250.
Fischer et al., 2001, "Multiple Sclerosis Functional Compositie (MSFC), Administration and Scoring Manual," rev. Oct. 2001, National Multiple Sclerosis Society, New York, pp. 1-41.
Fleming et al., 1994, "Patterns of comorbidity in elderly patients with multiple sclerosis," J. Clin. Epidemiol., 47:1127-1132.
Folkerth, 2005, "Neuropathologic Substrate of Cerebral Palsy," J. Child Neurol., 20:940-949.
Form S-1 , SEC Accession No. 0001047469-03-031904, filed Sep. 29, 2003.
Form S-1 as filed by Acorda Therapeutics, Inc. with the Securities and Exchange Commission on Sep. 26, 2003.
Freund, 1983, "New Drug Delivery Systems: Scientific and Corporate Implications," Clinical Research and Regulatory Affairs 1(4), 291-301.
Friend et al., 1999, "Language Functions in Patients with Multiple Sclerosis," Clin Neuropsychologist, 13(1):78-94.
Fujihara et al., 1998, "The effects of 4-aminopyridine on motor evoked potentials in multiple sclerosis," J. Neurol. Sci., 159(1):102-106.
Gean, 1990, "The epileptiform activity induced by 4-aminopyridine in rat amygdale slices: antagonism by non-N-methyl-D-aspartate receptor antagonists," Brain Res., 530:251-256.
GILENYA® (fingolimod), Novartis Pharmaceuticals Corporation, Prescribing Information, Sep. 2010. http://www.pharma.us.novartis.com/product/pi/pdf/gilenya.pdf (last accessed Nov. 9, 2010).
Glasauer et al., 2005, "4-Aminopyridine restores visual ocular motor function in upbeat nystagmus," J. Neurol. Neurosurg. Psychiatry, 76:451-453.
Glasauer et al., 2005, "Effect of 4-aminopyridine on upbeat and downbeat nystagmus elucidates the mechanism of downbeat nystagmus," Ann. NY Acad. Sci., 1039:528-531.
Glover, 1982, "The aminopyridines," Gen. Pharmacol., 13(4):259-285.
Gold et al., 1996, "Characterization of six voltage-gated K+ currents in adult rat sensory neurons," J. Neurophysiol., 75:2629-2646.
Goodman et al., 2002, "Placebo-controlled double-blinded dose ranging study of Fampridine-SR in multiple sclerosis," P308, ACTRIMS-ECTRIMS, Abstracts of the 7th Annual Meeting of the Americas Committee for Treatment and Research in Multiple Sclerosis and 18th Congress of the European Committee for Treatment and Research in Multiple Sclerosis, Sep. 18-21, 2002, Baltimore, Maryland, USA, Mult. Scler.; 8 Suppl Posters S116-S117, (Abstract P308).
Goodman et al., Sep. 18-21, 2002, slide presentation entitled "Placebo-controlled double-blinded dose ranging study of fampridine-SR in multiple sclerosis," 7th Annual Meeting of the Americas Committee for Treatment and Research in Multiple Sclerosis and 18th Congress of the European Committee for Treatment and Research in Multiple Sclerosis (ACTRIMS/ECTRIMS) in Baltimore, Maryland, USA.
Goodman et al., Sep. 18-21, 2002, poster entitled "Placebo-controlled double-blinded dose ranging study of fampridine-SR in multiple sclerosis," 7th Annual Meeting of the Americas Committee for Treatment and Research in Multiple Sclerosis and 18th Congress of the European Committee for Treatment and Research in Multiple Sclerosis (ACTRIMS/ECTRIMS) in Baltimore, Maryland, USA.
Goodman et al., 2003, "Placebo-controlled double-blinded dose ranging study of fampridine-SR in multiple sclerosis," Neurology, 60 (5 Suppl. 1), Abstract S21.001, p. A167.
Goodman et al., 2004, "Phase 2 trial of fampridine-SR (sustained-release 4-aminopyridine) in multiple sclerosis," 20th European Committee for Treatment and Research in Multiple Sclerosis, Vienna, Austria, Oct. 6-9, 2004 (Poster).
Goodman et al., 2004, "Phase 2 trial of fampridine-SR in multiple Sclerosis," Multiple Sclerosis, 10(2):S273 (p. 694).
Goodman et al., 2004, "Phase two trial of fampridine-SR in multiple sclerosis," Multiple Sclerosis, 11(1):111.
Goodman et al., 2005, "Clinical meaningfulness of consistent improvement on the timed 25 foot walk (TW25) during treatment with fampridine," 130th Annual Meeting of the American Neurological Association, San Diego, CA, Sep. 25-28, 2005 (Poster).

(56) References Cited

OTHER PUBLICATIONS

Goodman et al., 2005, "Clinical meaningfulness of consistent improvement on the timed 25-foot walk (TW25) during treatment with fampridine," Annals of Neurology, 58(Suppl. 9):S26 (p. 96).
Goodman et al., 2005, "Stability and interrelatedness of the 12-item multiple sclerosis waking scale and the timed 25 foot walk during a 3 month clinical trial," Multiple Sclerosis, 11:S102-S103 (p. 398).
Goodman et al., 2005, "Stability and interrelatedness of the 12-item multiple sclerosis walking scale and the timed 25 foot walk during a 3 month clinical trial," Presented at the ECTRIMS/ACTRIMS Congress, Thessaloniki, Greece, Sep. 2005 (Poster).
Goodman et al., 2008, "Dose comparison trial of sustained-release fampridine in multiple sclerosis," Neurology, 71:1134-1141.
Goodman et al., 2009, "Sustained-Release Oral Fampridine in Multiple Sclerosis: a Randomized, Double-Blind, Controlled Trial," Lancet, 373: 732-738.
Goodman et al., 2010, "A Phase 3 Trial of Extended Release Oral Dalfampridine in Multiple Sclerosis," Ann. Neurol., 68(4):494-502.
Goodman, 2007, "Fampridine-SR in multiple sclerosis: a randomized, double-blind, placebo-controlled, dose-ranging study," Multiple Sclerosis 13:357-368.
Graziani et al., 2002, "Two multicenter trials demonstrate potential efficacy of fampridine-SR (sustained-release 4-aminopyridine) for spasticity management in subjects with chronic spinal cord injury," 63rd Annual Academy of Physical Medicine and Rehabilitation Assembly, Orlando, FL Nov. 21-23, 2002 (Poster).
Grijalva et al., 2003, "The efficacy and safety of 4-aminopyridine in patients with long-term spinal cord injury: a randomized, double-blind, placebo-controlled trial," Pharmacotherapy, 23:823-834.
Grimaldi et al., 2001, "Mobilization of Calcium from Intracellular Stores, Potentiation of Neurotransmitter-Induced Calcium Transients, and Capacitative Calcium Entry by 4-Aminopyridine," J. Neurosci. 21(9):3135-3143.
Grounds of Appeal dated Nov. 8, 1996 with Annexes 1-4 filed in European Patent Application No. 91310143.2 filed Nov. 1, 1991.
Gruner et al., 1987, "Recovery of Motor Function in Chronic Experimental Spinal Cord Injury Enhanced by 4-Aminopyridine," Society for Neuroscience Abstracts, 13(1):62 (abstr. 21.16).
Gutman et al., 2005, "International Union of Pharmacology. LIII. Nomenclature and molecular relationships of voltage-gated potassium channels," Pharmacol. Rev., 57(4):473-508.
Guy W. Ecdeu Assessment Manual for Psychopharmacology—Revised (DHEW Publ No. ADM 76-338). US Dept of Health Education & Welfare, Public Heath Service, Div of Exramural Research Programs, 1976: 218-222.
Haghighi et al., 1995, "Effect of 4-aminopyridine in acute spinal cord injury," Surg. Neurol., 43(5):443-447.
Haghighi et al., 1998, "Effect of 4-aminopyridine and single-dose methylprednisolone on functional recovery after a chronic spinal cord injury," Spinal Cord, 36:6-12.
Halter et al., 2000, "Intrathecal administration of 4-aminopyridine in chronic spinal injured patients," Spinal Cord, 38(12):728-732.
Hansebout et al., 1993, "K. 4-Aminopyridine in Chronic Spinal Cord Injury: A Controlled, Double-Blind, Crossover Study in Eight Patients," J. Neurotrauma, 10(1):1-18.
Hapoalim Securities, "Acorda Therapeutics (ACOR)," Nov. 1, 2010 (pp. 1-10).
Hapoalim Securities, "Acorda Therapeutics, (ACOR)," Aug. 4, 2010 (pp. 1-7).
Hassan et al.,1980, "Double-blind comparison of single doses of DS103-282, baclofen and placebo for suppression of spasticity," J. of Neurology Neurosurgery and Psychiatry, 43:1132-1136.
Hauser et al., 1993, "Incidence of epilepsy and unprovoked seizures in Rochester, Minnesota: 1935-1984," Epilepsia, 34(3):453-468.
Hayes et al., 1991, "Effects of intravenous 4-aminopyridine on neurological function in chronic spinal cord injured patients: preliminary observations," Proc. IBRO World Conference Neurosci., p. 345.
Hayes et al., 1993, "Preclinical Trial of 4-Aminopyridine in Patients with Chronic Spinal Cord Injury," Paraplegia, 31:216-224.

Hayes et al., 1994, "4-Aminopyridine sensitive neurologic deficits in patients with spinal cord injury," J. Neurotrauma, 11(4):433-446.
Hayes et al., 2001, "Open-label, multiple-dose study to determine the pharmacokinetics and safety of fampridine-SR (sustained-release 4-aminopyridine) in patients with chronic spinal cord injury," Presented to the American Neurological Association, Chicago, IL, Sep. 30-Oct. 3, 2001 (Poster).
Hayes et al., 2001, "Open-label, multiple-dose study to determine the pharmacokinetics and safety of fampridine-SR in patients with chrothe spinal cord injury," Annals of Neurology, 50(31):S62 (201).
Hayes et al., 2001, "Pharmacokinetics and safety of multiple oral doses of fampridine-SR (sustained-release 4-aminopyridine) tablets in patients with chronic spinal cord injury," Presented to the Academy of Physical Medicine and Rehabilitation, New Orleans, LA, Sep. 13-16, 2001 (Poster).
Hayes et al., 2003, "Pharmacokinetics of an Immediate-Release Oral Formulation of Fampridine (4-Aminopyridine) in Normal Subjects and Patients with Spinal Cord Injury," J. Clin. Pharmacol., 43:379-385.
Hayes et al., 2003, "Pharmacokinetics Studies of Single and Multiple Oral Doses of Fampridine-SR (Sustained-Release 4-Aminopyridine) in Patients With Chronic Spinal Cord Injury," Clinical Neuropharmacology, 26(4):185-192.
Hayes et al., 2004, "Pharmacokinetics and Safety of Multiple Oral Doses of Sustained-Release 4-Aminopyridine (Fampridine-SR) in Subjects With Chronic, Incomplete Spinal Cord Injury," Arch. Phys. Med. Rehabil. 85:29-34.
Hayes, 2004, "The Use of 4-Aminopyridine (Fampridine) in Demyelinating Disorders," CNS Drug Reviews, 10(4):295-316.
Heng et al., 2001, "Investigation of the influence of mean HPMC particle size and number of polymer particles on the release of aspirin from swellable hydrophilic matrix tablets," Journal of Controlled Release, 76:39-49.
Heyn, 1904, "Berlin's Wonderful Horse: He Can Do Almost Everything but Talk—How He Was Taught," The New York Times, Sep. 4, 1904.
Higuchi et al., 1975, "Pro-drugs as novel delivery systems," vol. 14 of the ACS Symposium Series (TOC).
Hobart et al., 2003, "Measuring the impact of MS on walking ability: the 12-Item MS Walking Scale (MSWS-12)", J. Neurology, 60:31-36.
Hoogervorst et al., 2004, "The patient's perception of a (reliable) change in the Multiple Sclerosis Functional Composite," Multi. Soler., 10:55-60.
Hyland, 2003, "Using the placebo response in clinical practice," Clin. Med. 3:347-350.
ICH Harmonized Tripartite Guideline, Dose-Response Information to Support Drug Registration, Step 4 Version, Mar. 10, 1994.
Illis et al., 1983, "Spinal cord stimulation in the United Kingdom (Review)," J. Neurol. Neurosurg. Psychiat., 46:299-304.
Information Disclosure Statement with Statement of Relevance for Prior Art filed May 4, 1992 in U.S. Appl. No. 7/786,400, filed Nov. 1, 1991.
Interlocutory Decision in Opposition Proceedings dated Dec. 19, 2013 regarding EP 1732548.
International Preliminary Report on Patentability with Written Opinion from International Application No. PCT/US04/08101, dated Sep. 23, 2005.
International Preliminary Report on Patentability with Written Opinion from International Application No. PCT/US05/012427, dated Oct. 11, 2006.
International Search Report from International Application No. PCT/US04/08101, dated Aug. 26, 2004.
International Search Report from International Application No. PCT/US05/12427, dated Dec. 28, 2005.
International Search Report from International Application No. PCT/US09/56476, dated Nov. 10, 2009.
International Search Report from International Application No. PCT/US10/23969, dated Apr. 1, 2010.
International Search Report from International Application No. PCT/US10/23970, dated Apr. 5, 2010.

(56) References Cited

OTHER PUBLICATIONS

Iriarte et al., 2000, "Modalities of fatigue in multiple sclerosis: correlation with clinical and biological factors," Mult. Scler., 6:124-130.
Isoda et al., 2003, "The effects of 4-aminopyridine on cardiac repolarization, PR interval, and heart rate in patients with spinal cord injury," Pharmacotherapy, 23:133-136.
J.P. Morgan, "Acorda Therapeutics," Aug. 3, 2010 (p. 1-7).
Jack et al., 1981, "Modifications to synaptic transmission at group la synapses on cat spinal motoneurons by 4-aminopyridine," J. Physiol., 321:111-126.
Jackson et al., 2002, "Twice-daily fampridine-SR (sustained-release 4-aminopyridine): safety and early efficacy experience in 151 patients with chronic motor-incomplete spinal cord injury," 127th Annual Meeting American Neurological Association, NY, NY Oct. 13-16, 2002 (Poster).
Jacobs et al., 1990, "Foot salvage and improvement of microsvascular blood flow as a result of epidural spinal cord electrical stimulation," J. Vasc. Surg., 12(3):354-360.
Jankowska et al., 1977, "Effects of 4-aminopyridine on transmission in excitatory and inhibitory synapses in the spinal cord," Brain Res., 136:387-392.
Jankowska et al., 1982, "Effects of 4-aminopyridine on synaptic transmission in the cat spinal cord," Brain Res., 240:117-129.
Jellinger, 1976, "Neuropathology of cord injuries," Handbook of Clinical Neurology, vol. 25, Part I, Injuries of the Spine and Spinal Cord. Vinken et al. eds., North-Holland: Amsterdam, 1976, pp. 43-121.
Jones et al., 1983, "Effects of 4-Aminopyridine in Patients with Multiple Sclerosis," J. Neurol Sci., 60:353-362.
Josephson et al., 1984, "Early outward current in rat single ventricular cells," Circ. Res., 54:157-162.
Juarez et al., 2001, "Influence of admixed carboxymethylcellulose on release of 4-aminopyridine from hydroxypropyl methylcellulose matrix tablets," Intl. J. of Pharmaceutics, 216:115-125.
Judge et al., 1999, "Inactivation gating and 4-AP sensitivity in human brain Kv1.4 potassium channel," Brain Research, 831:43-54.
Judge et al., 2002, Determinants of 4-Aminopyridine Sensitivity in a Human Brain Kv1.4K+ Channel: Phenylalanine Substitutions in Leucine Heptad Repeat Region Stabilize Channel Closed State, Mol. Pharmacol., 61:913-920.
Kachuck, 2009, "Sustained release oral fampridine in the treatment of multiple sclerosis," Expert Opinion, 10(12):12:2025-2035.
Kakulas et al., 1969, "A correlative clinico-pathologic study of spinal cord injury," Proc. Aust. Assoc. Neurologists, 6:123-132.
Kakulas et al., 1990, "The neuropathology of pain and abnormal sensations in human spinal cord injury derived from the clinicopathological data base at the Royal Perth Hospital," Recent Achievements in Restorative Neurology, 3: Altered Sensation and Pain, Dimitrijevic et al eds., Karger:Basel, pp. 37-41.
Kakulas, 1984, "Pathology of spinal injuries," Cent. Nerv. Syst. Trauma, 192:117-129.
Kalla et al., 2004, "4-aminopyridine improves downbeat nystagmus, smooth pursuit, and VOR gain," Neurology, 62(7):1228-1229.
Katz et al., 2001, "Pharmacokinetics and safety of single oral doses of fampridine (immediate-release 4-aminopyridine) capsules in health volunteers," Presented to the American Academy of Physical and Rehabilitation, New Orleans, LA, Sep. 13-16, 2001 (Poster).
Katz et al., 2002, "Pharmacokinetics and excretion of a single oral dose of 14c-labeled fampridine (4-aminopyridine) in healthy volunteers," 1st Joint Mtg of the American Spinal Injury Association and the Intl. Medical Society of Paraplegia, Vancouver, Canada, May 3-6, 2002 (Poster).
Kaufman et al., 2000, "The significant change for the timed 25-foot walk in the Multiple Sclerosis Functional Composite," Mult. Scler., 5:286-290.
Khan et al., 2002, "Highlights From the Second Joint Meeting of the Americas and European Committees for Treatment and Research in Multiple Sclerosis (ACTRIMS and ECTRIMS)," available at http://www.mult-sclerosis.org/news/Oct2002/HighlightsfromACTRIMSECTRIMS.html (last accessed Aug. 16, 2014).
Kirchhoff et al., 1992, "Excitation of cutaneous sensory nerve endings in the rat by 4-aminopyridine and tetraethylammonium," J. Neurophysiol., 67(1):125-131.
Kobelt et al. 2006, Costs and quality of life in multiple sclerosis: a cross-sectional study in the United States, Neurology, 66:1696-1702.
Kocsis et al., 1983, "Effects of extracellular potassium concentration on the excitability of the parallel fibers of the rat cerebellum," J. Physiol. (Lond) 334:225-244.
Kocsis et al., 1986, "Different effects of 4-aminopyridine on sensory and motor fibers: pathogenesis of paresthesias," Neurology, 36:117-120.
Kos et al., 2004, "Letter to the Editor," Multiple Sclerosis, Jun. 1, 2004, 10/3 (337-338).
Kostka et al., 1992, "Column liquid chromatographic determination of 4-aminopyridine in plasma and urine after derivatization with benzoyl chloride," Clin. Biochem., 25:144.
Kovacs et al., 2003, "Seizure, neurotransmitter release, and gene expression are closely related in the striatum of 4-aminopyridine-treated rats," Epilepsy Res., 55(1-2):117-129.
Kurtzke et al., 1983, "Rating neurologic impairment in multiple sclerosis: an expanded disability status scale (EDSS)," Neurology, 33:1444-1452.
Lammertse et al., 2002, "Clinical evaluation of oral fampridine-SR (sustained-release 4-aminopyridine) in subjects with chronic motor-incomplete spinal cord injury," 54th Annual Meeting of the American Academy of Neurology, Denver, CO, Apr. 13-20, 2002 (Poster).
Lammertse et al., 2002, "Evaluation fampridine-SR in patients with chronic spinal cord injury," 48th Conference of the Paraplegia Society, Las Vegas, NV, Sep. 3-5, 2002 (Poster).
Lammertse et al., 2002, "Clinical evaluation of oral fampridine-SR (sustained-release 4-aminopyridine) in patients with chronic motor-incomplete spinal cord injury," Neurology, 58 (7 Suppl. 3): A33 (P01.035).
Landete et al., 1998, "Low doses of 4-aminopyridine in the treatment of multiple sclerosis," Multiple Sclerosis, 4:386 (Abstract P3047).
Lazard Capital Markets, "Acorda Therapeutics (ACOR)," Aug. 24, 2010 (pp. 1-15).
Lazard Capital Markets, "Acorda Therapeutics," Aug. 3, 2010 (pp. 1-3).
Leary et al., 2003, "Interferon beta-1a in primary progressing MS—An exploratory, randomized, controlled trial," Neurology, 60:44-51.
Lee and Robinson, "Methods to achieve sustained drug delivery," Sustained and Controlled Release Drug Delivery Systems (Joseph R. Robinson ed. 1978), 123-209.
Lemeignan et al., 1981, "The ability of 4-aminopyridine and 3,4-diaminopyridine to cross the blood-brain barrier can account for their difference in toxicity," Adv. Biosci., 35:222.
Lemeignan, 1972, "Analysis of the action of 4-aminopyridine on the cat lumbar spinal cord. 1. Modification of the afferent volley, the monosynaptic discharge amplitude and the polysynaptic evoked responses," Neuropharm., 11:551-558.
Liang et al., 2005, "Effects of pelvic nerve neurectomy and estrogen on the M2 muscarinic receptor of the urinary bladder," Chang Gung Med. J., 28:786-793.
Linderoth et al., 1991, "Peripheral vasodilatation after spinal cord stimulation: Animal studies of putative effector mechanisms," Neurosurgery, 28(2):187-195.
Llinas et al., 1982, 3- and 4-aminopyridine in synaptic transmission at the squid giant synapses, in: Aminopyridines and similarly acting Drugs: Effects on nerves, muscles and Synapses, Lechat et al. eds., Pergamon Press: Oxford, pp. 69-79.
Longer et al., 1985, "Sustained-Release Drug Delivery Systems" Remington's Pharmaceutical Sciences, A. Gennaro, Ed., Mack Publishing Company, Easton, PA, 1644-1661.

(56) References Cited

OTHER PUBLICATIONS

Longer et al., 1990, "Sustained-Release Drug Delivery Systems" Remington's Pharmaceutical Sciences, A. Gennaro, Ed., Mack Publishing Company, Easton, PA, 1676-1693.
Loss of mobility found to impact quality of life and emotional and financial health of most people living with multiple sclerosis, National Multiple Sclerosis Society, Mar. 2008, http://www.nationalmssociety.org/news/news-detail/index.aspx??nid=199 (last accessed Nov. 3, 2010).
Lublin et al., 1996, "Defining the clinical course of multiple sclerosis: Result of an international survey," Neurology, 46:907-911.
Lundh et al., 1977, "4-Aminopyridine—A new drug tested in the treatment of Eaton-Lambert syndrome," J. Neuro. Neurosurg. Psych., 40:1109-1112.
Lundh et al., 1979, "Effects of 4-Aminopyridine in Myasthenia Gravis," J. Neuro. Neurosurg. Psychiatry, 42:171-175.
Lundh et al., 1979, "Effects of 4-aminopyridine on statistical parameters of transmitter release at the neuromuscular junction," Acta Pharmacol. Toxicol., 44(5):343-346.
Lundh et al., 1982, "Lack of effect of 4-aminopyridine on choreic movements," J. Neurol. Neurosurg. Psychiatry, 45(3):274-275.
Lundh et al., 1983, "Novel drug of choice in Eaton-Lambert syndrome," J. Neurol. Neurosurg. Psychiatry, 46(7):684-685.
Lundh, 1978, "Effects of 4-aminopyridine on neuromuscular transmission," Brain Research, 158(2):307-318.
Lyseng-Williamson et al., 2002, "Management of Relapse-Remitting Multiple Sclerosis," Disease Management and Health Outcomes 10(5), 307-325.
Magdalan et al., 2003, "[Successful treatment by 4-aminopyridine of three cases of severe verapamil poisoning]," [Article in Polish] Przegl. Lek., 60(4):271-273 (English translation attached).
Marchand et al., 1991, "The effects of dorsal column stimulation on measures of clinical and experimental pain in man," Pain, 45:249-257.
Marinucci et al., 2007, "The Range Disparity Distribution and Its Application," Proceedings Am. Statistical Ass. Biopharmaceutical Section, Alexandria, VA, Am. Statistical Ass., 443-447.
Martin et al. 2006, "Gait and balance impairment in early multiple sclerosis in the absence of clinical disability," Multiple Sclerosis, 12:620-628.
Martinez-Aguirre et al., 1986, "Comparison of midazolam (RO 21-3981) and diazepam as complement of ketamine-air anesthesia in children," Acta Anesth. Belg., 37(1):15-22.
Martinez-Aguirre, 1980, "Antagonism of 4-aminopyridine to ketamine-diazepam anesthesia in children," Acta. Anaesthesiol. Belg., 31(4):289-291.
Martinez-Aguirre, 1982, "Antagonism of ketamine by 4-aminopyridine and physostigmine," Br. J. Anesth., 54(1):110.
Martinez-Gonzalez et al., 2003, "Effect of varying the restriction degree of 4-aminopyridine release from HPMC matrices on the mechanism controlling the process," Int. J. Pharmaceutics, 257:253-264.
Martinez-Gonzalez et al., 2003, "Influence of enteric citric acid on the release profile of 4-aminopyridine from HPMC matrix tablets," Intl. J. of Pharmaceutics, 251:183-193.
Martinez-Gonzalez et al., 2004, "Influence of enteric-coated lactose on the release profile of 4-aminopyridine from HPMC matrix tablets," Pharmaceutical Development and Technology, 9(2):145-153.
Matthews, 1998, "Symptoms and signs of multiple sclerosis," Chap. 5, in McAlpine's Multiple Sclerosis, 3d ed., Compston et al., (eds), Churchill Livingstone, at pp. 145-190; McDonald & Compston.
Matthews, B., 1998, "Differential diagnosis of multiple sclerosis and related disorders," Chap. 4 in McApline's Multiple Sclerosis, Compston et al. (eds.), Churchill Livingstone at pp. 228-243.
McCafferty Declaration dated Nov. 7, 1996 filed in European Patent Application No. 91310143.2 filed Nov. 1, 1991.

Compston, 1998, "The story of multiple sclerosis," Chapter 1, in McAlpine's Multiple Sclerosis, 3rd ed., Compston et al., (eds.), Churchill Livingstone Elsevier, pp. 3-42.
McDonald & Compston, 2005, "The symptoms and signs of multiple sclerosis," Chapter 6, in McAlpine's Multiple Sclerosis, 4th ed., Compston et al., (eds.), Churchill Livingstone Elsevier, at pp. 287-346.
McFarlin et al., 1982, "Multiple sclerosis (first of two parts)," N. Engl. J. Med. 307(19):1183-1388.
McGuigan et al., 2004, "Confirming the validity and responsiveness of the Multiple Sclerosis Walking Scale-12 (MSWS-12)," Neurology, 62:2103-2105.
Mealy et al., "Neurologic Drugs," Drugs of the Future 27(9), 879-915.
Medical Research Council (MRC), 1976, "Memorandum No. 45—Aids to the examination of the peripheral nervous system, London: Her Majesty's Stationery Office," Printed in London for Her Majesty's Stationary Office, The White Rose Press, Mexborough and London, pp. 1-62.
Meglio et al.,1981, "Spinal cord stimulation and peripheral blood flow: Part 1, In: indications for spinal cord stimulation," Y. Hosebuchi and T. Corbin (eds), Excerpta Medica: Amsterdam, pp. 60-66.
Mellor, 2002, "ACTRIMS/ECTRIMS 2002 Trip Report—Art Mellor" available at http://msnews.acceleratedcure.org:8080/editions?page=297 (last accessed Aug. 16, 2014).
Memorandum on "NDA 22250 for Fampridine Sustained Release (Amaya)," Department of Health and Human Services, Public Health Service, Food and Drug Administration (Sep. 16, 2009).
Mestinon(R) Timespan (R) Prescribing Information, Physician's Desk Reference (1989).
Metz et al., 1998, "Urinary tract infections may trigger relapse in multiple sclerosis," Axone, 19:67-70.
Mihai et al., 1997, "Selection criteria for interferon beta 1-b in multiple sclerosis patients," Neurology, 48 (3 Suppl. 2):A348 (S48.005).
Miller et al., 1979, "4-Aminopyridine Potentiates Neostigmine and Pyridostigmine in Man," Anesthesiology, 50:416-420.
Minden et al., 1990, "A Psychiatric Perspective," Chapter 15, pp. 230-250 in "Neurobehavioral Aspects of Multiple Sclerosis," Rao (ed.), Oxford University Press.
Mitsov, 1988, "Analgesic activity of pimadine (4-aminopyridine)," Jul.-Aug. 1988, Russian J. of Pharmacology and Toxology, 51(4):122-125.
Molgo et al., 1977, "Effects of 4-aminopyridine at the frog neuromuscular junction," J. Pharmacol Exp. Ther., 203(3):653-663.
Molgo et al., 1980, "Potency of 3,4-diaminopyridine and 4-aminopyridine on mammalian neuromuscular transmission and the effect of pH changes," Eur. J. Pharmacol., 61(1):25-34.
Molgo, 1982, Effects of aminopyridines on neuromuscular transmission, in: Aminopyridines and Similarly Acting Drugs: Effects on Nerves, Muscles and Synapses, Lechat et al. eds., Pergamon Press: Oxford, pp. 95-116.
Moritoki et al., 1978, "Actions of aminopyridines on guinea-pig ileum," Arch. Int. Pharmacodyn. Ther., 232:28-41.
Morning Show Ratings—TvNewser, Ratings of Week of Nov. 1, 2010, http://www.mediabistro.com/tvnewser/category/morning-show-ratings (last accessed Nov. 17, 2010).
MS Hope for a Cure, 2010, http://www.mshopeforacure.org/board.php#elissa (last accessed Nov. 17, 2010).
Multiple Sclerosis—PubMed Health (http://www.ncbi.nlm.nih.gov/pubmedhealth/PMH0001747/; last accessed May 12, 2013).
Murray et al., 1981, "Treatment with Oral 4-Aminopyridine in Disorders of Neuromuscular Transmission," Neurology, 31:265-271.
Murray, 2000, "The History of Multiple Sclerosis," Multiple Sclerosis, Diagnosis, Medical Management, and Rehabilitation: Demos Medical Publishing, Inc., pp. 1-32.
Myers, 1990, "Therapy of multiple sclerosis," Neurology and Neurosurgery, 3:208-212.
National Multiple Sclerosis Society homepage on the Internet, http://www.nationalmssociety.org/index.aspx (last accessed Nov. 2, 2010).

(56) References Cited

OTHER PUBLICATIONS

National Multiple Sclerosis Society Report on American Academy of Neurology's 55th Annual Meeting in Honolulu Mar. 29-Apr. 5, 2003, available at https://groups.google.com/forum/#!topic/alt.support.mult-sclerosis/VSuyQoHSXpg (last accessed Aug. 16, 2014).
National Multiple Sclerosis Society, "FSS and EDSS," http://www.nationalmssociety.org/for-professionals/reearchers/clinical-study-measures/fss-and-edss/index.aspx (last accessed Nov. 17, 2010).
NG et al., 1987, "Studies on the calcium dependence of human NK cell killing," Biochem. Pharmacol., 36:3943-3949.
Nicoletti et al., 2003, "Epilepsy and multiple sclerosis in Sicily: a population-based study," Epilepsia, 44(11):1445-1448.
Nikolova et al., 2001, "Therapeutic Efficacy of 4-Aminopyridine on Neurological and Cognitive Deficit in Multiple Sclerosis," JNS 187, Suppl. 1, p. S457.
Noble et al., 1989, "Correlative analyses of lesion development and functional status after graded spinal cord contusive injuries in the rat," Exp. Neurol., 103:34-40.
Nockles et al., 1992, "Pharmacologic strategies in the treatment of experimental spinal cord injury," J. Neurotrauma, 9, Supplement 1:S211-S217.
Noordenbos et al., 1976, "Diverse sensory functions with an almost totally divided spinal cord. A case of spinal cord transaction with preservation of part of one anterolateral quadrant," Pain, 2:185-195.
Noseworthy, 2003, "Multiple Sclerosis and Related Conditions," Chap.97, in Neurological Therapeutics: Principle and Practices, 1: Noseworthy, JH (ed.) pp. 1107-1131.
NOVANTRONE® (interferon beta-1b), EMD Serono Inc., Prescribing Information, Sep. 2009. http://www.novantrone.com/assets/pdf/novantrone_prescribing_info.pdf (last accessed Nov. 3, 2010) (pp. 1-34).
Ochoa, 1982, "Pain in local nerve lesions," Abnormal Nerves and Muscles as Impulse Generators, Culp et al. eds., Oxford University Press: New York, pp. 568-587.
Office Action dated Apr. 14, 2010 for U.S. Appl. No. 11/102,559, filed Apr. 8, 2005.
Office Action dated Apr. 2, 2014 for U.S. Appl. No. 12/626,085, filed Nov. 25, 2009.
Office Action dated Apr. 25, 2012 for U.S. Appl. No. 12/626,085, filed Nov. 25, 2009.
Office Action dated Apr. 29, 2014 for U.S. Appl. No. 13/585,277, filed Aug. 14, 2012.
Office Action dated Aug. 12, 2011 for U.S. Appl. No. 12/824,140, filed Jun. 25, 2010.
Office Action dated Aug. 16, 2011 for U.S. Appl. No. 12/824,135, filed Jun. 25, 2010.
Office Action dated Aug. 16, 2011 for U.S. Appl. No. 12/824,141, filed Jun. 25, 2010.
Office Action dated Aug. 22, 2011 for U.S. Appl. No. 12/824,136, filed Jun. 25, 2010.
Office Action dated Aug. 30, 2011 for U.S. Appl. No. 12/824,133, filed Jun. 25, 2010.
Office Action dated Jan. 23, 2008 for U.S. Appl. No. 11/102,559, filed Apr. 8, 2005.
Office Action dated Jun. 10, 2009 for U.S. Appl. No. 11/010,828, filed Dec. 13, 2004.
Office Action dated Jun. 13, 2012 for U.S. Appl. No. 13/299,969, filed Nov. 18, 2011.
Office Action dated Jun. 23, 2009 for U.S. Appl. No. 11/102/559, filed Apr. 8, 2005.
Office Action dated Jun. 6, 2008 for U.S. Appl. No. 11/010,828 filed Dec. 13, 2004.
Office Action dated May 25, 2010 for U.S. Appl. No. 11/010,828, filed Dec. 13, 2004.
Office Action dated May 8, 2014 for U.S. Appl. No. 14/025,248, filed Sep. 12, 2013.
Office Action dated Oct. 16, 2013 for U.S. Appl. No. 13/585,277, filed Aug. 14, 2012.
Office Action dated Oct. 29, 2008 for U.S. Appl. No. 11/102,559, filed Apr. 8, 2005.
Office Action dated Oct. 7, 2013 for U.S. Appl. No. 12/626,085, filed Nov. 25, 2009 (mailed to Carol Gruppi Oct. 15, 2013).
Office Action dated Sep. 13, 2011 for U.S. Appl. No. 12/626,001, filed Nov. 25, 2009.
Office Action dated Sep. 16, 2011 for U.S. Appl. No. 12/626,036, filed Nov. 25, 2009.
Office Action dated Sep. 16, 2011 for U.S. Appl. No. 12/626,085, filed Nov. 25, 2009.
Office Action dated Sep. 17, 2010 for U.S. Appl. No. 11/102,559, filed Apr. 8, 2005.
Office Action dated Sep. 4, 2013 for U.S. Appl. No. 13/949,889, filed Jul. 24, 2013.
Office Action dated Sep. 8, 2011 for U.S. Appl. No. 12/824,137, filed Jun. 25, 2010.
Office Action dated Feb. 4, 2015 for U.S. Appl. No. 14/025,248, filed Sep. 12, 2013.
Office Action dated Jun. 5, 2015 for U.S. Appl. No. 13/585,277, filed Aug. 14, 2012.
Office Action dated Sep. 28, 2015 for U.S. Appl. No. 12/626,085, filed Nov. 25, 2009.
Office Action dated Oct. 16, 2015 for U.S. Appl. No. 14/531,191, filed Nov. 3, 2014.
Office Action dated Jan. 22, 2015 for U.S. Appl. No. 14/531,191, filed Nov. 3, 2014.
Office Action dated Nov. 13, 2013 for U.S. Appl. No. 13/829,221, filed Mar. 13, 2013.
Examiner's Answer mailed on Sep. 28, 2015 to Appeal Brief filed May 1, 2015, for U.S. Appl. No. 12/626,085, filed Nov. 25, 2009.
Ogawa et al., 1986, "Combined mutagenicity of cobalt(II) salt and heteroaromatic compounds in *Salmonella typhimurium*," Mutation Research, 172:97-104.
Oh et al., 2003, "Inhibitory effects of potassium channel blockers on carbachol-induced contraction in rat detrusor muscle," J. Korean Med. Sci., 18:701-706.
Olaffson et al., 1999, "Risk of epilepsy in patients with multiple sclerosis: a population-based study in Iceland," Epilepsia, 40(6):745-747.
Olafsson et al., 1996, "Incidence of epilepsy in rural Iceland: a population-based study," Epilepsia, 37(19):951-955.
Olgiati et al., 1988, "Increased Energy Cost of Walking in Multiple Sclerosis: Effect of Spasticity, Ataxia, and Weakness," Arch. Phys. Med. Rehabil., 69:846-849.
Oosterhuis HJ. 1996, "Severe 4-aminopyridine intoxication in a body-builder. Letter to the Editor," Ned. Tijdschr. Geneeeskd., 140(8):452 [Translation provided].
Opposition of EP 1732548 B1, Communication from European Patent Office dated Jun. 14, 2013.
Opposition of EP 1732548 B1, Submission by neuraxpharm Arzneimittel GmbH dated Sep. 11, 2013 with Expert Opinion of Dr. Loebbert (with English translation).
Opposition of EP 1732548 B1, Submission by Synthon B.V. dated Sep. 9, 2013.
Opposition to EP 1732548 B1 by neuraxpharm Arzneimittel GmbH, filed Mar. 8, 2012 (with English Translation).
Opposition to EP 1732548 B1 by neuraxpharm Arzneimittel GmbH, Grounds of Appeal, filed Apr. 29, 2014 (with English Translation).
Opposition to EP 1732548 B1 by Synthon B.V., filed Mar. 7, 2012.
Opposition to EP 1732548 B1 by Synthon B.V., Grounds of Appeal, filed Apr. 28, 2014.
Opposition to EP 2377536 B1 filed by Actavis Group PTC ehf on Dec. 5, 2013.
Opposition to EP 2377536 B1 filed by neuraxpharm Arzneimittel GmbH on Dec. 6, 2013 (with English translation).
Opposition to EP 2377536 B1 filed by Synthon B.V. on Dec. 6, 2013.
Oremus et al., 2000, "Review of outcome measurement instruments in Alzheimer's Disease drug trials: psychometric properties of global scales," J. Geriatr. Psychiatry Neurol., 13: 197-205.
Pant et al., 1982, "Calcium dependent 4 aminopyridine stimulation of protein phosphorylation in squid loligo-pealei optic lobe synaptosomes," Cellular and Molecular Neurobiology, 3(3):223-238.

(56) References Cited

OTHER PUBLICATIONS

Paskov et al., 1973, "New Anti-Curare and Analeptic Drug, Pimadin, and its Use in Anesthesia," Eksp. Khir. Anestheziol., 18(4):48-52 (English translation provided).
Pearson, et al., 2004, "Quantification of walking mobility in neurological disorders," Q. J. Med. New Series, 97:463-475.
Pena et al., 2000, "Seizures and neurodegeneration induced by 4-aminopyridine in rat hippocampus in vivo: role of glutamate- and GABA-mediated neurotransmission and of ion channels," Neuroscience, 101(3):547-561.
Pickett et al., 1996, "Atypical presentation of 4-aminopyridine overdose," Ann. Emerg. Med., 27:382-385.
Pickett et al., 1996, "Fampridine Overdose," Reactions, 30(594):8.
Piper Jaffray, "Acorda Therapeutics," Nov. 2, 2010 (pp. 1-8).
Pogue et al., 1998, "Overcoming the limitations of current meta-analysis of randomized controlled trials," Lancet, 351:47-52.
Polman et al., 1990, "4-Aminopyridine in Multiple Sclerosis," Ann. Neurol., 28(4):589.
Polman et al., 1994, "4-Aminopyridine is Superior to 3,4-Diaminopyridine in the Treatment of Patients With Multiple Sclerosis," Arch. Neurol., 51:1136-1139.
Polman et al., 1994, "4-Aminopyridine in the Treatment of Patients With Multiple Sclerosis," Arch. Neurol., 51:292-296.
Poser et al., 2003, "Epilepsy and multiple sclerosis," Epilepsy & Behavior, 4:6-12.
Potter et al., 1993, "Effects of intravenous 4-aminopyridine on central conduction in persons with incomplete spinal cord injury," Clinical and Investigative Medicine, 16(4Suppl.):B111 (Abstract 693).
Potter et al., 1998, "Randomized Double-Blind Crossover Trial of Fampridine-SR (Sustained Release 4-Aminopyridine) in Patients With Incomplete Spinal Cord Injury," J. Neurotrauma, 15(10):837-849.
Potter et al., 1998, "Sustained Improvements in Neurological Function in Spinal Cord Injured Patients Treated with Oral 4-Aminopyridine: Three Cases," Spinal Cord, 36:147-155.
Pratt et al., 1995, "Plasma and cerebrospinal fluid concentrations of 4-aminopyridine following intravenous injection and metered intrathecal delivery in canines," J. Neurotrauma, 12(1):23-39.
Preliminary Amendment filed Aug. 16, 1993 in U.S. Appl. No. 08/073,651, filed Jun. 7, 1993.
Press Release of Acorda Therapeutics, Inc. dated Aug. 13, 2012 entitled: "Acorda Therapeutics Announces Top Line Results of Post-Marketing Commitment Study Exploring 5 mg Dose of Dalfampridine-ER" available at http://ir.acorda.com/phoenix.zhtml?c=194451&p=irol-newsArticle&ID=1724941&highlight= (last accessed Aug. 17, 2012).
Press Release, Sanofi-Aventis (Apr. 29, 2010), http://en.sanofi-aventis.com/press/press_releases/2010/ppc_28189.asp (last visited Nov. 2, 2010).
Proprietor's Response to the Notices of Opposition for European Patent No. 1732548B9, filed Jan. 2, 2013.
Prous et al., 1995, "Fampridine: agent for multiple sclerosis," Drugs of the Future, 20:142-143.
Qiao et al., 1997, "Effects of 4-aminopyridine on motor-evoked potentials in patients with spinal cord injury," J. Neurotrauma, 14(3):135-149.
REBIF® (interferon beta-1a), EMD Serono Inc. and Pfizer Inc., Prescribing Information, Sep. 2009. http://www.emdserono.com/cmg.emdserono_us/en/images/rebif_tcm115_19765.pdf (last accessed Nov. 3, 2010).
Request for an Administrative Declaration of Invalidation, *Nafar Laboratorios, S.A. de C.V.* vs *Acorda Therapeutics, Inc.*, filed May 22, 2013 at Mexican Institute of Industrial Property (with English translation).
Response filed Aug. 8, 1995 in European Patent Application No. 91310143.2 filed Nov. 1, 1991.
Response filed Feb. 24, 1995 in European Patent Application No. 91310143.2 filed Nov. 1, 1991.
Response filed Feb. 9, 1996 in European Patent Application No. 91310143.2. filed Nov. 1, 1991.
Response filed Mar. 3, 1994 in U.S. Appl. No. 08/073,651, filed Jun. 7, 1993.
Response to Communication Issued Pursuant to Article 94(3) EPC dated Oct. 26, 2009 for European Patent Application No. 05732613.4, filed Mar. 5, 2010.
Riggs, 1982, "Pharmacologic enhancement of neuromuscular transmission in myasthenia gravis," Clin. Neuropharmacol., 5(3):277-292.
Roche, 1987, "Bioreversible carriers in drug designs," American Pharmaceutical Association and Pergamon Press, New York (TOC).
Romani et al., 2004, "Fatigue in multiple sclerosis: multidimensional assessment and response to symptomatic treatment," Mult. Scler., 10:462-468.
Ropper and Brown (eds), 2005, "Epilepsy and Other Seizure Disorders," Adams and Victor's Principles of Neurology, Eighth Edition. Blacklick, OH: McGraw-Hill Professional, Chapter 16, pp. 271-301.
Rossini et al., 1996, 4-Aminopyridine treatment in chronic progressive multiple sclerosis: a 6 month double-blind placebo-controlled, crossover study by AMIT (American Italian Study). Europ. J. of Neurol., 3 (Suppl 5):91, Abstract P208.
Rossini et al., 2001, "Fatigue in progressive multiple sclerosis: results of a randomized, double-blind, placebo-controlled, crossover trial of oral 4-aminopyridine," Multiple Sclerosis, 7:354-358.
Ruddick et al., 1999, "Selecting relapsing remitting multiple sclerosis patients for treatment: The case of early treatment," J. of Neuroimmunology, 98(1):22-28.
Rupp et al., 1983, "Pharmacokinetics and pharmacodynamics of 4-aminopyridine in anesthetized dogs," J. Pharmacol. Exp. Ther., 225(2):351-354.
Rutecki et al., 1987, "4-Aminopyridine produces epileptiform activity in hippocampus and enhances synaptic excitation and inhibition," J. Neurophysiol., 57(6):1911-1924.
Saade et al., 1982, "Cutaneous receptive field alterations induced by 4-aminopyridine," Brain Res., 232:177-180.
Saade et al., 1985, "Effects of 4-aminopyridine, GABA and bicuculline on cutaneous receptive fields of cat dorsal horn neurons," Brain Res., 344:356-359.
Sadovnick et al., 1991, "Cause of death in patients attending multiple sclerosis clinics," Neurology, 41:1193-1196.
Sander, 2003, "The epidemiology of epilepsy revisited," Curr. Opin. Neurol., 16(2):165-170.
Sanders et al., 1980, "Eaton-Lambert syndrome: a clinical and electrophysiological study of a patient treated with 4-aminopyridine," J. Neurol. Neurosurg. Psychiatry, 43(11):978-985.
Sandyk, 1996, "Weak electromagnetic fields potentiate the effects of 4-aminopyridine in multiple sclerosis," Intern. J. Neuroscience, 85:125-129.
Scheinberg et al., 1980, "Multiple Sclerosis: Earning a living," NY State J. Med., 1395-1400.
Schneider et al., 1997, "Validity and reliability of the Alzheimer's Disease Cooperative Study—Clinical Global Impression of Change," Alzh. Disease Assoc. Dis., 11(Supp12):S22-S32.
Schulz, 2002, "The Landscape and Lexicon of Blinding in Randomized Trials," Ann. Intern. Med. 136:254-259.
Schwid et al., 1997, "Autoimmune hyperthyroidism in patients with multiple sclerosis treated with interferon beta 1-b," Archives of Neurology, 57:1169-1170.
Schwid et al., 1997, "Quantitative assessment of sustained-release 4-aminopyridine for symptomatic treatment of multiple sclerosis," Neurology, 48:817-821.
Schwid et al., 1997, "The measurement of ambulatory impairment in multiple sclerosis," Neurology, 49:1419-1424.
Schwid et al., 1998, "Quantitative measures of motor fatigue in multiple sclerosis: Features of motor dysfunction distinct from weakness," Neurology, 50 (4 Suppl. 4):A210-A211 (P04.036).
Schwid et al., 2000, "Are quantitative functional measures more sensitive to worsening MS than traditional measures?" Neurology, 55(12):1901-1903.

(56) References Cited

OTHER PUBLICATIONS

Schwid et al., 2000, "Subjective fatigue is associated with impaired central motor conduction in MS patients, but motor fatigue is not," Neurology, 54 (7 Supp. 3):A56 (P01.085).
Schwid et al., 2001, "The cost of delaying treatment in multiple sclerosis, what is lost is not regained," Neurology, 56(12):1620.
Schwid et al., 2002, "Quantitative functional measures in MS: What is a reliable change?" Neurology, 58:1294-1296.
Schwid et al., 2004, "Cognitive status after 10 years of prospective evaluation in patients with relapsing multiple sclerosis," Multiple Sclerosis, 10(2):S123 (p. 141).
SEC News Digest Archive: 2003 (http://www.sec.gov/news/digest/digarchives/digarch2003.html; last accessed Nov. 27, 2013).
SEC News Digest, Issue 2003-186, Sep. 30, 2003 (http://www.sec.gov/news/digest/dig093003.txt; last accessed Nov. 27, 2013).
Segal et al., 1991, "Decreased systemic clearance of lorzepam in humans with spinal cord injury," J. Clin. Pharmcol. 31:651-656.
Segal et al., 1997, "4-Aminopyridine improves pulmonary function in quadriplegic humans with longstanding spinal cord injury," Pharmacotherapy, 17(3):415-423.
Segal et al., 1998, "4-Aminopyridine alters gait characteristics and enhances locomotion in spinal cord injured humans," J. Spinal Cord Med., 21(3):200-204.
Segal et al., 1999, "Safety and efficacy of 4-aminopyridine in humans with spinal cord injury: a long term, controlled trial," Phamacother., 19(6):713-723.
Segal et al., 2000, "Absorption characteristics of sustained-release 4-aminopyridine (Fampridine SR) in patients with chronic spinal cord injury," J. Clin. Pharmacol., 40(4):402-409.
Segal et al., 2002, "4-aminopyridine influences heart rate variability in long-standing spinal cord injury," Am. J. Ther., 9(1):29-33.
Semba et al., 1985, "4-aminopyridine induces expansion of cutaneous receptive fields of dorsal horn cells," Brain Res., 343:398-402.
Shaffer, "Ampyra Lower-Dose Post-Market Study Misses Endpoint," Bioworld Today 23(157):1, 4 (Aug. 14, 2012).
Shakespeare et al., "Anti-spasticity agents for multiple sclerosis," Cochrane Database Syst. Rev. 2003;(4):CD001332.
Sharrack et al., 1999, "The Guy's Neurological Disability Scale (GNDS): a new disability measure for multiple sclerosis," Mult. Scler., 5:223-233.
Shealy et al., 1967, "Electrical inhibition of pain by stimulation of the dorsal columns: Preliminary clinical report," Anesth. Analg. 46(4):489-491.
Sherratt et al., 1980, "Effects of 4-aminopyridine on normal and demyelinated mammalian nerve fibres," Nature, 283(5747):570-572.
Shi et al., 1995, "4-Aminopyridine affects conduction in injured spinal cord axons in vitro at clinically relevant concentrations," Society of Neuroscience Abstracts, 21(1-3):1003, (395.3).
Shi et al., 1996, "Compression injury of mammalian spinal-cord in-vitro and the dynamics of action-potential conduction failure," J. of Neurophysiology, 76(3):1572-1580.
Shi et al., 1997, "Conduction block in acute and chronic spinal cord injury: different dose-response characteristics for reversal by 4-aminopyridine," Exp. Neurol., 148:495-501.
Shi et al., 1997, "Differential Effects of Low and High Concentrations of 4-Aminopyridine on Axonal Conduction in Normal and Injured Spinal Cord," Neuroscience, 77(2):553-562.
Shinohara et al., 1982, "Ion-pair high performance liquid chromatographic assay of 4-aminopyridine in serum," J. Chrom. (Biomed Appl), 230:363-372.
Sia et al., 1979, "Effects of the Analeptic Drug, 4-Aminopyridine, upon Post-operative Respiratory Depression in Patients," Acta Anesth. Belg., 30(Suppl):195-199.
Sia et al., 1981, "4-Aminopyridine reversal of fentanyl-induced respiratory depression in normocapnic and hypercapnic patients," Br. J. Anaesth., 53(4):373-379.
Sia et al., 1981, "Use of 4-aminopyridine to reverse morphine-induced respiratory depression in man," Br. J. Anaesth., 53(8):865-868.
Sia et al., 1982, "An electroencephalographic study of 4-aminopyridine," Anest. Analg., 61(4):354-357.
Siegert et al., 2005, "Depression in multiple sclerosis: a review," J. Neurol. Neurosurg. Psychiatry, 76:469-475.
Slide presentation entitled "Protocol No. DER-401 Top Line Results" presented at Webcast and Conference Call by Acorda Therapeutics, Inc. on Aug. 13, 2012.
Smeets et al., 1995, "Severe 4-aminopyridine intoxication in a body-builder," Ned. Tijdschr. Geneesdk., 139(51):2667-2668.
Smith et al., 1982, "Spontaneous and evoked electrical discharges from a central demyelinating lesion," J. Neurol. Sci., 55:39-47.
Smith et al., 2000, "Effects of 4-aminopyridine on demyelinated axons, synapses and muscle tension," Brain, 123:171-184.
Smits et al., 1994, "The effect of 4-aminopyridine on cognitive function in patients with multiple sclerosis: A pilot study," Neurology, 44:1701-1705.
Smits et al., 1994, "The effects of 4-aminopyridine on cognitive function in patients with multiple sclerosis: A pilot study," J. of Neurology, 241:S102 (Abstract. 10).
Snyderman, MD, Nightly News—About Us—msnbc.com, updated Jun. 29, 2009, http://www.msnbc.com/id/14894442 (last accessed Nov. 17, 2010).
Sohn et al., 1981, "Pharmacokinetics and side-effects of 4-aminopyridine. 1981," E. Rugheimer, M. Zindler (eds) Proceedings of the Seventh World Congress of Aneasthesiologists, Hamburg, Sep. 14-21, 1980. Amsterdam: Excerpta Medica, 1981; 224-228.
Solari et al., 2003, "Aminopyridines for symptomatic treatment in multiple sclerosis (Cochrane Review)", in: The Cochrane Library, Issue 2, 2003. Oxford: Update Software. (Date of most recent amendment: Jul. 15, 2002; Date of most recent substantive amendment: Jul. 15, 2002; copyright Update Software Ltd.).
Solari et al., 2004, "Aminopyridines for symptomatic treatment in multiple sclerosis." Cochrane Database of Systematic Reviews 2002, Issue 4. (Date edited: Oct. 11, 2004; Date of most recent substantive amendment: Jul. 15, 2002).
Spatt et al., 2001, "Epileptic and non-epileptic seizures in multiple sclerosis," J. Neurol., 248:2-9.
Speakers Abstracts from ECTRIMS-ACTRIMS 2002, The joint meeting of the Americas and European Committees for Treatment and Research in Multiple Sclerosis held Sep. 18-21, 2002 at the Baltimore Marriott Waterfront Hotel, in Baltimore, Maryland, USA, available at http://www.mult-sclerosis.org/news/Oct2002/ACTRIMSECTRIMS2002SpeakersAbstracts.html (last accessed Aug. 16, 2014).
Spyker et al., 1980, "Poisoning with 4-Aminopyridine: Report of Three Cases," Clinical Toxicology, 16(4):487-497.
Stefoski et al., 1987, "4-Aminopyridine Improves Clinical Signs in Multiple Sclerosis," Ann. Neurol, 21:71-77.
Stefoski et al., 1991, "4-Aminopyridine in multiple sclerosis: Prolonged administration," Neurology, 41:1344-1348.
Stenager et al., 1992, "Suicide and multiple sclerosis: an epidemiological investigation," J. of Neurol. Neurosurg. Psychiatry, 55:542-545.
Stork et al., 1994, "Characterization of 4-aminopyridine in overdose," Clin. Toxicol., 32(5):583-587.
Stoyanov et al., 1976, "Clinical Electromyomechanographic and Electromyographic Studies in Decurarization with Pymadine," Anaesth. Resus Intern. Ther., 4(2):139-142.
Striano et al., 2003, "Epileptic seizures in multiple sclerosis: clinical and EEG correlations," Neurol. Sci., 24:322-328.
Strupp et al., 2004, "Treatment of episodic ataxia type 2 with the potassium channel blocker 4-aminopyridine," Neurology, 62(9):1623-1625.
Stuhmer et al., 1989, "Molecular basis of functional diversity of voltage-gated potassium channels in mammalian brain," EMBO J., 8(11):3235-3244.
Sugimura et al., 1982, "Metabolic aspects of the comutagenic action of norharman," Adv. Exper. Med. Biology, 136:1011-1025.

(56) References Cited

OTHER PUBLICATIONS

Swingler et al., 1992, "The morbidity of multiple sclerosis," Q. J. Med., New Series, 83(300):325-337.
Tapia et al., 1985, "Mechanism of the calcium-dependent stimulation of transmitter releaslse by 4-aminopyridine in synaptosomes," Brain Res., 361:373-382.
Targ et al., 1985, "4-Aminopyridine leads to restoration of conduction in demyelinated rat sciatic nerve," Brain Res., 328(2):358-361.
Targ et al., 1986, "Action potential characteristics of demyelinated rat sciatic nerve following application of 4-aminopyridine," Brain Res. 363:1-9.
Tasker, 1990, "Pain resulting from central nervous system pathology (Central Pain)," The Management of Pain, vol. 1, Bonica ed., Lee and Febiger:Philadelphia, pp. 264-283.
Ter Wee et al., 1985 "4-Aminopyridine and haemodialysis in the treatment of verapamil intoxication," Human Toxicol., 4(3):327-329.
Thesleff, 1980, "Aminopyridines and synaptic transmission," Neuroscience, 5:1413-1419.
Tim et al., 1998, "Lambert-Eaton myasthenic syndrome (LEMS): clinical and electrodiagnostic features and response to therapy in 59 patients," Ann. NY Acad. Sci., 841:823-826.
Tim et al., 2000, "Lambert-Eaton myasthenic syndrome: electrodiagnostic findings and response to treatment," Neurology, 54:2176-2178.
Transcript of Webcast and Conference Call by Acorda Therapeutics, Inc. on Aug. 13, 2012.
Traykov et al., 2001, "Therapeutic Efficacy of Galanthamine and 4-Aminopyridine on Cognitive Deficit in Patients With Multiple Sclerosis," Pharmacol. Toxicol. 89(Suppl. 1): Abstract 551.
Truyen et al., 1996, "Magnetic resonance imaging of epilepsy in multiple sclerosis: a case control study. Implications for treatment trials with 4-aminopyridine," Mult. Scler., 1(4):213-217.
TYSABRI® (natalizumab), Biogen Idec Inc. and Elan Pharmaceuticals Inc., Prescribing Information, Jul. 2010. http://www.tysabri.com/en_US/tysb/site/pdfs/TYSABRI-pi.pdf (last accessed Nov. 3, 2010) (pp. 1-25).
Uges et al., 1981, "4-aminopyridine; analysis of the substance and a method for the preparation of a solution for injection in man," Pharm Acta Helv., 56(6):158-162.
Uges et al., 1981, "Liquid-chromatographic determination of 4-aminopyridine in serum, saliva, and urine," Clinical Chemistry, 27(3):437-440.
Uges et al., 1982, "4-Aminopyridine kinetics," Clin. Pharmacol. Ther., 31(5):587-593.
Uges et al., 1982, "4-aminopyridine Tablets; a Method for the Preparation in-vitro and in-vivo Studies," Pham. Acta. Helv. 57, Nr. 4, 122-128.
Uges et al., 1984, "Treatment of 4-aminopyridine-poisoning after oral overdoses; a proposal," Pharm. Acta Helv., 59:172-176.
Uges, 1982, "4-aminopyridine: Clinical Pharmaceutical, Pharmacological and Toxicological Aspect" Abstract of Thesis, Groningen State University, Pharmazeutisch Weekblad Scientific Edition 5, 256-257.
Uges, 1982, "4-aminopyridine: Clinical Pharmaceutical, Pharmacological and Toxicological Aspect," Thesis, Groningen State University, The Netherlands.
US Food and Drug Administration, For Consumers, Fast Track, Accelerated Approval and Priority Review, http://fda.gov/forconsumers/byaudience/forpatientadvocates/speedingaccesstoimportantnewtherapies/ucm128291.htm (last accessed Nov. 12, 2010).
van der Bruggen et al., 2001, "Randomized trial of 4-aminopyridine in patients with chronic incomplete spinal cord injury," J. Neurol., 248(8):665-671.
van der Horst et al., 1992, "Determination of 4-aminopyridine in serum by solid-phase extraction and high-performance liquid chromatography," J. of Chromatography, 574:166-169.
van Diemen et al., 1992, "Increased visual impairment after exercise (Uhthoff's phenomenon) in multiple sclerosis: therapeutic possibilities," Eur. Neurol., 32(4):231-234.
van Diemen et al., 1992, "The Effect of 4-Aminopyridine on Clinical Signs in Multiple Sclerosis: A Randomized, Placebo-Controlled, Double-Blind, Cross-over Study," Ann. Neurol., 32(2):123-130.
Van Diemen et al., 1993, "4-Aminopyridine in Patients with Multiple Sclerosis: Dosage and Serum Level Related to Efficacy and Safety," Clin. Neuropharm., 16(3):195-204.
van Diemen et al., 1993, "4-Aminopyridine induces functional improvement in multiple sclerosis patients: a neurophysiological study," J. of Neurological Sciences, 116:220-226.
Van Heeringen, 2003, "Understanding the suicidal brain," Br. J. Psychiatry, 184:282-284.
Velez et al., 2003, "Opisthotonic posturing with neuromuscular irritability attributable to 4-aminopyridine ingestion by a healthy pediatric patient," Pediatrics, 111:e82-e84.
Voskuyl et al., 1985, "Spontaneous epileptiform discharges in hippocampal slices induced by 4-aminopyridine," Brain Research, 342(1):54-66.
Wagoner et al., 1990, "Aminopyridines block an inactivating potassium current having slow recovery kinetic," Biophys. J., 58:1481-1489.
Wakabayashi et al., 1982, "Comutagneic effect of norharman with aminopyridine derivatives," Mutation Research, 105:205-210.
Walker, 2002, "A. Common Statistical Methods for Clinical Research with SAS® Examples," Second Edition, 2002, Cary, NC: SAS Institute Inc., p. 32.
Waxman et al., 1984, "Impulse conduction in inhomogeneous axons: Effects of variation in voltage-sensitive Ionic conductances of invasion of demyelinated axon segments and preterminal fibers," Brain Res., 294:111-122.
Waxman et al., 1985, "Ligature-induced injury in peripheral nerve: Electrophysiological observations on changes in action potential characteristics following blockade of potassium conductance," Muscl. Nerve, 8:85-92.
Waxman et al., 1993, "Molecular dissection of the myelinated axon," Ann. Neurol., 33(2):121-136.
Waxman, 1982, "Membranes, myelin, and the pathophysiology of multiple sclerosis," N. Engl. J. Med. 306(25):1529-1533.
Wesseling et al., 1984, "Effects of 4-Aminopyridine in Elderly Patients with Alzheimer's Disease." New England J. of Medicine, vol. 310(15):988-989.
Wirtavuori et al., 1984, "Antagonism of d-tubocurarine-induced neuromuscular blockade with a mixture of 4-aminopyridine and neostigmine in man," Can. Anaesth. Soc. J., 31(6):624-630.
Wolfe et al., 2001, "Effects of 4-aminopyridine on motor evoked potentials in patients with spinal cord injury: a double-blinded, placebo-controlled crossover trial," J. Neurotrauma, 18(8):757-771.
Wolinsky et al., 2004, "The PROMiSe trial: baseline data review and progress report" Multiple Sclerosis, 10:S65-S72.
Wolinsky et al., 2007, "Glatiramer acetate in primary progressive multiple sclerosis: results of a multinational, multicenter, double-blind, placebo-controlled trial," Ann Neurol., 61:14-24.
Xu et al., 1992 "Chronic pain-related syndrome in rats after ischemic spinal cord lesion: a possible animal model for pain in patients with spinal cord injury," Pain, 48:279-290.
Yeh et al., 1976, "Dynamics of aminopyridine block of potassium channels in squid axon membrane," J. Gen. Physiol. , 68:519-535.
Yeh et al., 1976, "Interactions of aminopyridines with potassium channels of squid axon membranes," Biophys. J., 16:77-81.
Zorzon et al., 2001, "Depression and anxiety in multiple sclerosis. A clinical and MRI study in 95 subjects," J. Neurol., 248:416-421.
Written Submission by Synthon B.V., filed Dec. 23, 2015, in Opposition to European Patent No. EP 2377536.
Center for Drug Evaluation and Research, Application No. 22-250s000, Medical Review, Fampridine Sustained Release (4-aminopyridine), by Kachi Illoh, MD, MPH, completed Dec. 10, 2009.

(56) References Cited

OTHER PUBLICATIONS

ClinicalTrials.gov, "Efficacy and Safety of Prolonged-Release Fampridine in Participants With Multiple Sclerosis (Enhance)," NCT02219932, by Biogen, first received Aug. 18, 2014.
Declaration by Professor S. H. Heisterkamp, dated Dec. 23, 2015, with Curriculum Vitae.
European Medicines Agency, Assessment report, Fampyra, Committee for Medicinal Products for Human Use, dated Jun. 23, 2011.
European Medicines Agency, Performance of the Agency's scientific procedures: 2011 report for medicinal products for human use, Management Board meeting Mar. 22, 2012, Executive summary, dated Mar. 29, 2012.
Hobart et al., 2013, "Timed 25-Foot Walk," Neurology 80:1509-1517.
Hobart et al., 2010, "Prolonged-release fampridine for multiple sclerosis: was the effect on walking ability clinically significant?" Multiple Sclerosis 2010, 16:S172, Abstract P509.
Motl et al., 2014, "Validity of Minimal Clinically Important Difference Values for the Multiple Sclerosis Walking Scale-12?" Eur. Neurol. 71:196-202.
Piantadosi, 2005, "Estimating Clinical Effects," in *Clinical Trials: A Methodologic Perspective*, a John Wiley & Sons, Inc. publication (Balding et al., eds.), Chapter 16, pp. 409-451.
Second Declaration of Gerrit Voortman, dated Dec. 23, 2015.
Third Declaration of Gerrit Voortman, dated Feb. 4, 2016.
U.S. Food and Drug Administration, "NDA 22-250: Fampridine AC Backgrounder," Memorandum, from E. Bastings, through R. Katz, dated Sep. 16, 2009.
Yapundich et al., 2015, "Evaluation of Dalfampridine Extended Release 5 and 10 mg in Multiple Sclerosis," Int. J. MS Care 17: 138-145.
Written Submission by Actavis Group PTC ehf, filed Dec. 23, 2015, in Opposition to European Patent No. EP 2377536.
Written Submission by Synthon B.V., filed Feb. 8, 2016, in Opposition to European Patent No. EP 2377536.
U.S. Securities and Exchange Commission, Acorda Therapeutics, Inc. Form 10-K Annual Report for the year ended Dec. 31, 2005, table of contents and select pages.
ACTRIMS-ECTRIMS, Final Program, Abstract Listing and Meeting Information, 7$^{th}$ Annual Meeting for the Americas Committee for Treatment and Research in Multiple Sclerosis, Sep. 18-21, 2002.
Curriculum Vitae of Timothy L. Vollmer, M.D., dated Feb. 27, 2015.
Third Party Observation filed Aug. 11, 2015 in European Application No. 20110160247, European Patent No. EP 2377536.
Third Party Observation filed Sep. 2, 2015 in European Application No. 05732613, EP Patent No. 1732548.
Declaration of Dr. Andrew Blight executed Sep. 15, 2014, and its Exhibit A (Curriculum Vitae of Dr. Blight), filed in connection with EP Application No. EP 05732613.4, EP Patent No. EP 1732548.
Opposition to EP 2377536 B1, Communication from the European Patent Office dated Jul. 20, 2015 (Summons to attend oral proceedings pursuant to Rule 115(1) EPC with Preliminary Non-binding Opinion).
Opposition Decision issued by the EPO on Apr. 6, 2016, accompanied by Minutes of the Oral Proceeding and Claim Requests, for European Patent, No. 2377536.
Appeal Response by Opponent Synthon B.V., filed Dec. 27, 2016 in the Appeal of the Opposition Decision in EP Application No. 057326134, EP Patent No. 1732548 ("Appeal Response").
List of References filed in U.S. Appl. No. 11/102,559, filed Jul. 26, 2012, and IDS Transmital Letter that accompanied the List of References filed in U.S. Appl. No. 11/102,559, filed Jul. 26, 2012.
Antler Declaration, executed on Aug. 15, 2016, with Exhibits A-C.
Van Horn Declaration, executed on Aug. 13, 2016, with Exhibits A-H.
Cross Declaration, executed on Aug. 15, 2016, with Exhibit A.
Vollmer Declaration, executed on Aug. 15, 2016, with Exhibit A.
Hartung Declaration, executed on Aug. 15, 2016, with Exhibit A.
Appeal Response by Opponent Synthon B.V., filed Dec. 27, 2016 in the Appeal of the Opposition Decision in EP Application No. 111602470, EP Patent No. 2377536.
Appeal Response by Opponent Actavis, filed Jan. 3, 2017 in the Appeal of the Opposition Decision in EP Application No. 111602470, EP Patent No. 2377536.
Plaintiff's Expert Report dated Mar. 4, 2014, Request for an Administrative Declaration of Invalidation in connection with Mexican Patent No. 293798, *Nafar Laboratorios, S.A. de C.V.* vs *Acorda Therapeutics, Inc.*, filed May 22, 2013 at Mexican Institute of Industrial Property (with English translation).
Plaintiff's Observations on Third-Party Expert Report dated Jan. 27, 2015, Request for an Administrative Declaration of Invalidation in connection with Mexican Patent No. 293798, *Nafar Laboratorios, S.A. de C.V.* vs *Acorda Therapeutics, Inc.*, filed May 22, 2013 at Mexican Institute of Industrial Property (with English translation).
Third-Party Expert Report dated Dec. 3, 2014, Request for an Administrative Declaration of Invalidation in connection with Mexican Patent No. 293798, *Nafar Laboratorios, S.A. de C.V.* vs *Acorda Therapeutics, Inc.*, filed May 22, 2013 at Mexican Institute of Industrial Property (with English translation).
Request for Patent Term Extension Under 35 U.S.C. 156 filed Mar. 17, 2010 for U.S. Pat. No. 5,540,938, issued Jul. 30, 1996.
Request for Patent Term Extension Under 35 U.S.C. 156 filed Mar. 17, 2010 for U.S. Pat. No. 5,370,879, issued Jun. 12, 1994.
Notice Letter and Detailed Factual and Legal Bases for Accord Healthcare, Inc.'s Paragraph IV Certification dated Jul. 7, 2014.
Notice Letter and Detailed Factual and Legal Bases for Actavis Laboratories FL, Inc.'s Paragraph IV Certification dated Jun. 24, 2014.
Notice Letter and Detailed Factual and Legal Bases for Alkem Laboratories Ltd.'s Paragraph IV Certification dated Jul. 2, 2014.
Notice Letter and Detailed Factual and Legal Bases for Apotex Inc.'s Paragraph IV Certification dated Jul. 11, 2014.
Notice Letter and Detailed Factual and Legal Bases for Apotex Inc.'s Paragraph IV Certification dated Jul. 17, 2014.
Notice Letter and Detailed Factual and Legal Bases for Apotex, Inc.'s Paragraph IV Certification dated Jul. 13, 2014.
Notice Letter and Detailed Factual and Legal Bases for Aurobindo Pharma Ltd.'s Paragraph IV Certification dated Jun. 26, 2014.
Notice Letter and Detailed Factual and Legal Bases for Mylan Pharmaceuticals Inc.'s Paragraph IV Certification dated Jul. 9, 2014.
Notice Letter and Detailed Factual and Legal Bases for Roxane Laboratories, Inc.'s Paragraph IV Certification dated Jul. 1, 2014.
Notice Letter and Detailed Factual and Legal Bases for Teva Pharmaceuticals USA Inc.'s Paragraph IV Certification dated Jul. 11, 2014.
Notice Letter and Detailed Factual and Legal Bases for Actavis Laboratories FL, Inc.'s Paragraph IV Certification dated Jan. 12, 2015.
Notice Letter and Detailed Factual and Legal Bases for Sun Pharmaceutical Industries Limited's Paragraph IV Certification dated May 5, 2015.
Notice Letter and Detailed Factual and Legal Bases for Par Pharmaceutical, Inc.'s Paragraph IV Certification dated Sep. 10, 2015.
Complaint filed Aug. 22, 2014, *Acorda Therapeutics, Inc.* v. *Mylan Pharmaceuticals Inc.*, Docket No. 1:14-cv-00139 (N.D. W. Va. Aug. 22, 2014).
Complaint filed Jul. 10, 2014, *Acorda Therapeutics Inc.* v. *Aurobindo Pharma Ltd.*, Docket No. 1:14-cv-00909 (D. Del. Jul. 10, 2014).
Complaint filed Jul. 11, 2014, *Acorda Therapeutics Inc.* v. *Alkem Laboratories Ltd.*, Docket No. 1:14-cv-00917 (D. Del. Jul. 11, 2014).
Complaint filed Jul. 14, 2014, *Acorda Therapeutics Inc.* v. *Roxane Laboratories Inc.*, Docket No. 1:14-cv-00922 (D. Del. Jul. 14, 2014).
Complaint filed Jul. 15, 2014, *Acorda Therapeutics Inc.* v. *Accord Healthcare Inc.*, Docket No. 1:14-cv-00932 (D. Del. Jul. 15, 2014).
Complaint filed Jul. 16, 2014, *Acorda Therapeutics Inc.* v. *Mylan Pharmaceuticals Inc.*, Docket No. 1:14-cv-00935 (D. Del. Jul. 16, 2014).

(56) References Cited

OTHER PUBLICATIONS

Complaint filed Jul. 17, 2014, *Acorda Therapeutics Inc.* v. *Teva Pharmaceuticals USA Inc.*, Docket No. 1:14-cv-00941 (D. Del. Jul. 17, 2014).
Complaint filed Jul. 18, 2014, *Acorda Therapeutics Inc.* v. *Apotex Corp.*, Docket No. 1:14-cv-00955 (D. Del. Jul. 18, 2014).
Complaint filed Jul. 7, 2014, *Acorda Therapeutics Inc.* v. *Actavis Laboratories FL Inc.*, Docket No. 1:14-cv-00882 (D. Del. Jul. 7, 2014).
Complaint filed Jan. 23, 2015, *Acorda Therapeutics Inc.v. Actavis Laboratories FL, Inc.*, Docket No. 1:15-cv-00077 (D. Del. Jan. 23, 2015).
Complaint filed May 18, 2015, *Acorda Therapeutics Inc.* v. *Sun Pharmaceutical Industries Limited*, Docket No. 1:15-cv-00391 (D. Del. May 15, 2015).
Complaint filed Sep. 15, 2015, *Acorda Therapeutics Inc.* v. *Par Pharmaceutical Inc.*, Docket No. 1:15-cv-00824 (D. Del. Sep. 15, 2015).
Alkem Laboratories Limited's Answer, Affirmative Defenses, and Counterclaims to Plaintiff's Complaint for Patent Infringement, filed Aug. 1, 2014, *Acorda Therapeutics Inc.* v. *Alkem Laboratories Ltd.*, Docket No. 1:14-cv-00917 (D. Del. Jul. 11, 2014).
Defendant Accord Healthcare, Inc.'s Answer, Separate Defenses, and Counterclaims to Plaintiff's Complaint filed Aug. 19, 2014, *Acorda Therapeutics Inc.* v. *Accord Healthcare Inc.*, Docket No. 1:14-cv-00932 (D. Del. Jul. 15, 2014).
Defendant Roxane Laboratories, Inc's Answer and Affirmative Defenses, filed Aug. 15, 2014, *Acorda Therapeutics Inc.* v. *Roxane Laboratories Inc.*, Docket No. 1:14-cv-00922 (D. Del. Jul. 14, 2014).
Answer, Affirmative Defenses and Counterclaims Aug. 22, 2014, *Acorda Therapeutics Inc.* v. *Apotex Corp.*, Docket No. 1:14-cv-00955 (D. Del. Jul. 18, 2014).
Answer, Affirmative Defenses and Counterclaims filed Aug. 22, 2014, *Acorda Therapeutics Inc.* v. *Actavis Laboratories FL Inc.*, Docket No. 1:14-cv-00882 (D. Del. Jul. 7, 2014).
Answer, Affirmative Defenses and Counterclaims filed Aug. 22, 2014, *Acorda Therapeutics Inc.* v. *Teva Pharmaceuticals USA Inc.*, Docket No. 1:14-cv-00941 (D. Del. Jul. 17, 2014).
Aurobindo Pharma Ltd. and Aurobindo Pharma U.S.A., Inc.'s Answer, Affirmative Defenses, and Counterclaims to Plaintiffs' Complaint for Patent Infringement, filed Sep. 23, 2014, *Acorda Therapeutics Inc.* v. *Aurobindo Pharma Ltd.*, Docket No. 1:14-cv-00909 (D. Del. Jul. 10, 2014).
Answer to Complaint filed Feb. 17, 2015, *Acorda Therapeutics Inc.v. Actavis Laboratories FL, Inc.*, Docket No. 1:15-cv-00077 (D. Del. Jan. 23, 2015).
Answer, Defenses and Counterclaims of Mylan Pharmaceuticals Inc. filed Feb. 20, 2015, *Acorda Therapeutics Inc.* v. *Mylan Pharmaceuticals Inc.*, Docket No. 1:14-cv-00935 (D. Del. Jul. 16, 2014).
Answer, Defenses, and Counterclaims of Mylan Pharmaceuticals Inc. and Mylan Inc. filed Jan. 12, 2015, *Acorda Therapeutics, Inc.* v. *Mylan Pharmaceuticals Inc.*, Docket No. 1:14-cv-00139 (N.D. W. Va. Aug. 22, 2014).
Answer, Affirmative Defenses, and Counterclaims filed Jun. 9, 2015, *Acorda Therapeutics Inc.* v. *Sun Pharmaceutical Industries Limited*, Docket No. 1:15-cv-00391 (D. Del. May 15, 2015).
Answer, Separate Defenses and Counterclaims of Par Pharmaceutical, Inc., filed Oct. 7, 2015, *Acorda Therapeutics Inc.* v. *Par Pharmaceutical Inc.*, Docket No. 1:15-cv-00824 (D. Del. Sep. 15, 2015).
Acorda Therapeutics, Inc. and Alkermes Pharma Ireland Limited Answer to the Counterclaims of Alkem Laboratories Ltd. Filed Aug. 22, 2014, *Acorda Therapeutics Inc.* v. *Alkem Laboratories Ltd.*, Docket No. 1:14-cv-00917 (D. Del. Jul. 11, 2014).
Acorda Therapeutics, Inc. and Alkermes Pharma Ireland Limited's Answer to the Counterclaims of Aurobindo Pharma Ltd. and Aurobindo Pharma U.S.A., Inc., filed Oct. 17, 2014, *Acorda Therapeutics Inc.* v. *Aurobindo Pharma Ltd.*, Docket No. 1:14-cv-00909 (D. Del. Jul. 10, 2014).
Acorda Therapeutics, Inc. and Alkermes Pharma Ireland Limited's Answer to the Counterclaims of Accord Healthcare, Inc. filed Sep. 12, 2014, *Acorda Therapeutics Inc.* v. *Accord Healthcare Inc.*, Docket No. 1:14-cv-00932 (D. Del. Jul. 15, 2014).
Acorda Therapeutics, Inc. and Alkermes Pharma Ireland Limited's Answer to the Counterclaims of Actavis Laboratories Fl., Inc., filed Sep. 12, 2014, *Acorda Therapeutics Inc.* v. *Actavis Laboratories FL Inc.*, Docket No. 1:14-cv-00882 (D. Del. Jul. 7, 2014).
Acorda Therapeutics, Inc. and Alkermes Pharma Ireland Limited's Answer to the Counterclaims of Apotex Corp. and Apotex Inc. filed Sep. 12, 2014, *Acorda Therapeutics Inc.* v. *Apotex Corp.*, Docket No. 1:14-cv-00955 (D. Del. Jul. 18, 2014).
Acorda Therapeutics, Inc. and Alkermes Pharma Ireland Limited's Answer to the Counterclaims of Teva Pharmaceuticals USA, Inc. filed Sep. 12, 2014, *Acorda Therapeutics Inc.* v. *Teva Pharmaceuticals USA Inc.*, Docket No. 1:14-cv-00941 (D. Del. Jul. 17, 2014).
Acorda Therapeutics, Inc. and Alkermes Pharma Ireland Limited's Answer to the Counterclaims of Mylan Pharmaceuticals, Inc. filed Feb. 2, 2015, *Acorda Therapeutics, Inc.* v. *Mylan Pharmaceuticals Inc.*, Docket No. 1:14-cv-00139 (N.D. W. Va. Aug. 22, 2014).
Acorda Therapeutics, Inc. and Alkermes Pharma Ireland Limited's Answer to the Counterclaims of Actavis Laboratories FL, Inc. filed Mar. 10, 2015, *Acorda Therapeutics Inc.v. Actavis Laboratories FL, Inc.*, Docket No. 1:15-cv-00077 (D. Del. Jan. 23, 2015).
Acorda Therapeutics, Inc. and Alkermes Pharma Ireland Limited's Answer to the Counterclaims of Mylan Pharmaceuticals Inc. filed Mar. 10, 2015, *Acorda Therapeutics Inc.* v. *Mylan Pharmaceuticals Inc.*, Docket No. 1:14-cv-00935 (D. Del. Jul. 16, 2014).
Acorda's Answer to Sun's Counterclaims, filed Jul. 6, 2015, *Acorda Therapeutics Inc.* v. *Sun Pharmaceutical Industries Limited*, Docket No. 1:15-cv-00391 (D. Del. May 15, 2015).
Acorda Therapeutics Inc.'s Answer to the Counterclaims of Par Pharmaceutical, Inc., filed Nov. 2, 2015, *Acorda Therapeutics Inc.* v. *Par Pharmaceutical Inc.*, Docket No. 1:15-cv-00824 (D. Del. Sep. 15, 2015).
Consent Judgment, filed Oct. 29, 2015, *Acorda Therapeutics Inc.* v. *Sun Pharmaceutical Industries Limited*, Docket No. 1:15-cv-00391.
Consent Judgment, filed Dec. 15, 2015, *Acorda Therapeutics, Inc., et al.* v. *Aurobindo Pharma Ltd., et al.*, Docket No. 1:14-cv-00909 (also filed in consolidated Docket No. 1:14-cv-00882).
Corrected Consent Judgment, filed Dec. 22, 2015, *Acorda Therapeutics, Inc., et al.* v. *Aurobindo Pharma Ltd., et al.*, Docket No. 1:14-cv-00909 (also filed in consolidated Docket No. 1:14-cv-00882).
Consent Judgment, filed Jan. 21, 2016 in *Acorda Therapeutics, Inc.* v. *Par Pharmaceutical Inc.*, C.A. No. 15-824 (LPS).
Consent Judgment, filed Mar. 28, 2017, *Acorda Therapeutics Inc.* v. *Apotex Corp.*, Docket No. 1:14-cv-00955 (also filed in consolidated Docket No. 1:14-cv-00882).
Defendants' Joint Initial Invalidity Contentions Pursuant to the Default Standard for Discovery filed Jul. 29, 2015 in *Acorda Therapeutics, Inc.* v. *Actavis Laboratories FL, Inc.*, C.A. No. 1:14-cv-00882-LPS (Consolidated).
Defendants' Amended Joint Initial Invalidity Contentions Pursuant to the Default Standard for Discovery filed Aug. 26, 2015 in *Acorda Therapeutics, Inc.* v. *Actavis Laboratories FL, Inc.*, C.A. No. 1:14-cv-00882-LPS (Consolidated).
"Elan's Mar. 3, 1994 Response filed in the '651 application," i.e., U.S. Appl. No. 08/073,651 (as cited in Defendants' Amended Joint Initial Invalidity Contentions Pursuant to the Default Standard for Discovery filed Aug. 26, 2015).
"Elan's Aug. 16, 1993 Preliminary Amendment filed in the '651 application," i.e., U.S. Appl. No. 08/073,651 (as cited in Defendants' Amended Joint Initial Invalidity Contentions Pursuant to The Default Standard for Discovery filed Aug. 26, 2015).
"Elan's Feb. 24, 1995 Letter filed in EP '186," i.e., European Application No. 0484186 A1 (as cited in Defendants' Amended Joint Initial Invalidity Contentions Pursuant to The Default Standard for Discovery filed Aug. 26, 2015).
"Elan's Feb. 9, 1996 Letter filed in EP '186," i.e., European Application No. 0484186 A1 (as cited in Defendants' Amended Joint Initial Invalidity Contentions Pursuant to the Default Standard for Discovery filed Aug. 26, 2015).

(56) References Cited

OTHER PUBLICATIONS

"Elan's Sep. 3, 1992 Amendment filed in the '400 application," i.e., U.S. Appl. No. 07/786,400 (as cited in Defendants' Amended Joint Initial Invalidity Contentions Pursuant to The Default Standard for Discovery filed Aug. 26, 2015).

Supplemental Amendment and Response to Non-Final Office Action dated Apr. 2, 2009, filed in U.S. Appl. No. 11/010,828 (cited in Defendants' Amended Joint Initial Invalidity Contentions Pursuant to The Default Standard for Discovery filed Aug. 26, 2015).

AMPYRA® (dalfampridine), Acorda Therapeutics, Inc., Prescribing Information, dated Jan. 2010 (cited in Defendants' Amended Joint Initial Invalidity Contentions Pursuant to The Default Standard for Discovery filed Aug. 26, 2015).

Plaintiffs' Opening Claim Construction Brief, filed Nov. 23, 2015 in *Acorda Therapeutics, Inc., et al. v. Aurobindo Pharma Ltd., et al.*, C.A. No. 14-00882-LPS (Consolidated).

Joint Claim Construction Chart with Exhibits D1-D3 and p.1-p. 7, filed Oct. 19, 2015 in *Acorda Therapeutics, Inc. v. Actavis Laboratories FL, Inc.*, Docket No. 14-cv-00882-LPS (Consolidated).

Declaration of Arthur H. Kibbe, Ph.D. in Support of Defendants' Opening Claim Construction Brief with Exhibit AK-1, filed Nov. 23, 2015 in *Acorda Therapeutics, Inc., et al. v. Aurobindo Pharma Ltd., et al.*, C.A. No. 14-00882-LPS (Consolidated).

Declaration of Daniel P. DiNapoli in Support of Plaintiffs' Opening Claim Construction Brief with Exhibits A-F, filed Nov. 23, 2015 in *Acorda Therapeutics, Inc., et al. v. Aurobindo Pharma Ltd., et al.*, C.A. No. 14-00882-LPS (Consolidated).

Declaration of Stephen J. Peroutka, M.D., Ph.D. In Support of Defendants' Opening Claim Construction Brief with Exhibits SP-1 and SP-2, filed Nov. 23, 2015 in *Acorda Therapeutics, Inc., et al. v. Aurobindo Pharma Ltd., et al.*, C.A. No. 14-00882-LPS (Consolidated).

Defendants' Opening Claim Construction Brief, filed Nov. 23, 2015 in *Acorda Therapeutics, Inc., et al. v. Aurobindo Pharma Ltd., et al.*, C.A. No. 14-00882-LPS (Consolidated).

Exhibit A of Defendants' Opening Claim Construction Brief—U.S. Pat. No. 1,879,324 (filed Sep. 27, 1932).

Exhibit B of Defendants' Opening Claim Construction Brief—Vizi, 1977, "The Effect of 4-Aminopyridine on Acetylcholine Release," J. Neural Transmission 41:265-274.

Exhibit C of Defendants' Opening Claim Construction Brief—Lundh, 1978, "Effects of 4-Aminopyridine on Neuromuscular Transmission," Brain Research 153:307-318.

Exhibit D of Defendants' Opening Claim Construction Brief—Sherratt, 1980, "Effects of 4-aminopyridine on normal demyelinated mammalian nerve fibres," Nature 283: 570-572.

Exhibit E of Defendants' Opening Claim Construction Brief—Lundh, 1977, "4-Aminopyridine—a new drug tested in the treatment of Eaton-Lambert syndrome," Journal of Neurology, Neurosurgery, and Psychiatry 40:1109-1112.

Exhibit F of Defendants' Opening Claim Construction Brief—Lundh, 1979, "Effects of 4-ammopyridm in myasthenia gravis," Journal of Neurology, Neurosurgery, and Psychiatry 42:171-175.

Exhibit G of Defendants' Opening Claim Construction Brief—"2012 ICD-9-CM Diagnosis Code 719.7: Difficulty in walking," available at http://www.icd9data.com/2012/Volume1/710-739/710-719/719/719.7.htm.

Exhibit H of Defendants' Opening Claim Construction Brief—"2012 ICD-9-CM Diagnosis Code 781.2: Abnormality of gait," available at http://www.icd9data.cona/2012/Volume1/780-799/780-789/781/781.2.htm.

Exhibit I of Defendants' Opening Claim Construction Brief—Pearson, 2004, "Quantification of walking mobility in neurological disorders," Q. J. Med. 97:463-475.

Exhibit J of Defendants' Opening Claim Construction Brief—Bethoux, 2011, "Evaluating Walking in Patients with Multiple Sclerosis," Int. J. MS Care 13:4-14.

Exhibit K of Defendants' Opening Claim Construction Brief—Longer et al., 1990, "Sustained-Release Drug Delivery Systems," Remington's Pharmaceutical Sciences, A. Gennaro, Ed., Mack Publishing Company, Easton, PA, p. 1677.

Exhibit L of Defendants' Opening Claim Construction Brief—Longer et al., 1990, "Sustained-Release Drug Delivery Systems," Remington's Pharmaceutical Sciences, A. Gennaro, Ed., Mack Publishing Company, Easton, PA, pp. 1681-1684.

Exhibit M of Defendants' Opening Claim Construction Brief—Alberts et al., 1989, "Nerve Cells Communicate Chemically at Synapses," Molecular Biology of the Cell, M. Robertson, Ed., Garland Publishing, Inc., New York & London, p. 1062.

Exhibit N of Defendants' Opening Claim Construction Brief—Jul. 20, 1995 Amendment from the prosecution history of U.S. Appl. No. 08/328,165 (U.S. Pat. No. 5,540,938).

Exhibit O of Defendants' Opening Claim Construction Brief—Sep. 3, 1992 Amendment from the prosecution history of U.S. Appl. No. 07/786,400.

Exhibit P of Defendants' Opening Claim Construction Brief—Harrington, 1987, "The clinical use of cerebrospinal fluid studies in demyelinating neurological diseases," Postgraduate Medical Journal 63:735-740.

Exhibit Q of Defendants' Opening Claim Construction Brief—the filing of U.S. Appl. No. 08/328,165 (dated Oct. 21, 1994).

Exhibit R of Defendants' Opening Claim Construction Brief—Nov. 24, 2010 Amendment from the prosecution history of U.S. Appl. No. 11/010,828 (now U.S. Pat. No. 8,007,826).

Exhibit S of Defendants' Opening Claim Construction Brief—Sheiner, 1989, "Study designs for dose-ranging," Clin. Pharmacol. Ther. 46:63-77.

Exhibit T of Defendants' Opening Claim Construction Brief—Lemelin, 1989, "Does Antihypertensive Therapy Need to be Life-Long?" Can. Fam. Physician 35:1829-1831.

Exhibit U of Defendants' Opening Claim Construction Brief—Mar. 17, 2011 Amendment from the prosecution history of U.S. Appl. No. 11/102,559 (now U.S. Pat. No. 8,354,437).

Exhibit V of Defendants' Opening Claim Construction Brief—International Patent No. WO 2010/093838 A1 (published Aug. 19, 2010).

Defendants' Answering Claim Construction Brief, filed Jan. 15, 2016 in *Acorda Therapeutics, Inc., et al. v. Alkem Laboratories Ltd., et al.*, C.A. No. 14-00882-LPS (Consolidated).

Plaintiffs' Reply Claim Construction Brief, filed Jan. 15, 2016 in *Acorda Therapeutics, Inc., et al. v. Alkem Laboratories Ltd., et al.*, C.A. No. 14-00882-LPS (Consolidated).

Stipulation Regarding Claim Construction, filed Mar. 4, 2016 in *Acorda Therapeutics, Inc., et al. v. Alkem Laboratories Ltd., et al.*, C.A. No. 14-00882-LPS (Consolidated).

Letter to Chief Judge Stark, dated Mar. 4, 2016, re: *Acorda Therapeutics, Inc., et al. v. Alkem Laboratories Ltd., et al.*, C.A. No. 14-00882-LPS (Consolidated).

Stipulation Regarding Claim Construction, filed Mar. 9, 2016 in *Acorda Therapeutics, Inc., et al. v. Alkem Laboratories Ltd., et al.*, C.A. No. 14-00882-LPS (Consolidated).

Memorandum Opinion, filed Mar. 16, 2016 in *Acorda Therapeutics, Inc., et al. v. Alkem Laboratories Ltd., et al.*, C.A. No. 14-00882-LPS.

Order, filed Mar. 16, 2016, in *Acorda Therapeutics, Inc., et al. v. Alkem Laboratories Ltd., et al.*, C.A. No. 14-00882-LPS (Consolidated).

Consent Judgement, filed Aug. 5, 2016 in *Acorda Therapeutics, Inc. and Alkermes Pharma Ireland Limited v. Alkem Laboratories Ltd. and Ascend laboratories, LLC*, C.A. No. 14-00882-LPS (Consolidated).

Consent Judgement, filed Aug. 18, 2016 in *Acorda Therapeutics, Inc. and Alkermes Pharma Ireland Limited v. Accord Healthcare, Inc.*, C.A. No. 14-00882-LPS (Consolidated).

Plaintiffs' Proposed Findings of Fact, filed Sep. 30, 2016 in *Acorda Therapeutics, Inc. v. Roxane Laboratories, Inc. et al.*, C.A. No. 14-00882 (LPS) (Consolidated).

Defendants' Proposed Findings of Fact, filed Sep. 30, 2016 in *Acorda Therapeutics, Inc. v. Roxane Laboratories, Inc. et al.*, C.A. No. 14-00882 (LPS) (Consolidated).

(56) References Cited

OTHER PUBLICATIONS

Reply Expert Report of Dr. Arthur H. Kibbe, filed May 20, 2016 in *Acorda Therapeutics, Inc.* v. *Alkem Laboratories , Ltd. et al.*, C.A. No. 14-00882-LPS (Consolidated).
Defendants' Opening Post-Trial Brief, filed Oct. 14, 2016 in *Acorda Therapeutics, Inc.* v. *Roxane Laboratories, Inc. et al.*, C.A. No. 14-00882 (LPS) (Consolidated).
Plaintiffs' Post-Trial Answering Brief on Validity and Opening Brief on Secondary Considerations of Nonobviousness, filed Oct. 28, 2016 in *Acorda Therapeutics, Inc.* v. *Roxane Laboratories, Inc. et al.*, C.A. No. 14-00882 (LPS) (Consolidated).
Defendants' Post-Trial Reply Brief, filed Nov. 3, 2016 in *Acorda Therapeutics, Inc.* v. *Roxane Laboratories, Inc. et al.*, C.A. No. 14-00882 (LPS) (Consolidated).
Plaintiffs' Post-Trial Sur-Reply Brief on Secondary Considerations of Nonobviousness, filed Nov. 10, 2016 in *Acorda Therapeutics, Inc.* v. *Roxane Laboratories, Inc. et al.*, C.A. No. 14-00882 (LPS) (Consolidated).
Trial Transcript—vol. A, Before Hon. Leonard Stark, Sep. 19, 2016, Wilmington, Del., *Acorda Therapeutics, Inc., et al.* v. *Roxane Laboratories, Inc., et al.*, Docket No. 14-882-LPS (consolidated).
Trial Transcript—vol. B, Before Hon. Leonard Stark, Sep. 20, 2016, Wilmington, Del., *Acorda Therapeutics, Inc., et al.* v. *Roxane Laboratories, Inc., et al.*, Docket No. 14-882-LPS (consolidated).
Trial Transcript—vol. C, Before Hon. Leonard Stark, Sep. 21, 2016, Wilmington, Del., *Acorda Therapeutics, Inc., et al.* v. *Roxane Laboratories, Inc., et al.*, Docket No. 14-882-LPS (consolidated).
Trial Transcript—vol. D, Before Hon. Leonard Stark, Sep. 23, 2016, Wilmington, Del., *Acorda Therapeutics, Inc., et al.* v. *Roxane Laboratories, Inc., et al.*, Docket No. 14-882-LPS (consolidated).
Court Order, entered Mar. 31, 2017, in *Acorda Therapeutics, Inc., et al.* v. *Roxane Laboratories, Inc., et al.*, C.A. No. 14-882-LPS (Consolidated).
Memorandum Opinion, entered Mar. 31, 2017, in *Acorda Therapeutics, Inc., et al.* v. *Roxane Laboratories, Inc., et al.*, C.A. No. 14-882-LPS (Consolidated).
Final Judgment, dated Apr. 24, 2017, in *Acorda Therapeutics, Inc.* v. *Roxane Laboratories Inc., et al.*, C.A. No. 14-882-LPS (Consolidated).
Petition for Inter Partes Review of U.S. Pat. No. 8,663,685 filed Feb. 10, 2015 by the Coalition for Affordable Drugs (ADROCA) LLC ("ADROCA '685 IPR") (IPR2015-00720).
ADROCA '685 IPR, Exhibit 1001—U.S. Pat. No. 8,663,685 to Andrew R. Blight et al., titled "Sustained Release Aminopyridine Composition".
ADROCA '685 IPR, Exhibit 1002—U.S. Pat. No. 8,007,826 to Andrew R. Blight et al., titled "Sustained Release Aminopyridine Composition".
ADROCA '685 IPR, Exhibit 1005—Jones et al., 1983, "Effects of 4-Aminopyridine in Patients with Multiple Sclerosis," J. Neurol Sci., 60:353-362.
ADROCA '685 IPR, Exhibit 1006—Stefoski et al., 1991, "4-Aminopyridine in multiple sclerosis: Prolonged administration," Neurology, 41:1344-1348.
ADROCA '685 IPR, Exhibit 1007—van Diemen et al., 1992, "The Effect of 4-Aminopyridine on Clinical Signs in Multiple Sclerosis: A Randomized, Placebo-Controlled, Double-Blind, Cross-over Study," Ann. Neurol., 32(2):123-130.
ADROCA '685 IPR, Exhibit 1008—Goodman et al., "Placebo-controlled double-blinded dose ranging study of fampridine-SR in multiple sclerosis," 7th Annual Meeting of the Americas Committee for Treatment and Research in Multiple Sclerosis and 18th Congress of the European Committee for Treatment and Research in Multiple Sclerosis (ACTRIMS/ECTRIMS); Sep. 18-21, 2002, Baltimore, Maryland, USA.
ADROCA '685 IPR, Exhibit 1009—Hayes et al., 2001, "Open-label, multiple-dose study to determine the pharmacokinetics and safety of fampridine-SR (sustained-release 4-aminopyridine) in patients with chronic spinal cord injury," American Neurological Association, Chicago, IL, Sep. 30-Oct. 3, 2001.

ADROCA '685 IPR, Exhibit 1010—U.S. Pat. No. 5,540,938 to Masterson, et al., titled "Formulations and their use in the treatment of neurological diseases".
ADROCA '685 IPR, Exhibit 1011—"Formulating for Controlled Release with METHOCELL Premium cellulose ethers," Dow Chemical Company (1997).
ADROCA '685 IPR, Exhibit 1013—Declaration of Samuel J. Pleasure, M.D., Ph.D.
ADROCA '685 IPR, Exhibit 1014—Information Disclosure Statement dated Oct. 31, 2011, file history of U.S. Pat. No. 8,663,685.
ADROCA '685 IPR, Exhibit 1015—Information Disclosure Statement dated Jun. 7, 2012, file history of U.S. Pat. No. 8,663,685.
ADROCA '685 IPR, Exhibit 1016—Information Disclosure Statement dated Oct. 1, 2012, file history of U.S. Pat. No. 8,663,685.
ADROCA '685 IPR, Exhibit 1017—U.S. Pat. No. 8,440,703 to Blight et al., titled "Methods of using sustained release aminopyridine compositions."
ADROCA '685 IPR, Exhibit 1018—Juarez et al., 2001, "Influence of admixed carboxymethylcellulose on release of 4-aminopyridine from hydroxypropyl methylcellulose matrix tablets," Intl. J. of Pharmaceutics, 216:115-125.
ADROCA '685 IPR, Exhibit 1019—Confavreux et al., 2000, "Relapses and Progression of Disability in Multiple Sclerosis," New England Journal of Medicine 343(20):1430-1438.
ADROCA '685 IPR, Exhibit 1020—Stefoski et al., 1987, "4-Aminopyridine Improves Clinical Signs in Multiple Sclerosis," Ann. Neurol, 21:71-77.
ADROCA '685 IPR, Exhibit 1021—Davis et al., 1990, "Orally Administered 4-Aminopyridine Improves Clinical Signs in Multiple Sclerosis," Ann. Neurol., 27:186-192 (Abstract).
ADROCA '685 IPR, Exhibit 1022—Preliminary Amendment dated Jul. 20, 2011, file history of U.S. Pat. No. 8,663,685.
ADROCA '685 IPR, Exhibit 1023—Reasons for Allowance dated Apr. 25, 2013, file history of U.S. Pat. No. 8,663,685.
ADROCA '685 IPR, Exhibit 1024—Information Disclosure Statement dated Oct. 2, 2013, file history of U.S. Pat. No. 8,663,685.
ADROCA '685 IPR, Exhibit 1025—Notice of Allowance dated Oct. 18, 2013, file history of U.S. Pat. No. 8,663,685.
ADROCA '685 IPR, Exhibit 1026—Information Disclosure Statement dated Jan. 13, 2014, file history of U.S. Pat. No. 8,663,685.
ADROCA '685 IPR, Exhibit 1027—Reasons for Allowance dated Jan. 22, 2014, file history of U.S. Pat. No. 8,663,685.
ADROCA '685 IPR, Exhibit 1028—U.S. Appl. No. 60/528,760, filed Dec. 11, 2003.
ADROCA '685 IPR, Exhibit 1029—U.S. Appl. No. 60/560,894, filed Apr. 9, 2004.
ADROCA '685 IPR, Exhibit 1030—U.S. Appl. No. 60/528,592, filed Dec. 11, 2003.
ADROCA '685 IPR, Exhibit 1031—U.S. Appl. No. 60/528,593, filed Dec. 11, 2003.
ADROCA '685 IPR Exhibit 1032—Polman et al., 1994, "4-Aminopyridine is Superior to 3,4-Diaminopyridine in the Treatment of Patients With Multiple Sclerosis,"Arch. Neurol., 51:1136-1139.
ADROCA '685 IPR, Exhibit 1033—Information Disclosure Statement dated Oct. 1, 2013, file history of U.S. Pat. No. 8,663,685.
ADROCA '685 IPR, Exhibit 1034—U.S. Pat. No. 3,065,143 to Christenson, titled "Sustained Release Tablet".
ADROCA '685 IPR, Exhibit 1035—Declaration of James Polli, Ph.D.
ADROCA '685 IPR, Exhibit 1036—Hauser et al., 2001, "Multiple Sclerosis and Other Demyelinating Diseases," in Harrison's Principles of Internal Medicine, Braunwald et al. (eds.), 15th Edition, McGraw-Hill, pp. 2452-2461.
ADROCA '685 IPR, Exhibit 1038—Response to Restriction Requirement dated Jan. 22, 2008 dated May 21, 2008, file history of U.S. Pat. No. 8,007,826.
ADROCA '685 IPR, Exhibit 1039—Response to Office Action dated Jun. 6, 2008 dated Dec. 8, 2008, file history of U.S. Pat. No. 8,007,826.
ADROCA '685 IPR, Exhibit 1040—Office Action dated May 25, 2010, file history of U.S. Pat. No. 8,007,826.

(56) References Cited

OTHER PUBLICATIONS

ADROCA '685 IPR, Exhibit 1041—Response to Office Action dated May 25, 2010 dated Nov. 24, 2010, file history of U.S. Pat. No. 8,007,826.
ADROCA '685 IPR, Exhibit 1042—Reasons for Allowance dated Apr. 25, 2013, file history of U.S. Pat. No. 8,663,685.
ADROCA '685 IPR, Exhibit 1043—Information Disclosure Statement dated Oct. 31, 2011, file history of U.S. Pat. No. 8,663,685.
ADROCA '685 IPR, Exhibit 1044—Declaration of Andrew Blight, file history of U.S. Pat. No. 8,007,826.
PTAB Decision Denying Institution of IPR issued Aug. 24, 2015 for IPR2015-00720 ("ADROCA '685 IPR").
Petition for Inter Partes Review of U.S. Pat. No. 8,007,826 filed Feb. 27, 2015 by the Coalition for Affordable Drugs (ADROCA) LLC ("ADROCA '826 IPR") (IPR2015-00817).
ADROCA '826 IPR, Exhibit 1001—U.S. Pat. No. 8,007,826 to Andrew R. Blight et al., titled "Sustained Release Aminopyridine Composition".
ADROCA '826 IPR Exhibit 1002—Andrew R. Blight Assignment of U.S. Pat. No. 8,007,826 to Acorda Therapeutics Inc.
ADROCA '826 IPR, Exhibit 1003—Orange Book Listing for U.S. Pat. No. 8,007,826.
ADROCA '826 IPR, Exhibit 1004—U.S. Appl. No. 11/010,828 titled "Sustained Release Aminopyridine Composition" (Dec. 13, 2004).
ADROCA '826 IPR, Exhibit 1005—Response to Restriction Requirement dated Jan. 22, 2008 dated May 21, 2008, file history of U.S. Pat. No. 8,007,826.
ADROCA '826 IPR, Exhibit 1006—Response to Office Action dated Jun. 6, 2008 dated Dec. 8, 2008, file history of U.S. Pat. No. 8,007,826.
ADROCA '826 IPR, Exhibit 1007—Office Action dated May 25, 2010, file history of U.S. Pat. No. 8,007,826.
ADROCA '826 IPR, Exhibit 1008—Hauser et al., 2001, "Multiple Sclerosis and Other Demyelinating Diseases," in Harrison's Principles of Internal Medicine, Braunwald et al. (eds.), 15th Edition, McGraw-Hill, pp. 2452-2461.
ADROCA '826 IPR, Exhibit 1009—U.S. Pat. No. 5,540,938 to Masterson, et al., titled "Formulations and their use in the treatment of neurological diseases".
ADROCA '826 IPR, Exhibit 1010—U.S. Pat. No. 5,580,580, to Masterson, et al., titled "Formulations and their use in the treatment of neurological diseases".
ADROCA '826 IPR, Exhibit 1011—Declaration of Andrew R. Blight, executed Apr. 2, 2009, file history of U.S. Pat. No. 8,007,826.
ADROCA '826 IPR, Exhibit 1012—Declaration of David Lawrence, executed Apr. 2, 2009), file history of U.S. Pat. No. 8,007,826.
ADROCA '826 IPR, Exhibit 1013—Petition Regarding Inventor Sean Cunningham dated Dec. 8, 2008, file history of U.S. Pat. No. 8,007,826.
ADROCA '826 IPR, Exhibit 1014—Request to Correct Inventorship under 37 C.F.R. § 1.48(b) requesting that the PTO delete Sean Cunningham as an inventor dated Dec. 9, 2008, file history of U.S. Pat. No. 8,007,826.
ADROCA '826 IPR, Exhibit 1015—PTO grant of inventorship change mailed Jan. 5, 2009, file history of U.S. Pat. No. 8,007,826.
ADROCA '826 IPR, Exhibit 1016—Declaration of Dr. Rossella Medori executed Nov. 15, 2010, file history of U.S. Pat. No. 8,007,826.
ADROCA '826 IPR, Exhibit 1017—Declaration of Lauren Sabella executed Nov. 23, 2010, file history of U.S. Pat. No. 8,007,826.
ADROCA '826 IPR, Exhibit 1018—Response to Office Action dated May 25, 2010 dated Nov. 24, 2010, file history of U.S. Pat. No. 8,007,826.
ADROCA '826 IPR, Exhibit 1019—Information Disclosure Statement dated Nov. 24, 2010, file history of U.S. Pat. No. 8,007,826.
ADROCA '826 IPR, Exhibit 1020—Reasons for Allowance dated Apr. 18, 2011, file history of U.S. Pat. No. 8,007,826.
ADROCA '826 IPR, Exhibit 1022—U.S. Appl. No. 60/528,760, filed Dec. 11, 2003.
ADROCA '826 IPR, Exhibit 1023—U.S. Appl. No. 60/528,592, filed Dec. 11, 2003.
ADROCA '826 IPR, Exhibit 1024—U.S. Appl. No. 60/528,593, filed Dec. 11, 2003.
ADROCA '826 IPR, Exhibit 1025—U.S. Appl. No. 60/560,894, filed Apr. 9, 2004.
ADROCA '826 IPR, Exhibit 1026—Declaration of Samuel J. Pleasure, M.D., Ph.D.
ADROCA '826 IPR, Exhibit 1027—Declaration of James Polli, Ph.D.
ADROCA '826 IPR, Exhibit 1028—Securities and Exchange Commission Form S-1 for Acorda Therapeutics, Inc. dated Sep. 29, 2003.
ADROCA '826 IPR, Exhibit 1029—Hayes et al., 2003, "Pharmacokinetics Studies of Single and Multiple Oral Doses of Fampridine-SR (Sustained-Release 4-Aminopyridine) in Patients With Chronic Spinal Cord Injury," Clinical Neuropharmacology, 26(4):185-192.
ADROCA '826 IPR, Exhibit 1030—Goodman et al., "Placebo-controlled double-blinded dose ranging study of fampridine-SR in multiple sclerosis," 7th Annual Meeting of the Americas Committee for Treatment and Research in Multiple Sclerosis and 18th Congress of the European Committee for Treatment and Research in Multiple Sclerosis (ACTRIMS/ECTRIMS), Sep. 18-21, 2002, Baltimore, Maryland, USA.
ADROCA '826 IPR, Exhibit 1031—Hayes et al., 2001, "Open-label, multiple-dose study to determine the pharmacokinetics and safety of fampridine-SR (sustained-release 4-aminopyridine) in patients with chronic spinal cord injury," American Neurological Association, Chicago, IL, Sep. 30-Oct. 3, 2001.
ADROCA '826 IPR, Exhibit 1032—Jones et al., 1983, "Effects of 4-Aminopyridine in Patients with Multiple Sclerosis," J. Neurol Sci., 60:353-362.
ADROCA '826 IPR, Exhibit 1033—van Diemen et al., 1992, "The Effect of 4-Aminopyridine on Clinical Signs in Multiple Sclerosis: A Randomized, Placebo-Controlled, Double-Blind, Cross-over Study," Ann. Neurol., 32(2):123-130.
ADROCA '826 IPR' Exhibit 1034—Polman et al., 1994, "4-Aminopyridine is Superior to 3,4-Diammopyndine in the Treatment of Patients With Multiple Sclerosis, "Arch. Neurol., 51:1136-1139.
ADROCA '826 IPR, Exhibit 1035—Confavreux et al., 2000, "Relapses and Progression of Disability in Multiple Sclerosis," New England Journal of Medicine 343(20):1430-1438.
ADROCA '826 IPR, Exhibit 1036—Stefoski et al., 1987, "4-Aminopyridine Improves Clinical Signs in Multiple Sclerosis," Ann. Neurol, 21:71-77.
ADROCA '826 IPR, Exhibit 1037—Davis et al., 1990, "Orally Administered 4-Aminopyridine Improves Clinical Signs in Multiple Sclerosis," Ann. Neurol., 27:186-192.
ADROCA '826 IPR, Exhibit 1038—Cover Sheets for U.S. Appl. Nos. 60/528,592, 60/528,760, and 60/528,593.
ADROCA '826 IPR, Exhibit 1039—Response to Final Office Action dated Jun. 10, 2009 and Request for Continued Examination dated Dec. 10, 2009, file history of U.S. Pat. No. 8,007,826.
ADROCA '826 IPR, Exhibit 1040—Office Action dated Jun. 10, 2009, file history of U.S. Pat. No. 8,007,826.
ADROCA '826 IPR, Exhibit 1041—Office Action dated May 25, 2010, file history of U.S. Pat. No. 8,007,826.
ADROCA '826 IPR, Exhibit 1042—Information Disclosure Statement dated Oct. 1, 2012, file history of U.S. Pat. No. 8,007,826.
ADROCA '826 IPR, Exhibit 1043—Juarez et al., 2001, "Influence of admixed carboxymethylcellulose on release of 4-aminopyridine from hydroxypropyl methylcellulose matrix tablets," Intl. J. of Pharmaceutics, 216:115-125.
ADROCA '826 IPR, Exhibit 1044—Tang et al., 1996, "Frequency-dependent inhibition of neurotransmitter release by besipirdine and HP 184," European Journal of Pharmacology, 300:71-74.
ADROCA '826 IPR, Exhibit 1045—U.S. Pat. No. 4,812,447 to Roberts titled "Method for the Treatment of Nervous System Degeneration".

(56) References Cited

OTHER PUBLICATIONS

ADROCA '826 IPR, Exhibit 1046—SEC News Digest, Issue 2003-186, Sep. 30, 2003 (http://www.sec.gov/news/digest/dig093003.txt; last accessed Feb. 2, 2015).
ADROCA '826 IPR, Exhibit 1047—Response to Office Action dated Jun. 6, 2008 dated Dec. 8, 2008, file history of U.S. Pat. No. 8,007,826.
ADROCA '826 IPR, Exhibit 1048—Supplemental Amendment and Response dated Apr. 2, 2009, file history of U.S. Pat. No. 8,007,826.
ADROCA '826 IPR, Exhibit 1049—Information Disclosure Statement dated Oct. 31, 2011, file history of U.S. Pat. No. 8,663,685.
ADROCA '826 IPR, Exhibit 1050—Transcription of Hayes et al., 2001, "Open-label, multiple-dose study to determine the pharmacokinetics and safety of fampridine-SR (sustained-release 4-aminopyridine) in patients with chronic spinal cord injury," American Neurological Association, Chicago, IL, Sep. 30-Oct. 3, 2001.
ADROCA '826 IPR, Exhibit 1051—Reproduction of Table 2 of Hayes et al., 2001, "Open-label, multiple-dose study to determine the pharmacokinetics and safety of fampridine-SR (sustained-release 4-aminopyridine) in patients with chronic spinal cord injury," American Neurological Association, Chicago, IL, Sep. 30-Oct. 3, 2001.
ADROCA '826 IPR, Exhibit 1052—Reproduction of Dose Response in Goodman et al., "Placebo-controlled double-blinded dose ranging study of fampridine-SR in multiple sclerosis," 7th Annual Meeting of the Americas Committee for Treatment and Research in Multiple Sclerosis and 18th Congress of the European Committee for Treatment and Research in Multiple Sclerosis (ACTRIMS/ECTRIMS), Sep. 18-21, 2002, Baltimore, Maryland, USA.
PTAB Decision Denying Institution of IPR issued Aug. 24, 2015 for IPR2015-00817 ("ADROCA '826 IPR").
Petition for Inter Partes Review of U.S. Pat. No. 8,440,703 filed Sep. 2, 2015 by the Coalition for Affordable Drugs (ADROCA) LLC ("ADROCA '703 IPR") (IPR2015-01850).
IPR2015-01850 (ADROCA '703 IPR) Exhibit 1001—Andrew R. Blight & Ron Cohen, U.S. Pat. No. 8,440,703 (filed Nov. 18, 2011) (issued May 14, 2013) ("the '703 Patent").
IPR2015-01850 (ADROCA '703 IPR) Exhibit 1002—Relevant excerpts of U.S. Pat. No. 8,440,703 Prosecution History ("'703 prosecution history")—Part 1.
IPR2015-01850 (ADROCA '703 IPR) Exhibit 1003—Acorda Therapeutics, Inc., Registration Statement Under the Securities Act of 1933 (Form S-1) (Sep. 26, 2003) ("S-1").
IPR2015-01850 (ADROCA '703 IPR) Exhibit 1004—Rules and Related Matters, 2003-186 (Sep. 30, 2003), available at http://www.sec.gov/news/digest/dig093003.txt ("S-1 Registration Statement").
IPR2015-01850 (ADROCA '703 IPR) Exhibit 1005—Keith C. Hayes et al., "Pharmacokinetic Studies of Single and Multiple Oral Doses of Fampridine-SR (Sustained-Release 4-Aminopyridine) in Patients With Chronic Spinal Cord Injury," 26 Clinical Neuropharmacology, No. 4, 2003, at 185-92 ("Hayes").
IPR2015-01850 (ADROCA '703 IPR) Exhibit 1006—Haydee Juárez et al., "Influence of Admixed Carboxymethylcellulose on Release of 4-Aminopyridine from Hydroxypropyl Methylcellulose Matrix Tablets," 216 Int'l J. Pharm., 2001, at 115-25 ("Juarez").
IPR2015-01850 (ADROCA '703 IPR) Exhibit 1007—U.S. Appl. No. 60/560,894, filed Apr. 9, 2004 ("the Provisional").
IPR2015-01850 (ADROCA '703 IPR) Exhibit 1008—Masterson et al., U.S. Pat. No. 5,540,938, "Formulations and Their Use in the Treatment of Neurological Diseases" (filed Oct. 24, 1994) ("Masterson").
IPR2015-01850 (ADROCA '703 IPR) Exhibit 1009—Schwid et al., "Quantitative Assessment of Sustained Release 4-Aminopyridine for Symptomatic Treatment of Multiple Sclerosis," 48 Neurol., No. 4, at 817-21 (Apr. 1997) ("Schwid").
IPR2015-01850 (ADROCA '703 IPR) Exhibit 1010—Richard E. Jones et al., "Effects of 4-Aminopyridine in Patients with Multiple Sclerosis," 60 J. Neurol. Sci. at 353-62 (1983) ("Jones").
IPR2015-01850 (ADROCA '703 IPR) Exhibit 1011—Harriët van Diemen, M.D. et al., "The Effect of 4-Aminopyridine on the Clinical Signs in Multiple Sclerosis: A Randomized, Placebo-Controlled, Double-Blind, Cross-over Study," 32 Annals Neurol., No. 2, at 123-30 (Aug. 1992) ("van Diemen").
IPR2015-01850 (ADROCA '703 IPR) Exhibit 1012—Chris H. Polman, MD, PhD et al., "4-Aminipyridine is Superior to 3,4,diaminopyridine in the Treatment of Patients with Multiple Sclerosis," 51 Archives Neurol., No. 11, Nov. 1994, at 1136-39 ("Polman").
IPR2015-01850 (ADROCA '703 IPR) Exhibit 1013—D. Stefoski, M.D. et al., "4-Aminopyridine Improves Clinical Signs in Multiple Sclerosis," 21 Annals Neurol., No. 1, at 71-77 (1987) ("Stefoski").
IPR2015-01850 (ADROCA '703 IPR) Exhibit 1014—Floyd A. Davis, M.D. et al., "Orally Administered 4-Aminopyridine Improves Clinical Signs in Multiple Sclerosis," 27 Annals Neurol., No. 2, at 186-92 (Feb. 1990) ("Davis").
IPR2015-01850 (ADROCA '703 IPR) Exhibit 1015—"Types of MS," Nat. Multiple Sclerosis Soc'y, http://www.nationalmssociety.org/What-is-MS/Types-of-MS (last visited Aug. 11, 2015) ("NMSS").
IPR2015-01850 (ADROCA '703 IPR) Exhibit 1016—Declaration of Scott Bennett ("Bennett Decl.").
IPR2015-01850 (ADROCA '703 IPR) Exhibit 1017—C. Darlington, Abstract Fampridine Acorda Therapeutics, 1 Current Opinions in Investigational Drugs, No. 3, Nov. 2000, at 375-79.
IPR2015-01850 (ADROCA '703 IPR) Exhibit 1018—Porter Novelli, "Acorda Therapeutics Begins Phase 3 Trials of Fampridine-SR for Chronic Spinal Cord Injury," American Association for the Advancement of Science (AAAS) EurekAlert! (Jul. 1, 2002), http://www.eurekalert.org/pub_releases/2002-07/pn-atb062802.php.
IPR2015-01850 (ADROCA '703 IPR) Exhibit 1019—Acorda Therapeutics Company Profile, Biospace, http://www.biospace.com/company_profile.aspx?CompanyId=100704 (last updated May 9, 2003).
IPR2015-01850 (ADROCA '703 IPR) Exhibit 1020—Goodman et al., "Placebo-Controlled Double-Blinded Dose Ranging Study of Fampridine-SR in Multiple Sclerosis," poster presented at the 7th Annual Meeting of the Americas Committee for Treatment and Research in Multiple Sclerosis and 18th Congress of the European Committee for Treatment and Research in Multiple Sclerosis (ACTRIMS/ECTRIMS), Sep. 18-21, 2002, Baltimore, MD ("Goodman").
IPR2015-01850 (ADROCA '703 IPR) Exhibit 1021—European Patent Convention art. 54(1), (2), Oct. 5, 1973, 1065 U.N.T.S. 199 (as amended Nov. 29, 2000), available at http://www.epo.org/law-practice/legal-texts/html/epc/2010/e/ar54.html-texts/html/epc/2010/e/ar54.html ("EPC Art. 54").
IPR2015-01850 (ADROCA '703 IPR) Exhibit 1022—Fred D. Lublin, M.D. & Stephen C. Reingold Ph.D., "Defining the Clinical Course of Multiple Sclerosis: Results of an International Survey," 46 Neurology, No. 4, at 907-11 (Apr. 1996) ("Lublin").
IPR2015-01850 (ADROCA '703 IPR) Exhibit 1023—Declaration of Samuel J. Pleasure, M.D., Ph.D. ("Pleasure Decl.").
IPR2015-01850 (ADROCA '703 IPR) Exhibit 1024—CV of Samuel J. Pleasure, M.D., Ph.D. ("Pleasure CV").
IPR2015-01850 (ADROCA '703 IPR) Exhibit 1025—European U.S. Pat. No. 1 732 548 (B9) ("EP '548").
IPR2015-01850 (ADROCA '703 IPR) Exhibit 1026—Excerpts from Proprietor's Response to Opponents' Appeals, European Patent No. 1 732 548 B9, filed with the EPO, Sep. 16, 2004 ("Acorda EP Brief").
IPR2015-01850 (ADROCA '703 IPR) Exhibit 1027—European Patent Office, Espacenet Brochure, http://documents.epo.org/projects/babylon/eponet.nsf/0/4E8744EB66E8F944C12577D600598EEF/$File/espacenet_brochure_en.pdf ("Espacenet Brochure").
IPR2015-01850 (ADROCA '703 IPR) Exhibit 1028—Espacenet Bibliographic Data for U.S. Pat. No. 8,440,703 (B2) ("Espacenet 703 Data").
IPR2015-01850 (ADROCA '703 IPR) Exhibit 1029—CV of Scott Bennett ("Bennett CV").

(56) References Cited

OTHER PUBLICATIONS

IPR2015-01850 (ADROCA '703 IPR) Exhibit 1030—Bennett Decl. Attachment 1.
IPR2015-01850 (ADROCA '703 IPR) Exhibit 1031—Bennett Decl. Attachment 2.
IPR2015-01850 (ADROCA '703 IPR) Exhibit 1032—Bennett Decl. Attachment 3.
IPR2015-01850 (ADROCA '703 IPR) Exhibit 1033—Bennett Decl. Attachment 4.
IPR2015-01850 (ADROCA '703 IPR) Exhibit 1034—Bennett Decl. Attachment 5.
IPR2015-01850 (ADROCA '703 IPR) Exhibit 1035—Bennett Decl. Attachment 6.
IPR2015-01850 (ADROCA '703 IPR) Exhibit 1036—Bennett Decl. Attachment 7.
IPR2015-01850 (ADROCA '703 IPR) Exhibit 1037—Bennett Decl. Attachment 8.
IPR2015-01850 (ADROCA '703 IPR) Exhibit 1038—Bennett Decl. Attachment 9.
IPR2015-01850 (ADROCA '703 IPR) Exhibit 1039—Stephen L. Hauser, M.D. & Donald E. Goodkin, Harrison's Principles of Internal Medicine, 2452-61, 15th ed. 2001.
IPR2015-01850 (ADROCA '703 IPR) Exhibit 1040—Christian Confavreux, M.D. et al, "Relapses and Progression of Disability in Multiple Sclerosis," 343 New Eng. J. Med., No. 20, at 1430-38 (Nov. 16, 2000).
IPR2015-01850 (ADROCA '703 IPR) Exhibit 1041—Timed 25-Foot Walk (T25-FW), Nat'l Multiple Sclerosis Soc'y Website, http://www.nationalmssociety.org/For-Professionals/Research/Resources-for-Researchers/Clinical-Study-Measures/Timed-25-Foot-Walk-(T25-FW) (last visited Aug. 31, 2015).
IPR2015-01850 (ADROCA '703 IPR) Exhibit 1043—Pleasure Decl. and Polli Decl. Attachment 2 (Claim Charts for the '703 Patent).
IPR2015-01850 (ADROCA '703 IPR) Exhibit 1044—Declaration of James Polli, Ph.D. ("Polli Decl.").
IPR2015-01850 (ADROCA '703 IPR) Exhibit 1045—CV of James Polli, Ph.D. ("Polli CV").
IPR2015-01850 (ADROCA '703 IPR) Exhibit 1046—Relevant excerpts of U.S. Pat. No. 8,440,703 Prosecution History ("'703 prosecution history")—Part 2.
IPR2015-01850 (ADROCA '703 IPR) Exhibit 1047—Relevant excerpts of U.S. Pat. No. 8,440,703 Prosecution History ("'703 prosecution history")—Part 3.
PTAB Decision on Institution of IPR on U.S. Pat. No. 8,440,703 issued Mar. 11, 2016 in the ADROCA '703 IPR (IPR2015-01850).
Petitioner's Reply to Patent Owner's Response (Redacted) filed Sep. 29, 2016 by the Coalition for Affordable Drugs (ADROCA) LLC in the ADROCA '703 IPR (IPR2015-01850).
Petitioner's Current Exhibit List filed Sep. 29, 2016 by the Coalition for Affordable Drugs (ADROCA) LLC in the ADROCA '703 IPR (IPR2015-01850).
IPR2015-01850 (ADROCA '703 IPR) Exhibit 1054—Charles Weijer, 2000, "The ethical analysis of risk," Journal of Law, Medicine, & Ethics, 28(4):344-361.
IPR2015-01850 (ADROCA '703 IPR) Exhibit 1055—"What are the different types of clinical research?," http://www.fda.gov/ForPatients/ClinicalTrials/Types/ucm20041762.htm (last visited Sep. 7, 2016).
IPR2015-01850 (ADROCA '703 IPR) Exhibit 1056—"Electronic code of federal regulations," http://www.ecfr.gov/cgi-bin/text-idx?SID=d428bea027fdfl8fa4b31dc68ed5e918&mc=true&node=pt21.5.312&rgn=div5#sp21.5.312a (last visited Sep. 7, 2016).
IPR2015-01850 (ADROCA '703 IPR) Exhibit 1057—Lee et al., 2005, "Evidence of effectiveness: how much can we extrapolate from existing studies?," The AAPS Journal, 7(2):E467-E474.
IPR2015-01850 (ADROCA '703 IPR) Exhibit 1058—Lesko et al., 2000, "Optimizing the science of drug development: opportunites for better candidate selection and accelerated evaluation in humans," Eur. J. Pharm. Sci., 10:iv-xiv.
IPR2015-01850 (ADROCA '703 IPR) Exhibit 1060—Relevant excerpts of U.S. Pat. No. 8,007,826 Prosecution History ("'826 prosecution history").
IPR2015-01850 (ADROCA '703 IPR) Exhibit 1065—Declaration of Samuel J. Pleasure.
IPR2015-01850 (ADROCA '703 IPR) Exhibit 1066—Declaration of William R. Fairweather, Ph.D., PSTAT.
IPR2015-01850 (ADROCA '703 IPR) Exhibit 1067—Declaration of Carrie L. Distler (Redacted).
IPR2015-01850 (ADROCA '703 IPR) Exhibit 1068—CV of William R. Fairweather, Ph.D., PSTAT.
IPR2015-01850 (ADROCA '703 IPR) Exhibit 1069—Deposition of Keith C. Hayes, Ph.D.
IPR2015-01850 (ADROCA '703 IPR) Exhibit 1070—CV of Carrie Distler.
IPR2015-01850 (ADROCA '703 IPR) Exhibit 1071—Hoogstraten et al., 1988, "Tizanidine versus baclofen in the treatment of spasticity in multiple sclerosis patients," Acta. Neurol. Scand., 77:224-230.
IPR2015-01850 (ADROCA '703 IPR) Exhibit 1072—Norman et al., 1998, "Effects of drugs on walking after spinal cord injury," Spinal Cord., 36:699-715.
IPR2015-01850 (ADROCA '703 IPR) Exhibit 1073—Knutsson et al., 1982, "Antiparetic and antispastic effects induced by tizanidine in patients with spastic paresis," J. Neurol. Sci., 53:187-204.
IPR2015-01850 (ADROCA '703 IPR) Exhibit 1074—"Comprehensive Care: National Multiple Sclerosis Society," http://www.nationalmssociety.org/Treating-MS/Comprehensive-Care (last visited Sep. 28, 2016).
IPR2015-01850 (ADROCA '703 IPR) Exhibit 1075—Nadeau et al., 2011, "Acorda Therapeutics—Q1 Light; ACOR remains undervalued despite estimate changes," Cowen and Company, 8 pages.
IPR2015-01850 (ADROCA '703 IPR) Exhibit 1076—"Medications: National Multiple Sclerosis Society," http://www.nationalmssociety.org/TreatingMS/Medications (last visited Aug. 12, 2016).
IPR2015-01850 (ADROCA '703 IPR) Exhibit 1067—Corrected Declaration of Carrie L. Distler (Redacted).
Petition for Inter Partes Review of U.S. Pat. No. 8,007,826 filed Sep. 2, 2015 by the Coalition for Affordable Drugs (ADROCA) LLC ("ADROCA '826 IPR II") (IPR2015-01853).
IPR 2015-01853 (ADROCA '826 IPR II) Exhibit 1001—Andrew R. Blight & Ron Cohen, U.S. Pat. No. 8,007,826 (filed Dec. 13, 2004) (issued Aug. 30, 2011) ("the '826 Patent").
IPR 2015-01853 (ADROCA '826 IPR II) Exhibit 1002—Relevant excerpts of U.S. Pat. No. 8,007,826 Prosecution History ("'826 prosecution history")—Part 1.
IPR 2015-01853 (ADROCA '826 IPR II) Exhibit 1003—Acorda Therapeutics, Inc., Registration Statement Under the Securities Act of 1933 (Form S-1) (Sep. 26, 2003) ("S-1").
IPR 2015-01853 (ADROCA '826 IPR II) Exhibit 1004—Rules and Related Matters, 2003-186 (Sep. 30, 2003), available at http://www.sec.gov/news/digest/dig093003.txt ("S-1 Registration Statement").
IPR 2015-01853 (ADROCA '826 IPR II) Exhibit 1005—Keith C. Hayes et al., "Pharmacokinetic Studies of Single and Multiple Oral Doses of Fampridine-SR (Sustained-Release 4-Aminopyridine) in Patients With Chronic Spinal Cord Injury," 26 Clinical Neuropharmacology, No. 4, 2003, at 185-92 ("Hayes").
IPR 2015-01853 (ADROCA '826 IPR II) Exhibit 1006—U.S. Appl. No. 60/528,760, filed Dec. 11, 2003 ("'760 Provisional").
IPR 2015-01853 (ADROCA '826 IPR II) Exhibit 1007—U.S. Appl. No. 60/560,894, filed Apr. 9, 2004 ("'894 Provisional").
IPR 2015-01853 (ADROCA '826 IPR II) Exhibit 1008—Masterson et al., U.S. Pat. No. 5,540,938, "Formulations and Their Use in the Treatment of Neurological Diseases" (filed Oct. 24, 1994) ("Masterson").
IPR 2015-01853 (ADROCA '826 IPR H) Exhibit 1009—Schwid et al., "Quantitative Assessment of Sustained Release 4-Aminopyridine for Symptomatic Treatment of Multiple Sclerosis," 48 Neurol., No. 4, at 817-21 (Apr. 1997) ("Schwid").

(56) References Cited

OTHER PUBLICATIONS

IPR 2015-01853 (ADROCA '826 IPR II) Exhibit 1010—Richard E. Jones et al., "Effects of 4-Aminopyridine in Patients with Multiple Sclerosis," 60 J. Neurol. Sci. at 353-62 (1983) ("Jones").
IPR 2015-01853 (ADROCA '826 IPR II) Exhibit 1011—Harriët van Diemen, M.D. et al., "The Effect of 4-Aminopyridine on the Clinical Signs in Multiple Sclerosis: A Randomized, Placebo-Controlled, Double-Blind, Cross-over Study," 32 Annal Neurol., No. 2, at 123-30 (Aug. 1992) ("van Diemen").
IPR 2015-01853 (ADROCA '826 IPR II) Exhibit 1012—Chris H. Polman, MD, PhD et al., "4-Aminipyridine is Superior to 3,4,diaminopyridine in the Treatment of Patients with Multiple Sclerosis," 51 Archives Neurol., No. 11, Nov. 1994, at 1136-39 ("Polman").
IPR 2015-01853 (ADROCA '826 IPR II) Exhibit 1013—D. Stefoski, M.D. et al., "4-Aminopyridine Improves Clinical Signs in Multiple Sclerosis," 21 Annals Neurol., No. 1, at 71-77 (1987) ("Stefoski").
IPR 2015-01853 (ADROCA '826 IPR II) Exhibit 1014—Floyd A. Davis, M.D. et al., "Orally Administered 4-Aminopyridine Improves Clinical Signs in Multiple Sclerosis," 27 Annals Neurol., No. 2, at 186-95 (Feb. 1990) ("Davis").
IPR 2015-01853 (ADROCA '826 IPR II) Exhibit 1015—Types of MS, Nat. Multiple Sclerosis Soc'y, http://www.nationalmssociety.org/What-is-MS/Types-of-MS (last visited Aug. 11, 2015) ("NMSS").
IPR 2015-01853 (ADROCA '826 IPR II) Exhibit 1016—Declaration of Scott Bennett ("Bennett Decl.").
IPR 2015-01853 (ADROCA '826 IPR II) Exhibit 1017—C. Darlington, Abstract, Fampridine Acorda Therapeutics, 1 Current Opinions in Investigational Drugs, No. 3, Nov. 2000, at 375-79.
IPR 2015-01853 (ADROCA '826 IPR II) Exhibit 1018—Porter Novelli, "Acorda Therapeutics Begins Phase 3 Trials of Fampridine-SR for Chronic Spinal Cord Injury," American Association for the Advancement of Science (AAAS) EurekAlert! (Jul. 1, 2002), http://www.eurekalert.org/pub_releases/2002-07/pn-atb062802.php.
IPR 2015-01853 (ADROCA '826 IPR II) Exhibit 1019—Acorda Therapeutics Company Profile, Biospace, http://www.biospace.com/company_profile.aspx?CompanyId=100704 (last updated May 9, 2003).
IPR 2015-01853 (ADROCA '826 IPR II) Exhibit 1020—Goodman et al., "Placebo-Controlled Double-Blinded Dose Ranging Study of Fampridine-SR in Multiple Sclerosis," poster presented at the 7th Annual Meeting of the Americas Committee for Treatment and Research in Multiple Sclerosis and 18th Congress of the European Committee for Treatment and Research in Multiple Sclerosis (ACTRIMS/ECTRIMS), Sep. 18-21, 2002, Baltimore, MD ("Goodman").
IPR 2015-01853 (ADROCA '826 IPR II) Exhibit 1021—European Patent Convention art. 54(1), (2), Oct. 5, 1973, 1065 U.N.T.S. 199 (as amended Nov. 29, 2000), available at http://www.epo.org/law-practice/legal-texts/html/epc/2010/e/ar54.html-texts/html/epc/2010/e/ar54.html ("EPC Art. 54").
IPR 2015-01853 (ADROCA '826 IPR II) Exhibit 1022—Fred D. Lublin, M.D. & Stephen C. Reingold. Ph.D., "Defining the Clinical Course of Multiple Sclerosis: Results of an International Survey," 46 Neurology, No. 4, at 907-11 (Apr. 1996) ("Lublin").
IPR 2015-01853 (ADROCA '826 IPR II) Exhibit 1023—Declaration of Samuel J. Pleasure, M.D., Ph.D. ("Pleasure Decl.").
IPR 2015-01853 (ADROCA '826 IPR II) Exhibit 1024—CV of Samuel J. Pleasure, M.D., Ph.D. ("Pleasure CV").
IPR 2015-01853 (ADROCA '826 IPR II) Exhibit 1025—European Patent No. 1 732 548 (B9) ("EP 548").
IPR 2015-01853 (ADROCA '826 IPR II) Exhibit 1026—Excerpts from Proprietor's Response to Opponents' Appeals, European Patent No. 1 732 548 B9, filed with the EPO, Sep. 16, 2004 ("Acorda EP Brief").
IPR 2015-01853 (ADROCA '826 IPR II) Exhibit 1027—European Patent Office, Espacenet Brochure, http://documents.epo.org/projects/babylon/eponet.nsf/0/4E8744EB66E7F944C12577D600598EEF/$File/espacenet_brochure_en.pdf ("Espacenet Brochure").
IPR 2015-01853 (ADROCA '826 IPR II) Exhibit 1028—Espacenet Bibliographic Data for U.S. Pat. No. 8,440,703 (B2) ("Espacenet 703 Data").
IPR 2015-01853 (ADROCA '826 IPR II) Exhibit 1029—CV of Scott Bennett.
IPR 2015-01853 (ADROCA '826 IPR II) Exhibit 1030—Bennett Decl. Attachment 1.
IPR 2015-01853 (ADROCA '826 IPR II) Exhibit 1031—Bennett Decl. Attachment 2.
IPR 2015-01853 (ADROCA '826 IPR II) Exhibit 1032—Bennett Decl. Attachment 3.
IPR 2015-01853 (ADROCA '826 IPR II) Exhibit 1033—Bennett Decl. Attachment 4.
IPR 2015-01853 (ADROCA '826 IPR II) Exhibit 1034—Bennett Decl. Attachment 5.
IPR 2015-01853 (ADROCA '826 IPR II) Exhibit 1035—Bennett Decl. Attachment 6.
IPR 2015-01853 (ADROCA '826 IPR II) Exhibit 1036—Bennett Decl. Attachment 7.
IPR 2015-01853 (ADROCA '826 IPR II) Exhibit 1037—Bennett Decl. Attachment 8.
IPR 2015-01853 (ADROCA '826 IPR II) Exhibit 1038—Bennett Decl. Attachment 9.
IPR 2015-01853 (ADROCA '826 IPR II) Exhibit 1039—Stephen L. Hauser, M.D. & Donald E. Goodkin, Harrison's Principles of Internal Medicine, 2452-61, 15th ed. 2001.
IPR 2015-01853 (ADROCA '826 IPR II) Exhibit 1040—Christian Confavreux, M.D. et al, "Relapses and Progression of Disability in Multiple Sclerosis," 343 New Eng. J. Med., No. 20, at 1430-38 (Nov. 16, 2000).
IPR 2015-01853 (ADROCA '826 IPR II) Exhibit 1041—Timed 25-Foot Walk (T25-FW), Nat'l Multiple Sclerosis Soc'y Website, http://www.nationalmssociety.org/For-Professionals/Researchers/Resources-for-Researchers/Clinical-Study-Measures/Timed-25-Foot-Walk-(T-FW) (last visited Aug. 31, 2015).
IPR 2015-01853 (ADROCA '826 IPR II) Exhibit 1042—CV of James Polli, Ph.D. ("Polli CV").
IPR 2015-01853 (ADROCA '826 IPR II) Exhibit 1043—Pleasure Decl. and Polli Decl. Attachment 2 (Claim Charts for the '826 Patent).
IPR 2015-01853 (ADROCA '826 IPR II) Exhibit 1044—U.S. Appl. No. 60/528,592, filed Dec. 11, 2003 ("'592 Provisional").
IPR 2015-01853 (ADROCA '826 IPR II) Exhibit 1045—U.S. Appl. No. 60/528,593, filed Dec. 11, 2003 ("'593 Provisional").
IPR 2015-01853 (ADROCA '826 IPR II) Exhibit 1046—Orange Book Listing for '826 Patent ("Orange Book").
IPR 2015-01853 (ADROCA '826 IPR II) Exhibit 1047—C.T. Bever, Jr., M.D., et al., "The Effects of 4-Aminopyridine in Multiple Sclerosis Patients: Results of a Randomized, Placebo-Controlled, Double-Blind, Concentration-Controlled, Crossover Trial," 1054 Neurology No. 44, Jun. 1994, at 1054—59 ("Bever").
IPR 2015-01853 (ADROCA '826 IPR II) Exhibit 1048—Andrew R. Blight & Ron Cohen, U.S. Pat. No. 8,354,437 (filed Apr. 8, 2005) (issued Jan. 15, 2013) ("the '437 Patent").
IPR 2015-01853 (ADROCA '826 IPR II) Exhibit 1049—Declaration of James Polli, Ph.D. ("Polli Decl.").
IPR 2015-01853 (ADROCA '826 IPR II) Exhibit 1050—Relevant excerpts of U.S. Pat. No. 8,007,826 Prosecution History—Subpart 2 ("'826 prosecution history")—Part 2.
PTAB Decision on Institution of IPR on U.S. Pat. No. 8,007,826 issued Mar. 11, 2016 in the ADROCA '826 IPR II (IPR2015-01853).
Petitioner's Reply to Patent Owner's Response (Redacted) filed Sep. 29, 2016 by the Coalition for Affordable Drugs (ADROCA) LLC in the ADROCA '826 IPR II (IPR2015-01853).
Petitioner's Current Exhibit List filed Sep. 29, 2016 by the Coalition for Affordable Drugs (ADROCA) LLC in the ADROCA '826 IPR II (IPR2015-01853).

(56) References Cited

OTHER PUBLICATIONS

IPR2015-01853 (ADROCA '826 IPR II) Exhibit 1057—Charles Weijer, 2000, "The ethical analysis of risk," Journal of Law, Medicine, & Ethics, 28(4):344-361.
IPR2015-01853 (ADROCA '826 IPR II) Exhibit 1058 —"What are the different types of clinical research?," http://www.fda.gov/ForPatients/ClinicalTrials/Types/ucm20041762.htm (last visited Sep. 7, 2016).
IPR2015-01853 (ADROCA '826 IPR II) Exhibit 1059—"Electronic code of federal regulations," http://www.ecfr.gov/cgi-bin/text-idx?SID=d428bea027fc1f18fa4b31dc68ed5e918&mc=true&node=pt21.5.312&rgn=div5#sp21.5.312a (last visited Sep. 7, 2016).
IPR2015-01853 (ADROCA '826 IPR II) Exhibit 1060—Lee et al., 2005, "Evidence of effectiveness: how much can we extrapolate from existing studies?," The AAPS Journal, 7(2):E467-E474.
IPR2015-01853 (ADROCA '826 IPR II) Exhibit 1061—Lesko et al., 2000, "Optimizing the science of drug development: opportunites for better candidate selection and accelerated evaluation in humans," Eur. J. Pharm. Sci., 10:iv-xiv.
IPR2015-01853 (ADROCA '826 IPR II) Exhibit 1063—Relevant excerpts of U.S. Pat. No. 8,007,826 Prosecution History ("'826 prosecution history").
IPR2015-01853 (ADROCA '826 IPRI II) Exhibit 1068—Declaration of Samuel J. Pleasure.
IPR2015-01853 (ADROCA '826 IPR II) Exhibit 1069—Declaration of William R. Fairweather, Ph.D., PSTAT.
IPR2015-01853 (ADROCA '826 IPR II) Exhibit 1070—Declaration of Carrie L. Distler (Redacted).
IPR2015-01853 (ADROCA '826 IPR II) Exhibit 1071—CV of William R. Fairweather, Ph.D., PSTAT.
IPR2015-01853 (ADROCA '826 IPR II) Exhibit 1072—Deposition of Keith C. Hayes, Ph.D.
IPR2015-01853 (ADROCA '826 IPR II) Exhibit 1073—CV of Carrie Distler.
IPR2015-01853 (ADROCA '826 IPR II) Exhibit 1074—Hoogstraten et al., 1988, "Tizanidine versus baclofen in the treatment of spasticity in multiple sclerosis patients," Acta. Neurol. Scand., 77:224-230.
IPR2015-01853 (ADROCA '826 IPR II) Exhibit 1075—Norman et al., 1998, "Effects of drugs on walking after spinal cord injury," Spinal Cord, 36:699-715.
IPR2015-01853 (ADROCA '826 IPR II) Exhibit 1076—Knutsson et al., 1982, "Antiparetic and antispastic effects induced by tizanidine in patients with spastic paresis," J. Neurol. Sci., 53:187-204.
IPR2015-01853 (ADROCA '826 IPR II) Exhibit 1077—"Comprehensive Care: National Multiple Sclerosis Society," http://www.nationalmssociety.org/Treating-MS/Comprehensive-Care (last visited Sep. 28, 2016).
IPR2015-01853 (ADROCA '826 IPR II) Exhibit 1078—Nadeau et al., 2011, "Acorda Therapeutics—Q1 Light; ACOR remains undervalued despite estimate changes," Cowen and Company, 8 pages.
IPR2015-01853 (ADROCA '826 IPR II) Exhibit 1079—"Medications: National Multiple Sclerosis Society," http://www.nationalmssociety.org/TreatingMS/Medications (last visited Aug. 12, 2016).
IPR2015-01853 (ADROCA '826 IPR II) Exhibit 1070—Corrected Declaration of Carrie L. Distler (Redacted).
Petition for Inter Partes Review of U.S. Pat. No. 8,663,685 filed Sep. 2, 2015 by the Coalition for Affordable Drugs (ADROCA) LLC ("ADROCA '685 IPR II") (IPR2015-01857).
IPR 2015-01857 (ADROCA '685 IPR II) Exhibit 1001—Andrew R. Blight & Ron Cohen, U.S. Pat. No. 8,663,685 (filed Jun. 20, 2011) (issued Mar. 4, 2014) ("The '826 Patent").
IPR 2015-01857 (ADROCA '685 IPR II) Exhibit 1002—Relevant excerpts of U.S. Pat. No. 8,663,685 Prosecution History ("'685 prosecution history").
IPR 2015-01857 (ADROCA '685 IPR II) Exhibit 1003—Acorda Therapeutics, Inc., Registration Statement Under the Securities Act of 1933 (Form S-1) (Sep. 26, 2003) ("S-1").
IPR 2015-01857 (ADROCA '685 IPR II) Exhibit 1004—Rules and Related Matters, 2003-186 (Sep. 30, 2003), available at http://www.sec.gov/news/digest/dig093003.txt ("S-1 Registration Statement").
IPR 2015-01857 (ADROCA '685 IPR II) Exhibit 1005—Keith C. Hayes et al., "Pharmacokinetic Studies of Single and Multiple Oral Doses of Fampridine-SR (Sustained-Release 4-Aminopyridine) in Patients With Chronic Spinal Cord Injury," 26 Clinical Neuropharmacology, No. 4, 2003, at 185-92 ("Hayes").
IPR 2015-01857 (ADROCA '685 IPR II) Exhibit 1006—Haydee Juarez et al., "Influence of Admixed Carboxymethylcellulose on Release of 4-Aminopyridine from Hydroxypropyl Methylcellulose Matrix Tablets," 216 Int'l J. Pharm., 2001, at 115-25 ("Juarez").
IPR 2015-01857 (ADROCA '685 IPR II) Exhibit 1007—U.S. Appl. No. 60/560,894, filed Apr. 9, 2004 ("'894 Provisional").
IPR 2015-01857 (ADROCA '685 IPR II) Exhibit 1008—Masterson et al., U.S. Pat. No. 5,540,938, "Formulations and Their Use in the Treatment of Neurological Diseases" (filed Oct. 24, 1994) ("Masterson").
IPR 2015-01857 (ADROCA '685 IPR II) Exhibit 1009—Schwid et al., "Quantitative Assessment of Sustained Release 4-Aminopyridine for Symptomatic Treatment of Multiple Sclerosis," 48 Neurol., No. 4, at 817-21 (Apr. 1997) ("Schwid").
IPR 2015-01857 (ADROCA '685 IPR II) Exhibit 1010—Richard E. Jones et al., "Effects of 4-Aminopyridine in Patients with Multiple Sclerosis," 60 J. Neurol. Sci. at 353-62 (1983) ("Jones").
IPR 2015-01857 (ADROCA '685 IPR II) Exhibit 1011—Harriët van Diemen, M.D. et al., "The Effect of 4-Aminopyridine on the Clinical Signs in Multiple Sclerosis: A Randomized, Placebo-Controlled, Double-Blind, Cross-over Study," 32 Annals Neurol., No. 2, at 123-30 (Aug. 1992) ("van Diemen").
IPR 2015-01857 (ADROCA '685 IPR II) Exhibit 1012—Chris H. Polman, MD, PhD et al., "4-Aminipyridine is Superior to 3,4,diaminopyridine in the Treatment of Patients with Multiple Sclerosis," 51 Archives Neurol., No. 11, Nov. 1994, at 1136-39 ("Polman").
IPR 2015-01857 (ADROCA '685 IPR II) Exhibit 1013—D. Stefoski, MD, et al., "4-Aminopyridine Improves Clinical Signs in Multiple Sclerosis," 21 Annals Neurol., No. 1, Jan. 1987, at 71-77 ("Stefoski").
IPR 2015-01857 (ADROCA '685 IPR II) Exhibit 1014—Floyd A. Davis, M.D. et al., "Orally Administered 4-Aminopyridine Improves Clinical Signs in Multiple Sclerosis," 27 Annals Neurol., No. 2, at 186-92 (Feb. 1990) ("Davis").
IPR 2015-01857 (ADROCA '685 IPR II) Exhibit 1015—Types of MS, Nat. Multiple Sclerosis Soc'y, http://www.nationalmssocietv.org/What-is-MS/Types-of-MS (last visited Aug. 11, 2015) ("NMSS").
IPR 2015-01857 (ADROCA '685 IPR II) Exhibit 1016—Declaration of Scott Bennett ("Bennett Decl.").
IPR 2015-01857 (ADROCA '685 IPR II) Exhibit 1017—C. Darlington, Abstract, Fampridine Acorda Therapeutics, 1 Current Opinions in Investigational Drugs, No. 3, Nov. 2000, at 375-79.
IPR 2015-01857 (ADROCA '685 IPR II) Exhibit 1018—Porter Novelli, "Acorda Therapeutics Begins Phase 3 Trials of Fampridine-SR for Chronic Spinal Cord Injury," American Association for the Advancement of Science (AAAS) EurekAlert! (Jul. 1, 2002), http://www.eurekalert.org/pub_releases/2002-07/pn-atb062802.php.
IPR 2015-01857 (ADROCA '685 IPR II) Exhibit 1019—Acorda Therapeutics Company Profile, Biospace, http://www.biospace.com/company_profile.aspx?CompanyId=100 704 (last updated May 9, 2003).
IPR 2015-01857 (ADROCA '685 IPR II) Exhibit 1020—Goodman et al., "Placebo-Controlled Double-Blinded Dose Ranging Study of Fampridine-SR in Multiple Sclerosis," poster presented at the 7th Annual Meeting of the Americas Committee for Treatment and Research in Multiple Sclerosis and 18th Congress of the European Committee for Treatment and Research in Multiple Sclerosis (ACTRIMS/ECTRIMS), Sep. 18-21, 2002, Baltimore, MD ("Goodman").

(56) References Cited

OTHER PUBLICATIONS

IPR 2015-01857 (ADROCA '685 IPR II) Exhibit 1021—European Patent Convention art. 54(1), (2), Oct. 5, 1973, 1065 U.N.T.S. 199 (as amended Nov. 29, 2000), available at http://www.epo.org/law-practice/legal-texts/html/epc/2010/e/ar54.html-texts/html/epc/2010/e/ar54.html ("EPC Art. 54").
IPR 2015-01857 (ADROCA '685 IPR II) Exhibit 1022—Fred D. Lublin, Stephen C. Reingold, "Defining the clinical course of multiple sclerosis: Results of an international survey," 46 Neurology, No. 4, Apr. 1996, at 907-911 ("Lublin").
IPR 2015-01857 (ADROCA '685 IPR II) Exhibit 1023—Declaration of Samuel J. Pleasure, M.D., Ph.D. ("Pleasure Decl.").
IPR 2015-01857 (ADROCA '685 IPR II) Exhibit 1024—CV of Samuel J. Pleasure, M.D., Ph.D. ("Pleasure CV").
IPR 2015-01857 (ADROCA '685 IPR II) Exhibit 1025—European Patent No. 1 732 548 (B9) ("EP 548").
IPR 2015-01857 (ADROCA '685 IPR II) Exhibit 1026—Excerpts from Proprietor's Response to Opponents' Appeals, European Patent No. 1 732 548 B9, filed with the EPO, Sep. 16, 2004 ("Acorda EP Brief").
IPR 2015-01857 (ADROCA '685 IPR II) Exhibit 1027—European Patent Office, Espacenet Brochure, http://documents.epo.org/projects/babylon/eponet.nsf/0/4E8744EB66E8F944C12577D600598EEF/$File/espacenet_brochure_en.pdf ("Espacenet Brochure").
IPR 2015-01857 (ADROCA '685 IPR II) Exhibit 1028—Espacenet Bibliographic Data for U.S. Pat. No. 8,440,703 (B2) ("Espacenet 703 Data").
IPR 2015-01857 (ADROCA '685 IPR II) Exhibit 1029—CV of Scott Bennett.
IPR 2015-01857 (ADROCA '685 IPR II) Exhibit 1030—Bennett Decl. Attachment 1.
IPR 2015-01857 (ADROCA '685 IPR II) Exhibit 1031—Bennett Decl. Attachment 2.
IPR 2015-01857 (ADROCA '685 IPR II) Exhibit 1032—Bennett Decl. Attachment 3.
IPR 2015-01857 (ADROCA '685 IPR II) Exhibit 1033—Bennett Decl. Attachment 4.
IPR 2015-01857 (ADROCA '685 IPR II) Exhibit 1034—Bennett Decl. Attachment 5.
IPR 2015-01857 (ADROCA '685 IPR II) Exhibit 1035—Bennett Decl. Attachment 6.
IPR 2015-01857 (ADROCA '685 IPR II) Exhibit 1036—Bennett Decl. Attachment 7.
IPR 2015-01857 (ADROCA '685 IPR II) Exhibit 1037—Bennett Decl. Attachment 8.
IPR 2015-01857 (ADROCA '685 IPR II) Exhibit 1038—Bennett Decl. Attachment 9.
IPR 2015-01857 (ADROCA '685 IPR II) Exhibit 1039—Stephen L. Hauser, M.D. & Donald E. Goodkin, Harrison's Principles of Internal Medicine, 2452-61, 15th ed. 2001.
IPR 2015-01857 (ADROCA '685 IPR II) Exhibit 1040—Christian Confavreux, M.D. et al, "Relapses and Progression of Disability in Multiple Sclerosis," 343 New Eng. J. Med., No. 20, at 1430-38 (Nov. 16, 2000).
IPR 2015-01857 (ADROCA '685 IPR II) Exhibit 1041—Timed 25-Foot Walk (T25-FW), Nat'l Multiple Sclerosis Soc'y Website, http://www.nationalmssociety.org/For-Professionals/Researchers/Resources-for-Researchers/Clinical-Study-Measures/Timed-25-Foot-Walk-(T25-FW) (last visited Aug. 31, 2015).
IPR 2015-01857 (ADROCA '685 IPR II) Exhibit 1042—U.S. Appl. No. 60/528,760, filed Dec. 11, 2003 ("'760 Provisional").
IPR 2015-01857 (ADROCA '685 IPR II) Exhibit 1043—Claim Charts for the '685 Patent.
IPR 2015-01857 (ADROCA '685 IPR II) Exhibit 1044—U.S. Appl. No. 60/528,592, filed Dec. 11, 2003 ("'592 Provisional").
IPR 2015-01857 (ADROCA '685 IPR II) Exhibit 1045—U.S. Appl. No. 60/528,593, filed Dec. 11, 2003 ("'593 Provisional").
IPR 2015-01857 (ADROCA '685 IPR II) Exhibit 1046—Orange Book Listing for '826 Patent ("Orange Book").
IPR 2015-01857 (ADROCA '685 IPR II) Exhibit 1047—C.T. Bever, Jr., MD, et al., "The effects of 4-aminopyridine in multiple sclerosis patients: Results of a randomized, placebo-controlled, double-blind, concentration-controlled, crossover trial," 1054 Neurology No. 44, Jun. 1994, at 1054-59 ("Bever").
IPR 2015-01857 (ADROCA '685 IPR II) Exhibit 1048—Andrew R. Blight & Ron Cohen, U.S. Pat. No. 8,354,437 (filed Apr. 8, 2005) (issued Jan. 15, 2013) ("the '437 Patent").
IPR 2015-01857 (ADROCA '685 IPR II) Exhibit 1049—Relevant excerpts of U.S. Pat. No. 8,007,826 Prosecution History ("'826 prosecution history").
IPR 2015-01857 (ADROCA '685 IPR II) Exhibit 1050—Andrew R. Blight & Ron Cohen, U.S. Pat. No. 8,007,826 (filed Dec. 13, 2004) (issued Aug. 30, 2011) ("the '826 Patent").
IPR 2015-01857 (ADROCA '685 IPR II) Exhibit 1051—Declaration of James Polli, Ph.D. ("Polli Decl.").
IPR 2015-01857 (ADROCA '685 IPR II) Exhibit 1052—CV of James Polli ("Polli CV").
IPR 2015-01857 (ADROCA '685 IPR II) Exhibit 1053—Relevant excerpts of U.S. Pat. No. 8,007,826 Prosecution History—Part 2 ("'826 prosecution history").
PTAB Decision on Institution of IPR on U.S. Pat. No. 8,663,685 issued Mar. 11, 2016 in the ADROCA '685 IPR II (IPR2015-01857).
Petitioner's Reply to Patent Owner's Response (Redacted) filed Sep. 29, 2016 by the Coalition for Affordable Drugs (ADROCA) LLC in the ADROCA '685 IPR II (IPR2015-01857).
Petitioner's Current Exhibit List filed Sep. 29, 2016 by the Coalition for Affordable Drugs (ADROCA) LLC in the ADROCA '685 IPR II (IPR2015-01857).
IPR 2015-01857 (ADROCA '685 IPR II) Exhibit 1061—Charles Weijer, 2000, "The ethical analysis of risk," Journal of Law, Medicine, & Ethics, 28(4):344-361.
IPR 2015-01857 (ADROCA '685 IPR II) Exhibit 1062—"What are the different types of clinical research?," http://www.fda.gov/ForPatients/ClinicalTrials/Types/ucm20041762.htm (last visited Sep. 7, 2016).
IPR2015-01857 (ADROCA '685 IPR II) Exhibit 1063—"Electronic code of federal regulations," http://www.ecfr.gov/cgi-bin/text-idx?SID=d428bea027fdf18fa4b31dc68ed5e918&mc=true&node=pt21.5.312&rgn=div5πsp21.5.312a (last visited Sep. 7, 2016).
IPR 2015-01857 (ADROCA '685 IPR II) Exhibit 1064—Lee et al., 2005, "Evidence of effectiveness: how much can we extrapolate from existing studies?," The AAPS Journal, 7(2):E467-E474.
IPR2015-01857 (ADROCA '685 IPR II) Exhibit 1065—Lesko et al., 2000, "Optimizing the science of drug development: opportunites for better candidate selection and accelerated evaluation in humans," Eur. J. Pharm. Sci., 10:iv-xiv.
IPR 2015-01857 (ADROCA '685 IPR II) Exhibit 1067—Relevant excerpts of U.S. Pat. No. 8,007,826 Prosecution History ("'826 prosecution history").
IPR2015-01857 (ADROCA '685 IPR II) Exhibit 1072—Declaration of Samuel J. Pleasure.
IPR2015-01857 (ADROCA '685 IPR II) Exhibit 1073—Declaration of William R. Fairweather, Ph.D., PSTAT.
IPR2015-01857 (ADROCA '685 IPR II) Exhibit 1074—Declaration of Carrie L. Distler (Redacted).
IPR2015-01857 (ADROCA '685 IPR II) Exhibit 1075—CV of William R. Fairweather, Ph.D., PSTAT.
IPR2015-01857 (ADROCA '685 IPR II) Exhibit 1076—Deposition of Keith C. Hayes, Ph.D.
IPR2015-01857 (ADROCA '685 IPR II) Exhibit 1077—CV of Carrie Distler.
IPR2015-01857 (ADROCA '685 IPR II) Exhibit 1078—Hoogstraten et al., 1988, "Tizanidine versus baclofen in the treatment of spasticity in multiple sclerosis patients," Acta. Neurol. Scand., 77:224-230.
IPR2015-01857 (ADROCA '685 IPR II) Exhibit 1079—Norman et al., 1998, "Effects of drugs on walking after spinal cord injury," Spinal Cord, 36:699-715.

(56) References Cited

OTHER PUBLICATIONS

IPR2015-01857 (ADROCA '685 IPR II) Exhibit 1080—Knutsson et al., 1982, "Antiparetic and antispastic effects induced by tizanidine in patients with spastic paresis," J. Neurol. Sci., 53:187-204.
IPR2015-01857 (ADROCA '685 IPR II) Exhibit 1081—"Comprehensive Care: National Multiple Sclerosis Society," http://www.nationalmssociety.org/Treating-MS/Comprehensive-Care (last visited Sep. 28, 2016).
IPR2015-01857 (ADROCA '685 IPR II) Exhibit 1082—Nadeau et al., 2011, "Acorda Therapeutics—Q1 Light; ACOR remains undervalued despite estimate changes," Cowen and Company, 8 pages.
IPR2015-01857 (ADROCA '685 IPR II) Exhibit 1083—"Medications: National Multiple Sclerosis Society," http://www.nationalmssociety.org/TreatingMS/Medications (last visited Aug. 12, 2016).
IPR2015-01857 (ADROCA '685 IPR II) Exhibit 1074—Corrected Declaration of Carrie L. Distler (Redacted).
Petition for Inter Partes Review of U.S. Pat. No. 8,354,437 filed Sep. 3, 2015 by the Coalition for Affordable Drugs (ADROCA) LLC ("ADROCA '437 IPR") (IPR2015-01858).
IPR 2015-01858 (ADROCA '437 IPR) Exhibit 1001—Andrew R. Blight & Ron Cohen, U.S. Pat. No. 8,354,437 (filed Apr. 8, 2005) (issued Jan. 15, 2013) ("the '437 Patent").
IPR 2015-01858 (ADROCA '437 IPR) Exhibit 1002—Relevant excerpts of U.S. Pat. No. 8,354,437 Prosecution History ("'437 prosecution history")—Part 1.
IPR 2015-01858 (ADROCA '437 IPR) Exhibit 1003—Acorda Therapeutics, Inc., Registration Statement Under the Securities Act of 1933 (Form S-1) (Sep. 26, 2003) ("S-1").
IPR 2015-01857 (ADROCA '437 IPR) Exhibit 1004—Rules and Related Matters, 2003-186 (Sep. 30, 2003), available at http://www.sec.gov/news/digest/dig093003.txt ("S-1 Registration Statement").
IPR 2015-01858 (ADROCA '437 IPR) Exhibit 1005—Keith C. Hayes et al., "Pharmacokinetic Studies of Single and Multiple Oral Doses of Fampridine-SR (Sustained-Release 4-Aminopyridine) in Patients With Chronic Spinal Cord Injury," 26 Clinical Neuropharmacology, No. 4, at 185-192 (2003) ("Hayes").
IPR 2015-01858 (ADROCA '437 IPR) Exhibit 1006—Haydee Juárez et al., "Influence of Admixed Carboxymethylcellulose on Release of 4-Aminopyridine from Hydroxypropyl Methylcellulose Matrix Tablets," 216 Int'l J. Pharm., 2001, at 115-25 ("Juarez").
IPR 2015-01858 (ADROCA '437 IPR) Exhibit 1007—U.S. Appl. No. 60/560,894, filed Apr. 9, 2004 ("the Provisional").
IPR 2015-01858 (ADROCA '437 IPR) Exhibit 1008—Masterson et al., U.S. Pat. No. 5,540,938, "Formulations and Their Use in the Treatment of Neurological Diseases" (filed Oct. 24, 1994) ("Masterson").
IPR 2015-01858 (ADROCA '437 IPR) Exhibit 1009—Schwid et al., "Quantitative Assessment of Sustained Release 4-Aminopyridine for Symptomatic Treatment of Multiple Sclerosis," 48 Neurol., No. 4, at 817-21 (Apr. 1997) ("Schwid").
IPR 2015-01858 (ADROCA '437 IPR) Exhibit 1010—Richard E. Jones et al.,"Effects of 4-Aminopyridine in Patients with Multiple Sclerosis," 60 J. Neurol. Sci. at 353-62 (1983).
IPR 2015-01858 (ADROCA '437 IPR) Exhibit 1011—Harriët van Diemen, M.D. et al., "The Effect of 4-Aminopyridine on the Clinical Signs in Multiple Sclerosis: A Randomized, Placebo-Controlled, Double-Blind, Cross-over Study," 32 Annals Neurol., No. 2, at 123-30 (Aug. 1992) ("van Diemen").
IPR 2015-01858 (ADROCA '437 IPR) Exhibit 1012—Chris H. Polman, M.D., Ph.D. et al., "4-Aminopyridine is Superior to 3,4-Diaminopyridine in the Treatment of Patients With Multiple Sclerosis," 51 Arch. Neurol., No. 11, at 1136-39 (Nov. 1994) ("Polman").
IPR 2015-01858 (ADROCA '437 IPR) Exhibit 1013—D. Stefoski, M.D. et al., "4-Aminopyridine Improves Clinical Signs in Multiple Sclerosis," 21 Annals Neurol., No. 1, at 71-77 (1987).
IPR 2015-01858 (ADROCA '437 IPR) Exhibit 1014—Floyd A. Davis, M.D. et al., "Orally Administered 4-Aminopyridine Improves Clinical Signs in Multiple Sclerosis," 27 Annals Neurol., No. 2, at 186-92 (Feb. 1990).
IPR 2015-01858 (ADROCA '437 IPR) Exhibit 1015—Types of MS, Nat. Multiple Sclerosis Soc'y, http://www.nationalmssociety.org/What-is-MS/Types-of-MS (last visited Aug. 11, 2015) ("NMSS").
IPR 2015-01858 (ADROCA '437 IPR) Exhibit 1016—Declaration of Scott Bennett ("Bennett Decl.").
IPR 2015-01858 (ADROCA '437 IPR) Exhibit 1017—C. Darlington, Abstract, Fampridine Acorda Therapeutics, 1 Current Opinions in Investigational Drugs, No. 3, Nov. 2000, at 375-79.
IPR 2015-01858 (ADROCA '437 IPR) Exhibit 1018—Porter Novelli, "Acorda Therapeutics Begins Phase 3 Trials of Fampridine-SR for Chronic Spinal Cord Injury," American Association for the Advancement of Science (AAAS) EurekAlert! (Jul. 1, 2002), http://www.eurekalert.org/pub_releases/2002-07/pn-atb062802.php.
IPR 2015-01858 (ADROCA '437 IPR) Exhibit 1019—Acorda Therapeutics Company Profile, Biospace, http://www.biospace.com/company_profile.aspx?CompanyId=100704 (last updated May 9, 2003).
IPR 2015-01858 (ADROCA '437 IPR) Exhibit 1020—Goodman et al., "Placebo-Controlled Double-Blinded Dose Ranging Study of Fampridine-SR in Multiple Sclerosis," poster presented at the 7th Annual Meeting of the Americas Committee for Treatment and Research in Multiple Sclerosis and 18th Congress of the European Committee for Treatment and Research in Multiple Sclerosis (ACTRIMS/ECTRIMS), Sep. 18-21, 2002, Baltimore, MD ("Goodman").
IPR 2015-01858 (ADROCA '437 IPR) Exhibit 1021—European Patent Convention art. 54(1), (2), Oct. 5, 1973, 1065 U.N.T.S. 199 (as amended Nov. 29, 2000), available at http://www.epo.org/law-practice/legal-texts/html/epc/2010/e/ar54.html-texts/html/epc/2010/e/ar54.html ("EPC Art. 54").
IPR 2015-01858 (ADROCA '437 IPR) Exhibit 1022—Fred D. Lublin, M.D. & Stephen C. Reingold Ph.D., "Defining the Clinical Course of Multiple Sclerosis: Results of an International Survey," 46 Neurology, No. 4, at 907-11 (Apr. 1996).
IPR 2015-01858 (ADROCA '437 IPR) Exhibit 1023—Declaration of Samuel J. Pleasure, M.D., Ph.D. ("Pleasure Decl.").
IPR 2015-01858 (ADROCA '437 IPR) Exhibit 1024—CV of Samuel J. Pleasure, M.D., Ph.D. ("Pleasure CV").
IPR 2015-01858 (ADROCA '437 IPR) Exhibit 1025—European Patent No. 1 732 548 (B9) ("EP 548").
IPR 2015-01858 (ADROCA '437 IPR) Exhibit 1026—Excerpts from Proprietor's Response to Opponents' Appeals, European Patent No. 1 732 548 B9, filed with the EPO, Sep. 16, 2004 ("Acorda EP Brief").
IPR 2015-01858 (ADROCA '437 IPR) Exhibit 1027—European Patent Office, Espacenet Brochure, http://documents.epo.org/projects/babylon/eponet.nsf/0/4E8744EB66E8F944C12577D600598EEF/$File/espacenet_brochure_en.pdf ("Espacenet Brochure").
IPR 2015-01858 (ADROCA '437 IPR) Exhibit 1028—Espacenet Bibliographic Data for U.S. Pat. No. 8,354,437.
IPR 2015-01858 (ADROCA '437 IPR) Exhibit 1029—CV of Scott Bennett.
IPR 2015-01858 (ADROCA '437 IPR) Exhibit 1030—Bennett Decl. Attachment 1.
IPR 2015-01858 (ADROCA '437 IPR) Exhibit 1031—Bennett Decl. Attachment 2.
IPR 2015-01858 (ADROCA '437 IPR) Exhibit 1032—Bennett Decl. Attachment 3.
IPR 2015-01858 (ADROCA '437 IPR) Exhibit 1033—Bennett Decl. Attachment 4.
IPR 2015-01858 (ADROCA '437 IPR) Exhibit 1034—Bennett Decl. Attachment 5.
IPR 2015-01858 (ADROCA '437 IPR) Exhibit 1035—Bennett Decl. Attachment 6.
IPR 2015-01858 (ADROCA '437 IPR) Exhibit 1036—Bennett Decl. Attachment 7.

(56) References Cited

OTHER PUBLICATIONS

IPR 2015-01858 (ADROCA '437 IPR) Exhibit 1037—Bennett Decl. Attachment 8.
IPR 2015-01858 (ADROCA '437 IPR) Exhibit 1038—Bennett Decl. Attachment 9.
IPR 2015-01858 (ADROCA '437 IPR) Exhibit 1039—Stephen L. Hauser, M.D. & Donald E. Goodkin, Harrison's Principles of Internal Medicine, 2452-61, 15th ed. 2001.
IPR 2015-01858 (ADROCA '437 IPR) Exhibit 1040—Christian Confavreux, M.D. et al, "Relapses and Progression of Disability in Multiple Sclerosis," 343 New Eng. J. Med., No. 20, at 1430-38 (Nov. 16, 2000).
IPR 2015-01858 (ADROCA '437 IPR) Exhibit 1041—Timed 25-Foot Walk (T25-FW), Nat'l Multiple Sclerosis Soc'y Website, http://www.nationalmssociety.org/For-Professionals/Researchers/Resources-for-Researchers/Clinical-Study-Measures/Timed-25-Foot-Walk-(T25-FW) (last visited Aug. 31, 2015).
IPR 2015-01858 (ADROCA '437 IPR) Exhibit 1043—Pleasure Decl. and Polli Decl. Attachment 2 (Claim Charts for the '437 Patent).
IPR 2015-01858 (ADROCA '437 IPR) Exhibit 1044—Declaration of Dr. James Polli, Ph.D. ("Polli Decl.").
IPR 2015-01858 (ADROCA '437 IPR) Exhibit 1045—CV of Dr. James Polli, Ph.D. ("Polli CV").
IPR 2015-01858 (ADROCA '437 IPR) Exhibit 1046—Relevant excerpts of U.S. Pat. No. 8,354,437 Prosecution History ("'437 prosecution history")—Part 2.
IPR 2015-01858 (ADROCA '437 IPR) Exhibit 1047—Relevant excerpts of U.S. Pat. No. 8,354,437 Prosecution History ("'437 prosecution history")—Part 3.
IPR 2015-01858 (ADROCA '437 IPR) Exhibit 1048—Relevant excerpts of U.S. Pat. No. 8,354,437 Prosecution History ("'437 prosecution history")—Part 4.
IPR 2015-01858 (ADROCA '437 IPR) Exhibit 1049—Relevant excerpts of U.S. Pat. No. 8,354,437 Prosecution History ("'437 prosecution history")—Part 5.
IPR 2015-01858 (ADROCA '437 IPR) Exhibit 1050—Relevant excerpts of U.S. Pat. No. 8,354,437 Prosecution History ("'437 prosecution history")—Part 6.
PTAB Decision on Institution of IPR on U.S. Pat. No. 8,354,437 issued Mar. 11, 2016 in the ADROCA '437 IPR (IPR2015-01858).
Petitioner's Reply to Patent Owner's Response (Redacted) filed Sep. 29, 2016 by the Coalition for Affordable Drugs (ADROCA) LLC in the ADROCA '437 IPR (IPR2015-01858).
Petitioner's Current Exhibit List filed Sep. 29, 2016 by the Coalition for Affordable Drugs (ADROCA) LLC in the ADROCA '437 IPR (IPR2015-01858).
IPR2015-01858 (ADROCA '437 IPR) Exhibit 1057—Charles Weijer, 2000, "The ethical analysis of risk," Journal of Law, Medicine, & Ethics, 28(4):344-361.
IPR2015-01858 (ADROCA '826 IPR) Exhibit 1058—"What are the different types of clinical research?," http://www.fda.gov/ForPatients/ClinicalTrials/Types/ucm20041762.htm (last visited Sep. 7, 2016).
IPR2015-01858 (ADROCA '437 IPR) Exhibit 1059—"Electronic code of federal regulations," http://ecfr.gov/cgi-bin/text-idx?SID=d428bea027fdf18fa4b31dc68ed5e918&mc=true&node=pt21.5.312&rgn=div5#sp21.5.312a (last visited Sep. 7, 2016).
IPR2015-01858 (ADROCA '437 IPR) Exhibit 1060—Lee et al., 2005, "Evidence of effectiveness: how much can we extrapolate from existing studies?," The AAPS Journal, 7(2):E467-E474.
IPR2015-01858 (ADROCA '437 IPR) Exhibit 1061—Lesko et al., 2000, "Optimizing the science of drug development: opportunites for better candidate selection and accelerated evaluation in humans," Eur. J. Pharm. Sci., 10:iv-xiv.
IPR2015-01858 (ADROCA '437 IPR) Exhibit 1063—Relevant excerpts of U.S. Pat. No. 8,007,826 Prosecution History ("'826 prosecution history").
IPR2015-01858 (ADROCA '437 IPR) Exhibit 1068—Declaration of Samuel J. Pleasure.
IPR2015-01858 (ADROCA '437 IPR) Exhibit 1069—Declaration of William R. Fairweather, Ph.D., PSTAT.
IPR2015-01858 (ADROCA '437 IPR) Exhibit 1070—Declaration of Carrie L. Distler (Redacted).
IPR2015-01858 (ADROCA '437 IPR) Exhibit 1071—CV of William R. Fairweather, Ph.D., PSTAT.
IPR2015-01858 (ADROCA '437 IPR) Exhibit 1072—Deposition of Keith C. Hayes, Ph.D.
IPR2015-01858 (ADROCA '437 IPR) Exhibit 1073—CV of Carrie Distler.
IPR2015-01858 (ADROCA '437 IPR) Exhibit 1074—Hoogstraten et al., 1988, "Tizanidine versus baclofen in the treatment of spasticity in multiple sclerosis patients," Acta. Neurol. Scand., 77:224-230.
IPR2015-01858 (ADROCA '437 IPR) Exhibit 1075—Norman et al., 1998, "Effects of drugs on walking after spinal cord injury," Spinal Cord, 36:699-715.
IPR2015-01858 (ADROCA '437 IPR) Exhibit 1076—Knutsson et al., 1982, "Antiparetic and antispastic effects induced by tizanidine in patients with spastic paresis," J. Neurol. Sci., 53:187-204.
IPR2015-01858 (ADROCA '437 IPR) Exhibit 1077—"Comprehensive Care: National Multiple Sclerosis Society," http://www.nationalmssociety.org/Treating-MS/Comprehensive-Care (last visited Sep. 28, 2016).
IPR2015-01858 (ADROCA '437 IPR) Exhibit 1078—Nadeau et al., 2011, "Acorda Therapeutics—Q1 Light; ACOR remains undervalued despite estimate changes," Cowen and Company, 8 pages.
IPR2015-01858 (ADROCA '437 IPR) Exhibit 1079—"Medications: National Multiple Sclerosis Society," http://www.nationalmssociety.org/TreatingMS/Medications (last visited Aug. 12, 2016).
IPR2015-01858 (ADROCA '437 IPR) Exhibit 1070—Corrected Declaration of Carrie L. Distler (Redacted).
PTAB Final Written Decision re U.S. Pat. No. 8,440,703; 8,007,826; 8,663,685; and 8,354,437, issued Mar. 9, 2017, in the ADROCA '703, '826, '685, and '437 IPRs (IPR2015-01850, IPR2015-01853, IPR2015-01857, IPR2015-01858, respectively).
Notice Letter and Detailed Factual and Legal Bases for Micro Labs, Ltd.'s Paragraph IV Certification dated Apr. 12, 2017.
Halliday et al., 1973, "Visual evoked response in diagnosis of multiple sclerosis," Br. Med J. 4(5893):661-664.
Chang et al., 1990, "Sustained Drug Release from Tablets and Particles Through Coating," Chapter 4 of *Pharmaceutical Dosage Forms*: Tablets, vol. 3, Lieberman et al. Eds, 2$^{nd}$ Ed., pp. 199-302 (Textbook, ISBN 0-8247-8300-X).
Corrected Brief of Apellant Acorda Therapeutics, Inc., filed Aug. 9, 2017, in *Acorda Therapeutics, Inc., et al.* v. *Roxane Laboratories, Inc., et al.*, Docket No. 17-02078 (Fed. Cir. May 24, 2017).
Apellant Acorda Therapeutics, Inc.'s Notice of Correction, filed Aug. 9, 2017, in *Acorda Therapeutics, Inc., et al.* v. *Roxane Laboratories, Inc., et al.*, Docket No. 17-02078 (Fed. Cir. May 24, 2017).
Raffel et al., 2014, "Assessing dalfampridine efficacy in the physician's office," Multiple Sclerosis Journal 20(I):24-26.
Reply Brief of Acorda Therapeutics, Inc. and Response Brief of Acorda Therapeutics, Inc. and Alkermes Pharma Ireland Limited (Corrected), filed Nov. 15, 2017, in *Acorda Therapeutics, Inc., et al.* v. *Roxane Laboratories, Inc., et al.*, Court of Appeals for the Federal Circuit, Docket No. 17/2078.
Letter to Peter K. Marksteiner under Rule 28(j) from Cross-Appellants Mylan Pharmaceuticals Inc., Roxane Laboratories, Inc. and Teva Pharmaceuticals USA, Inc., filed Nov. 20, 2017, in *Acorda Therapeutics, Inc., et al.* v. *Roxane Laboratories, Inc., et al.*, Court of Appeals for the Federal Circuit, Docket No. 17/2078.
Reply Brief for Defendants-Cross-Appellants Roxane Laboratories, Inc., Mylan Pharmaceuticals Inc., Teva Pharmaceuticals USA, Inc., filed Nov. 27, 2017, in *Acorda Therapeutics, Inc., et al.* v. *Roxane Laboratories, Inc., et al.*, Court of Appeals for the Federal Circuit, Docket No. 17/2078.
Third Party Observation filed Oct. 24, 2017 for European Patent Application No. EP2422782.

(56) References Cited

OTHER PUBLICATIONS

Briefs for Defendants-Appellees and Cross-Appellants Roxane Laboratories, Inc., Mylan Pharmaceuticals, Inc., Teva Pharmaceuticals USA, Inc. (Corrected), filed on Oct. 6, 2017, Court of Appeals for the Federal Circuit, Docket No. 17-02078.

Magosso et al., 2004, "Comparative Bioavailability Study of a Generic Sustained Release Diclofenac Sodium Tablet," Med J Malaysia 59(3):352-356.

Communication dated Jul. 19, 2017, withThind Party Observations filed Jul. 13, 2017 for European Patent Application No. 11179067.1.

Note: The treatment sample sizes are based on the number of ITT subjects with available data.
Note: The p-values (versus placebo) presented above the treatment mean bars are Dunnett-adjusted Note: The treatment sample sizes are based on the number of ITT subjects with available data.

Note: The treatment sample sizes are based on the number of ITT subjects with available data.
Note: The p-values (versus placebo) presented above the treatment mean bars are Dunnett-adjusted

*Change from baseline in the MSWS-12 over the double-blind**

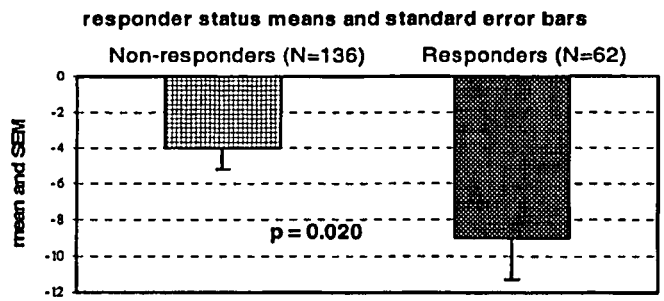

*SGI over the double-blind*

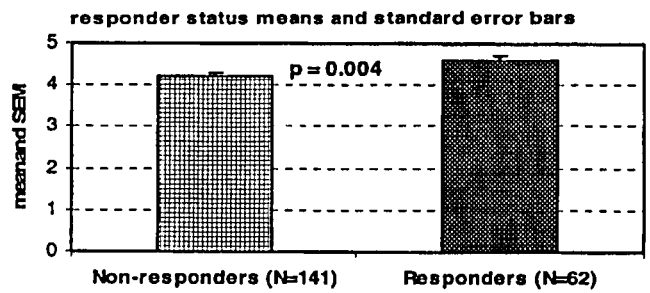

*Change from baseline in the CGI over the double-blind*

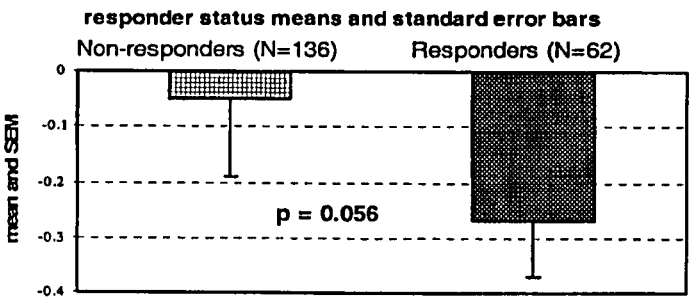

•Double blind measurements at first and last stable dose visits only.
•Note: For the changes from baseline, a negative score is indicative of clinical benefit.
•Note: Some non-responders had no post-baseline data for a particular variable; so the sample sizes for the non-responders (with respect to that variable) may be less than the actual number of non-responders.
•Note: the p-values comparing responders to non-responders are from ANOVA models with effects for responder status and center.

Fig. 9

METHODS OF USING SUSTAINED RELEASE AMINOPYRIDINE COMPOSITIONS

CROSS REFERENCES

This application is a continuation of U.S. patent application Ser. No. 15/344,096, filed Nov. 4, 2016, which is a continuation of U.S. patent application Ser. No. 15/079,010, filed Mar. 23, 2016, which is a continuation of U.S. patent application Ser. No. 14/531,191, filed Nov. 3, 2014, which is a continuation of U.S. patent application Ser. No. 13/829,221, filed Mar. 14, 2013, which is a continuation of U.S. patent application Ser. No. 13/410,388, filed Mar. 2, 2012, which is a continuation of U.S. patent application Ser. No. 11/102,559, filed Apr. 8, 2005, now U.S. Pat. No. 8,354,437 B2, which claims the benefit of U.S. Provisional Application No. 60/560,894, filed Apr. 9, 2004. U.S. patent application Ser. No. 11/102,559, U.S. patent application Ser. No. 13/410,388, U.S. patent application Ser. No. 13/829,221, U.S. patent application Ser. No. 14/531,191, U.S. patent application Ser. No. 15/079,010, and U.S. patent application Ser. No. 15/344,096 are incorporated by reference herein in their entireties.

BACKGROUND

This invention relates a sustained release oral dosage form of an aminopyridine pharmaceutical composition that can be used to treat individuals affected with neurological disorders wherein said pharmaceutical composition maximizes the therapeutic effect, while minimizing adverse side effects.

The sustained release oral dosage form of the present invention may be utilized to treat neurological disorders such as multiple sclerosis, spinal cord injuries, Alzheimer's disease and ALS.

Multiple sclerosis (MS) is a degenerative and inflammatory neurological disease that affects the central nervous system, more specifically the myelin sheath. The condition of MS involves demyelination of nerve fibers resulting in "short-circuiting" of nerve impulses and thus a slowing or blocking of transmission along the nerve fibers, with associated disabling symptoms. Treatment alternatives for promoting transmission along affected nerves have thus far been limited.

Potassium channel blockers are a class of compounds that has been found to improve the conduction of nerve impulses. As a result, they have become the focus of attention in the symptomatic treatment of spinal cord injury, MS and Alzheimer's disease. One sub-class of potassium channel blockers, aminopyridines have shown promise in the treatment of neurological diseases. 4-aminopyridine (4-AP), a mono-aminopyridine known as fampridine, has been found to reduce the potassium flow in nerve impulse transmission and, thereby, shows effectiveness in restoring conduction in blocked and demyelinated nerves.

Early studies of monoaminopyridines were conducted using an intravenous composition, comprising 4-AP. This was followed by the development of an immediate-release (IR) composition for oral administration of 4-AP, commonly known as fampridine. The IR composition consisted of 4-AP powder in a gelatin-based capsule and produced rapid peak plasma concentrations shortly after dosing with a time to maximum concentration of about 1 hour and a plasma half life of about 3.5 hours. The rapid release and short half life of fampridine makes it difficult to maintain effective plasma levels without producing high peaks following each dose that may cause undesirable side effects such as seizures and trembling.

Electrophysiological recordings from isolated spinal cord have shown chronic failure of action potential conduction in surviving myelinated axons, following a blunt contusion injury (Blight, A. R., "Axonal physiology of chronic spinal cord injury in the cat: intracellular recording in vitro", Neuroscience. 10:1471-1486 (1983b)). Some of this conduction block can be overcome, at the level of single nerve fibers, using the drug 4-aminopyridine (4-AP) (Blight, A. R., "Effect of 4-aminopyridine on axonal conduction-block in chronic spinal cord injury", Brain Res. Bull. 22:47-52 (1989)). Intravenous injection of this compound in animals with experimental or naturally occurring spinal cord injuries produces significant improvements in electrophysiological (Blight, A. R. and Gruner, J. A., "Augmentation by 4-aminopyridine of vestibulospinal free fall responses in chronic spinal-injured cats," J. Neurol. Sci. 82:145-159, (1987)) and behavior function (Blight, A. R., "The effects of 4-aminopyridine on neurological deficits in chronic cases of traumatic spinal cord injury in dogs: a phase I clinical trial," J. Neurotrauma, 8:103-119 (1991)).

An initial study in spinal cord injury patients was organized by Dr. Keith Hayes and indicated a potential for a therapeutic benefit, mostly at the electrophysiological level, combined with a lack of serious side effects (Hayes et al, "Effects of intravenous 4-aminopyridine on neurological function in chronic spinal cord injured patients: preliminary observations," Proc. IBRO World Conf. Neurosci., p. 345 1991).

A recent study of fampridine in patients with chronic incomplete SCI was reported in Clinical Neuropharmacology 2003: Keith C. Hayes; Patrick J. Potter; Robert R. Hansebout; Joanne M. Bugaresti; Jane T. C. Hsieh; Sera Nicosia; Mitchell A. Katz; Andrew R. Blight; Ron Cohen 26(4):185-192.

SUMMARY OF THE INVENTION

One embodiment of the present invention relates to a pharmaceutical composition which contains one or more potassium channel blockers and which can be used in the effective treatment of various diseases, for example, spinal cord injury, multiple sclerosis, Alzheimer's disease, and ALS. Embodiments of the present invention are directed to compositions that include a matrix and a potassium channel blocker. The potassium channel blockers may include aminopyridines, for example, 4-aminopyridine, 3,4-diaminopyridine and the like, most preferably 4-aminopyridine. The composition provides for sustained-release of the aminopyridine from the matrix to maintain the efficacious and safe plasma level of an aminopyridine. The aminopyridine dispersed in the matrix is capable of providing, upon administration to a patient, a desired release profile. The composition may be used to establish in patients in need of such treatment, a therapeutically effective blood plasma level of the aminopyridine for a period of at least about 6 hours and preferably up to at least about 12 hours in the patient in a twice-daily administration while avoiding excessive peaks and troughs in the level of the aminopyridine. The composition may include a mono- or di-aminopyridine, preferably 4-AP or 3,4-DAP or a combination thereof, homogeneously dispersed in a rate-controlling polymer matrix, preferably including a hydrophilic polymer like hydroxypropylmethylcellulose (HPMC). The composition of the present invention may also include one or more additional active ingredients and/or one or more pharmaceutically acceptable excipients. These compositions can be used to treat various neurological diseases, for example, spinal cord injury, multiple sclerosis, Alzheimer's disease, and ALS.

Another embodiment of the present invention is a stable pharmaceutical composition that comprises a therapeutically effective amount of an aminopyridine dispersed in a matrix that provides a release profile of the aminopyridine to a patient that has a desired $C_{max}$ to $C_\tau$ ratio. The composition may be used to establish and/or maintain in a patient, a therapeutically effective level of the aminopyridine. Preferably the aminopyridine in the composition is released over time so that a therapeutically effective level of the aminopyridine in the patient can be achieved with twice daily dosing of the composition. In a more preferred embodiment, undesirable spikes or peaks in the release of the aminopyridine are avoided.

Another embodiment of the present invention is a stable, sustained-release oral dosage formulation of a composition which includes a therapeutically effective amount of a 4-aminopyridine dispersed in a matrix that provides a release profile of 4-aminopyridine in the blood plasma of the patient extending over a period of at least 6 hours, preferably at least 8 hours, and more preferably, at least about 12 hours. In another embodiment, a stable, sustained-release oral dosage formulation of a composition includes a therapeutically effective amount of a 4-aminopyridine dispersed in a matrix that provides a therapeutically effective blood plasma level of 4-aminopyridine in the patient extending over about 24 hours.

Preferably, the oral dosage formulation of the composition is a monolithic tablet formed by compression of the pharmaceutical composition of the present invention. In preferred embodiments, the oral dosage formulation includes a compressed tablet of a therapeutically effective amount of 4-aminopyridine dispersed in matrix that includes a hydrophilic polymer such as HPMC. The oral dosage form of the present invention may also include one or more pharmaceutically acceptable excipients.

The dispersion of 4-aminopyridine throughout the matrix imparts chemical and physical stability to the composition while providing a sustained-release profile. This enhanced dosage stability is most notably observed in compositions and dosage forms of the present invention having low concentrations of 4-aminopyridine, and stability is achieved while maintaining the desired controlled-release profile. Specifically, the compressed tablet formulation of the present invention exhibits superior resistance to moisture absorption by ambient humidity and maintains a uniform distribution of the 4-aminopyridine throughout the tablet while providing a release profile of 4-aminopyridine that permits establishment of a therapeutically effective concentration of the potassium channel blocker with once daily or twice daily dosing of the formulation. Preferably the therapeutically effective concentration released by the formulation extends over at least about 6 hours, preferably at least about 8 hours, and more preferably at least about 12 hours. In addition, the homogeneity of the dosage form renders it amenable to formation by simple and inexpensive manufacturing processes as compared with the multi-layered structure of prior sustained-release dosage formulations.

The compositions of the present invention may be used in the treatment of a condition in a patient that includes establishing a therapeutically effective concentration of a potassium channel blocker in the patient in need thereof. The compositions may be used for building up a level and or maintaining a therapeutically effective concentration of an aminopyridine in the patient by twice daily dosing. The dosages of the present compositions can be made with a lower concentration of the aminopyridine to facilitate restful periods for the patient during the day or night, depending on desired results or dosage schedule. Where desirable, the compositions of the present invention may be formulated to avoid large peaks in initial release of the aminopyridine. The compositions of the present invention when administered to a patient in need thereof provide for the treatment of neurological diseases that are characterized by a degradation of nerve impulse transmission. Preferably, the compositions are a stable, sustained-release tablet of a therapeutically effective amount of a mono- or di-aminopyridine, dispersed in HPMC such that therapeutically effective blood plasma level of the mono- or di-aminopyridine is maintained in the patient for a period of at least 6 hours, preferably at least 8 hours, and more preferably at least about 10-12 hours in a once or twice daily administration.

One embodiment of the present invention relates to a method of increasing walking speed comprising administering to a patient with multiple sclerosis an effective amount of a sustained release aminopyridine composition twice daily, wherein said effective amount is less than about 15 milligrams of aminopyridine. In a preferred embodiment, the effective amount is about 10 to about 15 milligrams of aminopyridine.

In a further embodiment of the present invention a method of improving lower extremity muscle tone comprising administering to a patient with multiple sclerosis an effective amount of a sustained-release aminopyridine composition twice daily is provided. In a preferred embodiment, said effective amount is less than about 15 milligrams of aminopyridine.

Another embodiment of the present invention relates to a method of improving lower extremity muscle strength comprising administering to a patient with multiple sclerosis an effective amount of a sustained-release aminopyridine composition twice daily, wherein said effective amount is less than about 15 milligrams of aminopyridine.

One embodiment of the present invention relates to a method of selecting individuals based on responsiveness to a treatment. The method comprises identifying a plurality of individuals; administering a test to each individual prior to a treatment period; administering a treatment to one or more of the individuals during the treatment period; administering the test a plurality of times to each individual during the treatment period; and selecting one or more individuals, wherein the selected individuals exhibit an improved performance during a majority of the tests administered during the treatment period as compared to the test administered prior to the treatment period. In certain embodiments, the method may further comprise administering the test to each individual after the treatment period, wherein the selected individuals further exhibit an improved performance during a majority of the tests administered during the treatment period as compared to the test administered after the treatment period.

A further embodiment relates to a method of selecting individuals based on responsiveness to a treatment, the method comprising identifying a plurality of individuals; administering a test to each individual prior to a treatment period; administering a treatment to one or more of the individuals during the treatment period; administering the test a plurality of times to each individual during the treatment period; administering the test to each individual after the treatment period; and selecting one or more individuals, wherein the selected individuals exhibit an improved performance during a majority of the tests administered during the treatment period as compared to the better performance of the test administered prior to the treatment period and the test administered after the treatment period.

BRIEF DESCRIPTION OF THE DRAWINGS

FIG. 9 are histograms of the validation of the post hoc responder variable using subjective scales (observed cases, ITT population).

DETAILED DESCRIPTION OF THE INVENTION

Figure 1:
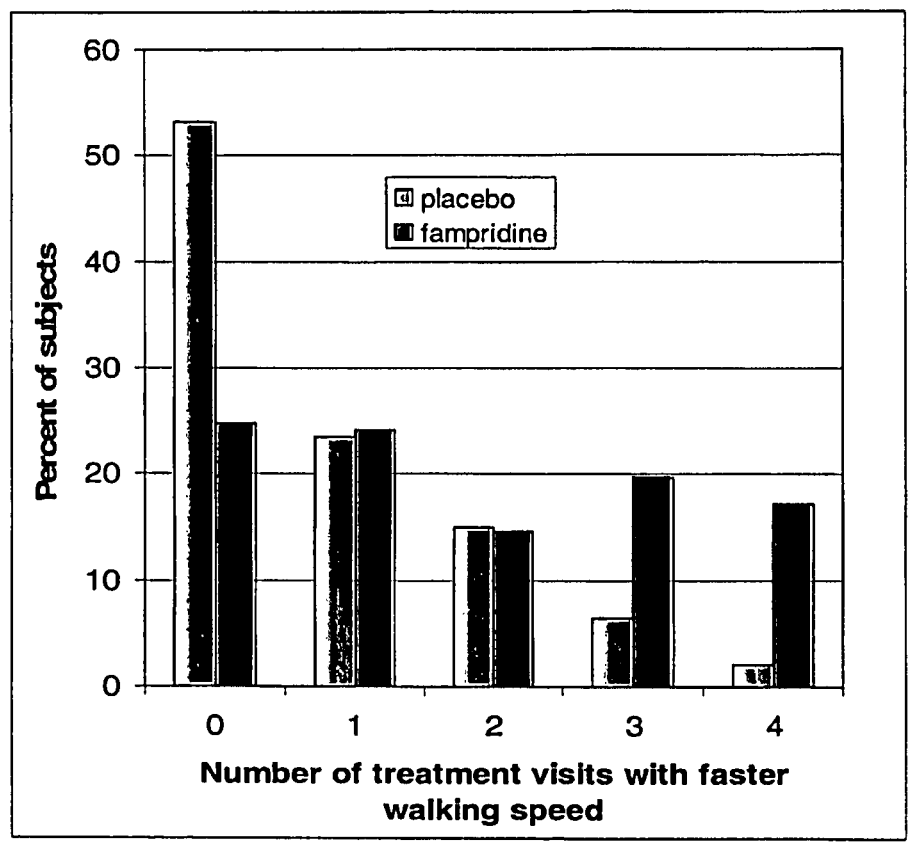
FIG. 1 is a histogram to show the number of treatment visits at which subjects showed faster walking speed on the timed 25 foot walk than at all of the five non-treatment visits.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

The terms used herein have meanings recognized and known to those of skill in the art, however, for convenience and completeness, particular terms and their meanings are set forth below.

It must also be noted that as used herein and in the appended claims, the singular forms "a", "an", and "the" include plural reference unless the context clearly dictates otherwise. Thus, for example, reference to a "spheroid" is a reference to one or more spheroid and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

"Local administration" means direct administration by a non-systemic route at or in the vicinity of the site of affliction, disorder, or perceived pain.

The terms "patient" and "subject" mean all animals including humans. Examples of patients or subjects include humans, cows, dogs, cats, goats, sheep, and pigs.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "prodrug" refers to compounds that are rapidly transformed in vivo to yield the parent compounds of the above formula, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methylamine, dimethylamine, trimethylamine, triethlyamine, ethylamine, and the like. (See, for example, S. M. Barge et al., "Pharmaceutical Salts," J. Pharm. Sci., 1977, 66:1-19 which is incorporated herein by reference.).

A "therapeutically effective amount" is an amount sufficient to decrease or prevent the symptoms associated with a medical condition or infirmity, to normalize body functions in disease or disorders that result in impairment of specific bodily functions, or to provide improvement in one or more of the clinically measured parameters of the disease. Preferably, improvement in symptoms associated with the disease including walking speed, lower extremity muscle tone, lower extremity muscle strength, or spasticity. As related to the present application, a therapeutically effective amount is an amount sufficient to reduce the pain or spasticity associated with the neurological disorder being treated, or an amount sufficient to result in improvement of sexual, bladder or bowel function in subjects having a neurological disorder which impairs nerve conduction, which hinders normal sexual, bladder or bowel functions.

"Treatment" refers to the administration of medicine or the performance of medical procedures with respect to a patient, for either prophylaxis (prevention), to cure the infirmity or malady in the instance where the patient is afflicted refers, or amelioration the clinical condition of the patient, including a decreased duration of illness or severity of illness, or subjective improvement in the quality of life of the patient or a prolonged survival of the patient.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

One aspect of the invention is a sustained-release pharmaceutical composition comprising an aminopyridine dispersed in a sustained release matrix such as a rate-controlling polymer. The composition of the present invention is capable of providing, upon administration to a patient, a release profile of the aminopyridine extending over at least 6 hours, preferably least about 12 hours, and more preferably at least 24 hours or more. Preferably the aminopyridine concentration in the composition is a therapeutically effective amount, and preferably the aminopyridine is dispersed uniformly throughout the release matrix. A therapeutically effective amount is an amount of a potassium channel blocker, preferably an aminopyridine compound, that when administered to a patient or subject, ameliorates a symptom of a neurological disease.

When the compositions of the present invention are administered to a patient, the concentration of the aminopyridine in the patient's plasma over time (release profile) may extend over a period of at least 6 hours, preferably over at least 8 hours, and more preferably over about 12 hours. The compositions may provide in single dose a mean maximum plasma concentration of aminopyridine in the patient of from about 15 to about 180 ng/ml; a mean $T_{max}$ from about 1 to about 6 hours, more preferably about 2 to about 5.2 hours after administration of the composition to the patient.

In one embodiment, aminopyridine is administered to a subject at a dose and for a period sufficient to allow said subject to tolerate said dose without showing any adverse effects and thereafter increasing the dose at selected intervals of time until a therapeutic dose is achieved. In one embodiment, the medicament is administered to a subject at a dose and for a period sufficient to allow said subject to tolerate said dose without showing any adverse effects and thereafter increasing the dose of aminopyridine at selected intervals of time until a therapeutic dose is achieved. For example, at the commencement of treatment aminopyridine is preferably administered at a dose less than 15 mg/day until a tolerable state is reached. Suitably when said tolerable state is reached, the dose administered may be increased by amounts of at least 5-15 mg/day until said therapeutic dose is reached.

Preferably, aminopyridine is administered at a dose of about 10-15 mg twice daily (20-30 mg/day) depending upon the condition or symptoms being treated. The method can include scheduling administration of doses of the pharmaceutical so that the concentration of the aminopyridine in the patient is at about the minimum therapeutically effective level to ameliorate the neurological condition, yet relatively lower compared to the maximum concentration in order to enhance restful periods for the patient during the day or night, depending on desired results or dosage schedule. Preferably the method provides for the treatment of neurological diseases characterized by a degradation of nerve impulse transmission comprising the step of administering to a patient a composition of the present invention.

The formulations and compositions of the present invention exhibit a specific, desired release profile that maximizes the therapeutic effect while minimizing adverse side effects. The desired release profile may be described in terms of the maximum plasma concentration of the drug or active agent ($C_{max}$) and the plasma concentration of the drug or active agent at a specific dosing interval ($C\tau$). A ratio of $C_{max}$ to $C_\tau$ ($C_{max}:C_\tau$) may be calculated from the observed $C_{max}$ and $C_\tau$. A dosing interval ($\tau$) is the time since the last administration of the drug or active agent. In the present application, the dosing interval ($\tau$) is twelve (12) hours, therefore $C_\tau$ is the concentration of the drug or active agent at twelve (12) hours from the last administration.

Additionally, the formulations and compositions of the present invention exhibit a desired release profile that may be described in terms of the maximum plasma concentration of the drug or active agent at steady state ($C_{maxSS}$) and the minimum plasma concentration of the drug or active agent at steady state ($C_{minSS}$). Steady state is observed when the rate of administration (absorption) is equal to the rate of elimination of the drug or active agent. A ratio of $C_{maxSS}$ to $C_{minSS}$ ($C_{maxSS}:C_{minSS}$) may be calculated from the observed $C_{maxSS}$ and $C_{minSS}$. In addition, the formulations and compositions of the present invention exhibit a desired release profile that may be described in terms of the average maximum plasma concentration of the drug or active agent at steady state ($C_{avSS}$).

Another embodiment is a sustained release tablet of a sustained release matrix and an aminopyridine, said tablet exhibits a release profile to obtain a $C_{max}:C_\tau$ ratio in vivo of 1.0 to 3.5, and more preferably a $C_{max}:C_\tau$ ratio of about 1.5 to about 3.0. In another preferred embodiment, the $C_{max}:C_\tau$ ratio is about 2.0 to about 3.0. The aminopyridine may comprise 4-aminopyridine. The sustained release matrix may include for example, hydroxypropylmethylcellulose, or other rate controlling matrices that are suitable for controlling the release rate of an aminopyridine for use in the pharmaceutical compositions of the present invention.

Another embodiment is a sustained release tablet of a sustained release matrix and an aminopyridine, said tablet exhibits a release profile to obtain a $C_{max}:C_\tau$ ratio in vivo of 1.0 to 3.5 and a $C_{avSS}$ of about 15 ng/ml to about 35 ng/ml, and more preferably a $C_{max}:C_\tau$ ratio of about 1.5 to about 3.0. In another preferred embodiment, the $C_{max}:C_\tau$ ratio is about 2.0 to about 3.0.

A further aspect is a sustained release composition comprising a sustained release matrix and an aminopyridine, wherein said composition provides a $C_{avss}$ of about 15 ng/ml to about 35 ng/ml. In a further aspect, a sustained release tablet comprising a sustained release matrix and an aminopyridine, said tablet exhibiting a $C_{maxss}$ of about 20 ng/ml to about 35 ng/ml is provided. The pharmacokinetic characteristics of sustained release aminopyridine compositions and methods of treating various neurological disorders are described in co-pending PCT/US2004/008101 entitled "Stable Formulations of Aminopyridines and Uses Thereof" filed Apr. 17, 2004 and U.S. application Ser. No. 11/010,828 entitled "Sustained Release Aminopyridine Composition" filed Dec. 13, 2004, the contents of which are incorporated herein by reference in their entireties.

The amount of a pharmaceutically acceptable quality aminopyridine, salt, solvated, or prodrug thereof included in the pharmaceutical composition of the present invention will vary, depending upon a variety of factors, including, for example, the specific potassium channel blocker used, the desired dosage level, the type and amount of rate-controlling polymer matrix used, and the presence, types and amounts of additional materials included in the composition. Preferably, the aminopyridine comprises from about 0.1 to about 13% w/w, more preferably from about 0.5 to about 6.25% w/w. In an even more preferable embodiment of the present invention the aminopyridine is present from about 0.5 to 4.75% w/w of the pharmaceutical composition. Accordingly, a weight percentage less than about 4.75% is desired. The amount of aminopyridine, or a derivative thereof, in the formulation varies depending on the desired dose for efficient drug delivery, the molecular weight, and the activity of the compound. The actual amount of the used drug can depend on the patient's age, weight, sex, medical condition, disease or any other medical criteria. The actual drug amount is determined according to intended medical use by techniques known in the art. The pharmaceutical dosage formulated according to the invention may be administered once or more times per day, preferably two or fewer times per day as determined by the attending physician.

Suitable formulations and methods of manufacture are further described in co-pending PCT/US2004/008101 entitled "Stable Formulations of Aminopyridines and Uses Thereof" filed Apr. 17, 2004 and U.S. application Ser. No. 11/010,828 entitled "Sustained Release Aminopyridine Composition" filed Dec. 13, 2004, the contents of which are incorporated herein by reference in their entireties.

The release matrix aminopyridine formulation is preferably fabricated into tablets, capsules or granules for oral use. The rate of aminopyridine release from the tablets may be controlled by the erosion mechanism of the release matrix from which aminopyridine is released. In general, for producing a tablet on an industrial scale, the drug and polymer are granulated alone or in combination. Preferably the release of the aminopyridine from the matrix of the pharmaceutical composition is relatively linear over time. Preferably the matrix provides a release profile that gives a therapeutically effective concentration of the aminopyridine in the plasma of the patient permitting a once per day or twice per day dosing. Preferably the sustained release aminopyridine formulation for oral administration to patients includes from about 0.0001 mole to about 0.0013 mole aminopyridine that provides a mean maximum plasma concentration of aminopyridine from about 15 to about 180 ng/ml, a mean $T_{max}$ of about 2 to about 5 hours after administration, and a mean minimum plasma concentration of from about 10 to 60 ng/ml at about 8-24 hours after administration.

The formulations of the invention are prepared by procedures known in the art, such as, for example, by the dry or wet method. The method selected for manufacturing affects the release characteristics of the finished tablet. In one method, for example, the tablet is prepared by wet granulation in the presence of either water or an aqueous solution of the hydrophilic polymer or using other binder as a granulating fluid. In alternative, organic solvent, such as isopropyl alcohol, ethanol and the like, may be employed with or without water. The drug and polymer may be granulated alone or in combination. Another method for preparation of the tablet which may be used requires using a drug-polymer dispersion in organic solvents in the presence or absence of water. Where the aminopyridine or its derivative has very low solubility in water it may be advantageous to reduce the particle size, for example, by milling it into fine powder and in this way to control the release kinetics of the drug and enhance its solubility.

The hardness of the tablets of the present invention may vary, depending on a variety of factors, including, for example, the relative amounts and specific types of ingredients used, the tableting equipment employed, and the selected processing parameters. The pressure used to prepare the tablets can influence the release profile of the aminopyridine into the patient. The pressure used to prepare the tablets of the present invention may vary depending upon their surface area and the amount and particle size of aminopyridine, additive, excipients, or binders included in the tablet. The degree of hydration and solvation of the components in the composition will also be important in determining the hardness of the tablets. Preferably the formed tablets have a hardness in the range of from 80-400 N, and more preferably from 150 to 300 N.

The effects of various matrices, concentrations of aminopyridine, as well as various excipients and additives to the composition on the concentration of the channel blocker on the dissolution rate may be monitored for example using a type H dissolution apparatus according to U.S. Pharmacopoeia XXII, or USP Apparatus II (Paddle Method). Clinical evaluations may be used to study the effects on plasma levels of various release matrices, concentrations of aminopyridine, as well as various excipients and additives. Plasma aminopyridine concentrations may be used to calculate pharmacokinetic data (release profiles) including apparent absorption and elimination rates, area-under-the curve (AUC), maximum plasma concentration ($C_{max}$), time to maximum plasma concentration ($T_{max}$), absorption half-life ($T_{1/2}(abs)$), and elimination half-life ($T_{1/2}(elim)$). Pharmacodynamic effects may be assessed based upon response tests, such as muscle strength improvement or reduction in spasticity for patients with multiple sclerosis or spinal cord injury or other tests as would be known to those skilled in the art. Plasma aminopyridine concentration in blood plasma or cerebral spinal fluid may be monitored using liquid chromatography/MS/MS assay methods.

The drug delivery of the invention can utilize any suitable dosage unit form. Specific examples of the delivery system of the invention are tablets, tablets that disintegrate into granules, capsules, sustained release microcapsules, spheroids, or any other means that allow for oral administration. These forms may optionally be coated with pharmaceutically acceptable coating which allows the tablet or capsule to disintegrates in various portions of the digestive system. For example a tablet may have an enteric coating that prevents it from dissolving until it reaches the more basic environment of the small intestine.

The dispersion of the aminopyridine throughout the release matrix imparts enhanced stability characteristics in the dosage formulation. This enhanced stability is achieved without loss of the desired sustained-release profile. Preferably the release profile, which may be measured by dissolution rate is linear or approximately linear, preferably the release profile is measured by the concentration of the aminopyridine in the plasma in the patient and is such to permit twice daily (BID) dosing.

The pharmaceutical composition of the present invention can include also auxiliary agents or excipients, for example, glidants, dissolution agents, surfactants, diluents, binders including low temperature melting binders, disintegrants, solubilizing agents and/or lubricants as described in co-pending PCT/US2004/008101 entitled "Stable Formulations of Aminopyridines and Uses Thereof" filed Apr. 17, 2004 and U.S. application Ser. No. 11/010,828 entitled "Sustained Release Aminopyridine Composition" filed Dec. 13, 2004, the contents of which are incorporated herein by reference in their entireties.

The active ingredient of the present invention may be mixed with excipients which are pharmaceutically acceptable and compatible with the active ingredient and in amounts suitable for use in the therapeutic methods described herein. Various excipients may be homogeneously mixed with the aminopyridines of the present invention as would be known to those skilled in the art. For example, aminopyridines may be mixed or combined with excipients such as but not limited to microcrystalline cellulose, colloidal silicon dioxide, lactose, starch, sorbitol, cyclodextrin and combinations of these.

To further improve the stability of the aminopyridine in the sustained release composition, an antioxidant compound can be included. Suitable antioxidants include, for example: sodium metabisulfite; tocopherols such as $\alpha,\beta,\delta$-tocopherol esters and $\alpha$.-tocopherol acetate; ascorbic acid or a pharmaceutically acceptable salt thereof; ascorbyl palmitate; alkyl gallates such as propyl gallate, Tenox PG, Tenox s-1; sulfites or a pharmaceutically acceptable salt thereof; BHA; BHT; and monothioglycerol.

In another embodiment, the pharmaceutical composition of the present invention comprises a rate-controlling polymeric matrix comprising of a hydrogel matrix. For instance, an aminopyridine may be compressed into a dosage formulation containing a rate-controlling polymer, such as HPMC, or mixture of polymers which, when wet, will swell to form a hydrogel. The rate of release of the aminopyridine from this dosage formulation is sustained both by diffusion from the swollen tablet mass and by erosion of the tablet surface over time. The rate of release of the aminopyridine may be sustained both by the amount of polymer per tablet and by the inherent viscosities of the polymers used.

According to another aspect of the invention, there is provided a stable, sustained-release oral dosage formulation which includes an effective amount a aminopyridine dispersed in a release matrix, and which, upon administration to a patient or as part of a therapy regiment, provides a release profile (of therapeutically effective blood plasma level of the aminopyridine) extending for a period of at least 6 hours, preferably at least 12 hours. In another embodiment, the stable, controlled-release oral dosage form provides, upon administration to a patient, a therapeutically effective blood plasma level of the aminopyridine for a period of at least 6 hours, preferably at least 12 hours, and more preferably at least 24 hours.

The dosage formulation may assume any form capable of delivering orally to a patient a therapeutically effective amount of an aminopyridine dispersed in a rate-controlling polymer. Preferably, the dosage formulation comprises a monolithic tablet.

Tablet weight will also vary in accordance with, among other things, the aminopyridine dosage, the type and amount of rate-controlling polymer used, and the presence, types and amounts of additional materials. Assuming 4-aminopyridine dosages of from about 2 mg to about 120 mg; tablet weights can range from about 50 mg to about 1200 mg per tablet, and preferably from 250 to 500 mg, and more preferably about 400 mg.

The dosage formulation of the present invention may comprise also one or more pharmaceutically acceptable excipients as mentioned above. In preferred embodiments, the dosage formulation will comprise diluents and a lubricant in addition to the aminopyridine unit dose and the rate-controlling polymer. Particularly preferred diluents is microcrystalline cellulose sold under the name Avicel PH101, and a particularly preferred lubricant is magnesium stearate. When these materials are used, the magnesium stearate component preferably comprises from about 0.2 to about 0.75% w/w of the dosage formulation, and the microcrystalline cellulose along with the rate controlling polymer and aminopyridine comprises the balance of the formulation. For example, a tablet formulation including a aminopyridine x % w/w, a rate-controlling polymer y % w/w, and microcrystalline cellulose z %, the magnesium stearate amount would be (100−(x+y+z)) where 0.2%≤(100−(x+y+z))≤0.75% w/w. As would be known to those skilled in the art, the amount of an additives such as magnesium stearate may vary depending upon the shear rate used to perform the mixing and the amount of such an additive may be changed without limitation to obtain a satisfactory dissolution rate or plasma level of the aminopyridine.

As used herein, the term "sustained-release" as it relates to the aminopyridine compositions includes the release of a aminopyridine from the dosage formulation at a sustained rate such that a therapeutically beneficial blood level below toxic levels of the aminopyridine is maintained over a period of at least about 12 hours, preferably about 24 hours or more. Preferably, the amount of the aminopyridine in the oral dosage formulations according to embodiments of the present invention establish a therapeutically useful plasma concentration through BID administration of the pharmaceutical composition.

If desired, the dosage formulations of this invention may be coated with a sustained-release polymer layer so as to provide additional sustained-release properties. Suitable polymers that can be used to form this sustained release layer include, for example, the release matrices listed above. As desired, the dosage formulation of the invention can be provided also with a light-protective and/or cosmetic film coating, for example, film-formers, pigments, anti-adhesive agents and politicizes. Such a film-former may consist of fast-dissolving constituents, such as low-viscosity hydroxypropylmethylcelluose, for example, Methocel E5 or D14, or Pharmacoat 606 (Shin-Etsu). The film coating may also contain excipients or enteric coatings customary in film-coating procedures, such as, for example, light-protective pigments, for example, iron oxide, or titanium dioxide, anti-adhesive agents, for example, talc, and also suitable plasticizers such as, for example, PEG 400, PEG 6000, diethyl phthalate or triethyl citrate.

The compositions of the present invention may be used for the treatment of neurological diseases characterized by a degradation of nerve impulse transmission by administering to a patient the oral dosage formulation of the present invention. Preferably, the administration is twice daily dosage of a therapeutically effective amount of an aminopyridine, even more preferably, 4-AP dispersed in HPMC. The administration can also include scheduling administration of doses of the pharmaceutical so that the concentration of the aminopyridine in the patient is at about the minimum therapeutically effective level to ameliorate the neurological condition, yet relatively low compared to the maximum concentration in order to minimize side effects. The compositions may be administered to a subject at a dose and for a period sufficient to allow said subject to tolerate said dose without showing any adverse effects and thereafter increasing the dose of said active agent in the tablets at selected intervals of time until a therapeutic dose is achieved in the subject. For example, at the commencement of treatment the active agent is preferably administered at a dose less than about 15 mg/day until a tolerable state is reached. The dose administered may then be increased by amounts of at least 5-10 mg/day until a therapeutic dose is reached, preferably less than about 30 mg/day. For other diseases the amount of the aminopyridine required to reach a therapeutically effective amount for treatment is described in U.S. Pat. No. 5,952,357 the contents of which are incorporated herein by reference in their entirety.

Compositions of the present invention where the potassium channel blocker is a mono- or di-aminopyridine active agent are particularly suitable for use in the treatment of a neurological disease that is characterized by demyelination of the central nervous system, more especially multiple sclerosis.

In one embodiment of the present invention, a method of treating multiple sclerosis is provided. Compositions of the present invention containing a therapeutically effective amount of mono- or di-aminopyridine active agent may be administered to a patient in need thereof. In particular, sustained release compositions comprising at least about 5 milligrams of an aminopyridine, preferably 4-aminopyridine may be administered at least once daily. In a preferred embodiment, a sustained release composition containing from about 10 to about 15 milligrams of 4-aminopyridine is administered twice daily. Treatment of multiple sclerosis may include increased walking speed, improved lower extremity muscle strength or improved lower extremity muscle tone. The sustained release aminopyridine composition is preferably administered twice daily. In certain embodiments, the composition may be administered about every 12 hours.

A further embodiment is a method of increasing walking speed in patients with multiple sclerosis comprising administering to a patient at least about 5 milligrams of a sustained release aminopyridine composition, preferably at least about 10 to about 15 milligrams of a sustained release aminopyridine composition.

A further embodiment is a method of increasing muscle tone or muscle strength in patients with multiple sclerosis comprising administering to a patient at least about 5 milligrams of a sustained release aminopyridine composition, preferably at least about 10 to about 15 milligrams of a sustained release aminopyridine composition.

Fampridine is a potential therapy for MS with a unique mechanism of action. At concentrations of 1-2 μM or less, fampridine appears to be a specific blocker of voltage dependent, neuronal potassium channels that affect conduction in demyelinated axons. Fampridine has been shown to restore action potential conduction in damaged, poorly myelinated nerve fibers, and it may also directly enhance synaptic transmission. In previous clinical trials, treatment with fampridine has been associated with a variety of neurological benefits in people with MS including faster walking and increased strength, as measured by standard neurological assessments.

Another aspect of the present invention provides for a method of selecting individuals based on responsiveness to a treatment. In one embodiment, the method comprises identifying a plurality of individuals; administering a test to each individual prior to a treatment period; administering a treatment, including, but not limited to administering a therapeutic agent or drug, to one or more of the individuals during the treatment period; administering the test a plurality of times to each individual during the treatment period; and selecting one or more individuals, wherein the selected individuals exhibit an improved performance during a majority of the tests administered during the treatment period as compared to the test administered prior to the treatment period. In certain embodiments, the method may further comprise administering the test to each individual after the treatment period, wherein the selected individuals further exhibit an improved performance during a majority of the tests administered during the treatment period as compared to the test administered after the treatment period.

It is important to note that this embodiment selects subjects who show a pattern of change that is consistent with a treatment response, but does not define the full characteristics of that response. The criterion itself does not specify the amount of improvement nor does it specify that the improvement must be stable over time. For example, a progressive decline in effect during the course of the study period, even one resulting in speeds slower than the maximum non-treatment value, would not be excluded by the criterion; as a specific example, changes from the maximum non-treatment value of, respectively, +20%, +5%, +1% and −30% during the double blind treatment period would qualify as a response under the criterion, but would actually show a net negative average change for the entire period, poor stability and a negative endpoint. Post-hoc analyses of studies discussed in greater detail below indicate that we may expect responders defined by consistency of effect also to demonstrate increased magnitude and stability of benefit.

We have found this embodiment particularly applicable in our analysis of fampridine in patients suffering from multiple sclerosis. Clinicians who regularly prescribe compounded fampridine for MS have reported that only a proportion of their patients appear to respond with clear clinical benefits, and that, in their judgment, this proportion may be around one third. This extent of responsiveness may be related to the proposed mechanism of action, which is the restoration of conduction in demyelinated axons via the blockade of voltage-dependent potassium channels. Only a proportion of MS patients would be expected to possess axons of appropriate functional relevance that are susceptible to these drug effects, given the highly variable pathology of the disease. Currently, there is insufficient understanding of the disease to allow for pre-trial selection of potentially responsive patients. However, the existence of a subset of patients who respond consistently to the drug can be supported by quantitative observations in our own clinical studies discussed below.

Before treatment, the subjects in these two trials exhibited average walking speeds on the TW25 measure of approximately 2 feet per second (ft/sec). This is a significant deficit, since the expected walking speed for an unaffected individual is 5-6 ft/sec. Subjects in MS-F202 were selected for TW-25 walking time at screening of 8-60, which is equivalent to a range in speed of 0.42-3.1 ft/sec. Variability of functional status is an inherent characteristic of MS, and this can be seen in repeated measurement of walking speed over the course of weeks or months. At any of the three visits during the stable treatment period, 15-20% of placebo-treated subjects showed >20% improvement from baseline walking speed, a threshold chosen as one that indicates a true change in walking speed over background fluctuations. A larger proportion of the Fampridine-SR treated subjects showed such improvements, but this difference was not statistically significant, given the sample size and placebo response rate.

Given the often large variations in function experienced by people with MS, it is difficult for the subject or a trained observer to separate a treatment-related improvement from a disease-related improvement without the element of consistency over time. Consistency of benefit might therefore be expected to be a more selective measure of true treatment effect than magnitude of change. Based on this rationale, the responses of the individual subjects in the MS-F202 trial were examined for the degree to which their walking speed showed improvement during the double-blind treatment period and returned towards pre-treatment values after they were taken off drug, at follow-up. This subject-by-subject examination yielded a subgroup of subjects whose pattern of walking speed over time appeared to be consistent with a drug response. This led to the analysis illustrated in FIG. 1. This compares the placebo and Fampridine-SR treated groups with respect to the number of visits during the double-blind treatment period in which walking speed on the TW25 was faster than the maximum speed out of all five of the non-treatment visits (four visits prior to randomization and one follow-up visit after the drug treatment period).

The placebo-treated group showed a clear pattern of exponential decline in numbers of subjects with higher numbers of "positive" visits. This is what would be expected from a random process of variability. In contrast, the pattern of response in the Fampridine-SR treated group strongly diverged from this distribution; much larger numbers of Fampridine-SR treated subjects showed three or four visits with higher walking speeds than the maximum speed of all five non-treatment visits and less than half of the expected proportion had no visits with higher speeds. These results indicate that there was a sub-population of subjects in the Fampridine-SR treated group that experienced a consistent increase in walking speed related to treatment.

This analysis suggests that a relatively highly selective criterion for a likely treatment responder would be: a subject with a faster walking speed for at least three (i.e., three or four) of the four visits during the double blind treatment period compared to the maximum value for all five of the non-treatment visits. The four visits before initiation of double-blind treatment provide an initial baseline against which to measure the consistency of response during the four treatment visits. The inclusion of the follow-up visit as an additional component of the comparison was found valuable primarily in excluding those subjects who did not show the expected loss of improvement after coming off the drug. These are likely to be subjects who happened by chance to have improved in their MS symptoms around the time of treatment initiation, but whose improvement did not reverse on drug discontinuation because it was actually unrelated to drug. Thus, incorporating the follow-up visit as part of the criterion may help to exclude false positives, if the TW25 speed remains high at follow-up.

As described in Example 5, below, this responder criterion was met by 8.5%, 35.3%, 36.0%, and 38.6% of the subjects in the placebo, 10 mg, 15 mg, and 20 mg b.i.d. treatment groups, respectively, showing a highly significant and consistent difference between placebo and drug treatment groups. Given that there was little difference in responsiveness between the three doses examined, more detailed analyses were performed comparing the pooled Fampridine-SR treated groups against the placebo-treated group. The full results of this analysis for study are described in the following sections. These show that the responder group so identified experienced a >25% average increase in walking speed over the treatment period and that this increase did not diminish across the treatment period. The responder group also showed an increase in Subject Global Impression score and an improvement in score on the MSWS-12.

Additional features and embodiments of the present invention are illustrated by the following non-limiting examples.

EXAMPLE 1

This example illustrates preparation of compositions of the present invention and their release of an aminopyridine. Tablets in accordance with the present invention having dosages of 5 mg, 7.5 mg and 12.5 mg respectively were manufactured at 5 Kg scale. Materials were used in the amounts shown in Table 1.

TABLE 1

|  | % w/w | % w/w | % w/w |
|---|---|---|---|
| Milled 4-AP (#50 mesh) | 1.25 | 1.875 | 3.125 |
| Methocel K100LV | 60 | 60 | 60 |
| Avicel PH101 | 38.15 | 37.525 | 36.275 |
| Magnesium stearate | 0.2 | 0.2 | 0.2 |
| Aerosil 200 | 0.4 | 0.4 | 0.4 |
| Equipment Tablet Press | Horn Noak equipped with 13 × 8 mm oval tooling press speed 42,000 tablets/hr | | |
| Tablet Weight Range (mg) | 386-404 (96.5-101.0%) | 388-410 (97.0-102.5%) | 388-406 (97.0-101.5%) |
| Tablet Hardness Range (N) | 200-262 | 179-292 | 150-268 |
| Tablet Potency - mg/tab. (% LC) | 97.1 | 99.1 | 100.2 |
| Mean CU (mg/tab.)/ % CV | 5.0 mg/1.0% | 7.4 mg/0.7% | 12.4 mg/1.1% |
| CU Discrete Samples (mg/tab.)/% CV | 5.0 mg/1.2% | 7.5 mg/1.8% | 12.3/1.1% |

| Dissolution (%/hr) | Mean | (SD) | Mean | (SD) | Mean | (SD) |
|---|---|---|---|---|---|---|
| 1 | 28.9 | 1.1 | 29.2 | 1.8 | 25.9 | 1.1 |
| 2 | 42.7 | 1.8 | 42.1 | 1.6 | 40.2 | 2.5 |
| 3 | 52.8 | 1.4 | 53.0 | 1.0 | 49.8 | 2.1 |
| 4 | 61.4 | 2.2 | 61.8 | 1.5 | 60.1 | 2.4 |
| 6 | 75.7 | 3.1 | 75.2 | 1.6 | 74.8 | 2.7 |
| 10 | 95.5 | 3.3 | 98.7 | 1.4 | 93.2 | 0.9 |

Prior to blending, 4-AP was milled through #50 mesh screen using a Fitzmill® comminutor. The materials were added into a Gral 25 bowl in the following order: half Methocel K100LV, Avicel PH101, Aerosil 200, milled 4-AP and the remaining Methocel K100LV. The mix was blended for 15 minutes at 175 rpm, then the magnesium stearate was added and was further blended for 5 minutes at 100 rpm.

Samples were taken from top and bottom positions for blend potency analysis. Weight and hardness checks were performed every 15 minutes by the check-master E3049. Discrete tablet samples were taken during the compression process to evaluate intra batch content uniformity.

EXAMPLE 2

This example illustrates that the pharmacokinetic profile of fampridine in compositions of the present invention is altered by administration in a sustained release tablet matrix compared to immediate release and controlled release formulations.

There is a delay in absorption manifested by a lower peak concentration, without any effect on the extent of absorption. When given as a single 12.5 mg dose, the peak concentration is approximately two-thirds lower as compared to peak values following administration of the IR formulation; the time to reach peak plasma levels was delayed by about 2 hours. As with the IR formulation, food delayed the absorption of Fampridine-SR. The absorption of fampridine was approximately 50% slower following ingestion of a fatty meal, although due to the flatness of the absorption curve, this may be exaggerated value. Extent of absorption did not differ, as values for Cmax and AUC were comparable as summarized in Table 2.

malized to a 10 mg dose for among-dose comparisons. Overall observed time of the peak plasma concentration (mean and its 95% confidence interval) was 3.75 (3.52, 3.98) h, observed peak plasma fampridine concentration (normalized to a 10 mg dose) was 24.12 (23.8, 26.6) ng/ml, area-under-the-concentration-time curve (normalized to a 10 mg dose) was estimated to be 254 (238, 270) ng·h/ml, extrapolated area-under-the-concentration-time curve (normalized to a 10 mg dose) was 284 (266, 302) ng·h/ml, terminal rate constant equaled 0.14 (0.13, 0.15) $h^{-1}$, terminal half-life was 5.47 (5.05, 5.89) h and clearance divided by bioavailability (CL/F) was equal to 637 (600, 674) ml/min.

Dizziness was the most common treatment-related adverse event. Other treatment related adverse events included amblyopia, asthenia, headache, and ataxia. There were no clinically significant changes in clinical laboratory values, ECG parameters, vital signs, physical examination findings, or neurological examination findings noted over the course of this study.

When the plasma concentrations of fampridine were normalized to the 10.0 mg dose levels, there were no significant differences between any pharmacokinetic parameter (AUC, $C_{max}$, $t_{1/2}$) in the 5-20 mg dose range. Fampridine was well tolerated at the doses used in this study. Dose-normalized (to a 10 mg dose) pharmacokinetic parameter values are summarized in Table 3.

TABLE 2

Pharmacokinetic Parameter Values (Mean ± SD) in Studies Using Fampridine SR, CR, and IR Formulations: Single Dose Studies in Healthy Adult Male Volunteers

| Study Number | Dose (mg) | Fed/Fasted | $C_{MAX}$ (ng/mL) | $t_{MAX}$ (hours) | AUC (0-∞) (ng hr/mL) |
|---|---|---|---|---|---|
| 0494006 N = 12 | 12.5 SR (PD12265) | Fed | 28.7 ± 4.3 | 5.3 ± 0.8 | 257.0 ± 62.7 |
|  |  | Fasted | 25.6 ± 3.8 | 2.8 ± 1.3 | 269.9 ± 44.4 |
|  | 12.5 IR (PD12266) | Fasted | 79.3 ± 16.3 | 0.9 ± 0.4 | 294.2 ± 55.6 |
| 1194002 N = 12 | 12.5 SR (PD12907) | Fasted | 28.5 ± 4.3 | 2.9 ± 2.4 | 285.9 ± 37.8 |
|  | 12.5 CR (4n806) | Fasted | 37.7 ± 9.9 | 3.6 ± 0.9 | 300.0 ± 53.6 |
|  | 12.5 IR (PS644) | Fasted | 83.5 ± 23.5 | 0.79 ± 0.3 | 274.0 ± 59.2 |

EXAMPLE 3

This example details the pharmacokinetic properties of Fampridine-SR in tablets of the present invention administered to patients with multiple sclerosis. Plasma samples were analyzed for fampridine using a validated LC/MS/MS assay with a sensitivity of 2 ng/mL. Noncompartmental pharmacokinetic parameter values were calculated using standard methodology.

This was an open-label, multi-center, dose proportionality study of orally administered fampridine in patients with multiple sclerosis. Single doses of fampridine were to be given in escalating doses (5 mg, 10 mg, 15 mg, and 20 mg) with at least a four-day interval between administration of each dose of drug. Safety evaluations were to be performed during the 24 hour period following administration of fampridine and blood samples were to be taken at the following times to determine pharmacokinetic parameters; hour 0 (pre-dose), hours 1-8, and hours 10, 12, 14, 18, and 24.

Twenty-three subjects received all 4 treatments, and one subject received only 3 treatments; data from all treatments were analyzed. Dose-dependent parameters (e.g., peak plasma concentration and areas-under-the-curve) were nor-

TABLE 3

Dose-Normalized (at 10 mg) Pharmacokinetic Parameter Values (Mean ± SEM) Following Single Oral Administration of Fampridine-SR to Patients with MS.

| Dose (mg) | $C_{MAX}$ norm (ng/mL) | $t_{MAX}$ (hours) | AUC-norm (ng hr/mL) | $t_{1/2}$ (hours) | Cl/F (mL/min) |
|---|---|---|---|---|---|
| 5 (n = 24) | 26.2 ± 0.6 | 3.9 ± 0.2 | 244.2 ± 9.4 | 5.8 ± 0.5 | 619.8 ± 36.2 |
| 10 (n = 24) | 25.2 ± 0.7 | 3.9 ± 0.3 | 252.2 ± 7.8 | 5.6 ± 0.4 | 641.4 ± 39.1 |
| 15 (n = 24) | 24.6 ± 0.7 | 3.6 ± 0.3 | 263.0 ± 7.4 | 5.5 ± 0.4 | 632.4 ± 39.0 |
| 20 (n = 23) | 24.6 ± 0.8 | 3.6 ± 0.3 | 255.6 ± 6.9 | 5.1 ± 0.3 | 653.9 ± 37.1 |

EXAMPLE 4

This example describes the results of an open-label study to assess the steady state pharmacokinetics of orally administered fampridine (4-aminopyridine) compositions of the present invention in subjects with Multiple Sclerosis. This study was an open-label multiple dose study of Fampridine-SR intended to assess steady state pharmacokinetics in 20 patients with MS who previously completed the study summarized in Table 4. Fampridine-SR (40 mg/day) was administered as two 20 mg doses, given as one morning and one evening dose for 13 consecutive days, with a single administration of 20 mg on Day 14. Blood samples for pharmacokinetic analysis were collected on Days 1, 7/8, and 14/15 at the following intervals: immediately prior to drug administration (baseline), hourly for the first 8 hours, and 10, 12, and 24 hours post-dose. Additional blood samples were collected 14, 18, and 20 hours post-dose on Day 14, and 30 and 36 hours post-dose on Day 15.

Pharmacokinetic parameter estimates following the first dose in these patients in this study on Day 1 were comparable to those determined when they participated in the study summarized in Table 4. No significant difference in $T_{max}$ was detected among the four means (Single dose=3.76 h; Day 1=3.78 h; Day 8=3.33 h; Day 15=3.25 h). $C_{max}$ and $C_{max}/C_\tau$ on Days 8 ($C_{max}$=66.7 ng/ml) and 15 ($C_{max}$=62.6 ng/ml) were significantly greater than those of the single dose treatment and of Day 1 ($C_{max}$=48.6 ng/ml), reflecting accumulation of the drug with multiple dosing.

There was no significant difference among the four occasions with regard to either T or C and no difference in $C_{max}$, $C_{max}/C_\tau$, CL/F or $AUC_{0-\tau}$ between Days 8 and 15. Further AUC on Days 8 and 15 did not differ significantly from total AUC with single dose treatment. Likewise, the estimates of CL/F on Days 8 and 15 and of λ and $T_{1/2}$ on Day 15 did not differ significantly from those with single dose.

Steady-state was attained by Day 7/8 as evidence by the lack of differences in $C_{max}$ or AUC between Days 7/8 and 14/15; there was no apparent unexpected accumulation. Likewise, the estimates of Cl/F on Days 7/8 and 14/15 of and of $T_{1/2}$ on Day 14/15 did not differ significantly from those given a single dose. On the final day of dosing, mean $C_{max}$ was 62.6 ng/mL, occurring 3.3 hours post-dose. The $T_{1/2}$ was 5.8 hours. These values are similar to those observed in patients with chronic SCI receiving similar doses of this formulation. These results are summarized in Table 4.

TABLE 4

Pharmacokinetic Parameter Values (Mean and 95% CI) Following Multiple Oral Doses of Fampridine-SR (40 mg/day) to 20 Patients with MS.

| Day | $C_{MAX}$ (ng/mL) | $t_{MAX}$ (hours) | $AUC_{(0-12)}$ (ng hr/mL) | $t_{1/2}$ (hours) | Cl/F (mL/min) |
|---|---|---|---|---|---|
| Day 1 | 48.6 (42.0, 55.3) | 3.8 (3.2, 4.3) | NE | NE | NE |
| Day 7/8 | 66.7 (57.5, 76.0) | 3.3 (2.8, 3.9) | 531 (452, 610) | NE | 700 (557, 884) |
| Day 14/15 | 62.6 (55.7, 69.4) | 3.3 (2.6, 3.9) | 499 (446, 552) | 5.8 (5.0, 6.6) | 703 (621, 786) |

Dizziness was the most common treatment-related adverse event. Other treatment-related adverse events that occurred included nausea, ataxia, insomnia, and tremor. There were no clinically significant changes in mean clinical laboratory values, vital signs, or physical examination findings from baseline to last visit. There were no apparent clinically significant changes in corrected QT intervals or QRS amplitudes after administration of fampridine.

Fampridine was well tolerated in subjects with multiple sclerosis who receive twice daily doses (20 mg/dose) of fampridine for two weeks. A significant increase was observed in $C_{max}$ and $C_{max}/C_\tau$ on Days 8 and 15 relative to those on Day 1 and with single dose treatment, reflecting accumulation of fampridine with multiple dosing. A lack of significant differences in $C_{max}$, $C_{max}/C_\tau$, CL/F or $AUC_{0-\tau}$ between Days 8 and 15 suggest that near steady-state is reached by Day 8. There was no evidence of significant changes in pharmacokinetics during a two-week period of multiple dosing with fampridine.

EXAMPLE 5

This example provides an embodiment of a method of treating subjects with a sustained release fampridine formulation and a responder analysis of the present invention. This was a Phase 2, double-blind, placebo-controlled, parallel group, 20-week treatment study in 206 subjects diagnosed with Multiple Sclerosis. This study was designed to investigate the safety and efficacy of three dose levels of Fampridine-SR, 10 mg b.i.d., 15 mg b.i.d., and 20 mg b.i.d. in subjects with clinically definite MS. The primary efficacy endpoint was an increase, relative to baseline, in walking speed, on the Timed 25 Foot Walk. Secondary efficacy measurements included lower extremity manual muscle testing in four groups of lower extremity muscles (hip flexors, knee flexors, knee extensors, and ankle dorsiflexors); the 9-Hole Peg Test and Paced Auditory Serial Addition Test (PASAT 3"); the Ashworth score for spasticity; Spasm Frequency/Severity scores; as well as a Clinician's (CGI) and Subject's (SGI) Global Impressions, a Subject's Global Impression (SGI), the Multiple Sclerosis Quality of Life Inventory (MSQLI) and the 12-Item MS Walking Scale (MSWS-12).

At the first visit (Visit 0) subjects were to enter into a two-week single-blind placebo run-in period for the purpose of establishing baseline levels of function. At Visit 2 subjects were to be randomized to one of four treatment groups (Placebo or Fampridine-SR 10 mg, 15 mg, 20 mg) and begin two weeks of double-blind dose-escalation in the active drug treatment groups (B, C and D). Group A were to receive placebo throughout the study. Subjects in the 10 mg (Group B) arm of the study took a dose of 10 mg approximately every 12 hours during both weeks of the escalation phase. The 15 mg (Group C) and 20 mg (Group D) dose subjects took a dose of 10 mg approximately every 12 hours during the first week of the escalation phase and titrated up to 15 mg b.i.d. in the second week. Subjects were to be instructed to adhere to an "every 12 hour" dosing schedule. Each subject was advised to take the medication at approximately the same time each day throughout the study; however, different subjects were on differing medication schedules (e.g., 7 AM and 7 PM; or 9 AM and 9 PM). After two weeks, the subjects were to return to the clinic at Visit 3 for the start of the stable dose treatment period. The first dose of the double-blind treatment phase at the final target dose (placebo b.i.d. for the Group A, 10 mg b.i.d. for Group B, 15 mg b.i.d. for Group C, and 20 mg b.i.d. for Group D) was taken in the evening following Study Visit 4. Subjects were to be assessed five times during the 12-week treatment period. Following the 12-week treatment phase there was to be a one-week down titration starting at Visit 9. During this down-titration period, group B was to remain stable at 10 mg b.i.d. and Group C was to be titrated to 10 mg b.i.d., while group D was to have a change in the level of dose during the week (15 mg b.i.d. for the first three days and 10 mg b.i.d. for the last four days). At the end of the down titration period at Visit 10, subjects were to enter a two-week washout period where they did not receive any study medication. The last visit (Visit 11) was to be scheduled two weeks after the last dosing day (end of the downward titration). Plasma samples were collected at each study site visit other than Study Visit 0.

The primary measure of efficacy was improvement in average walking speed, relative to the baseline period (placebo run-in), using the Timed 25 Foot Walk from the Multiple Sclerosis Functional Composite Score (MSFC). This is a quantitative measure of lower extremity function. Subjects were instructed to use whatever ambulation aids they normally use and to walk as quickly as they could from one end to the other end of a clearly marked 25-foot course. Other efficacy measures included the LEMMT, to estimate muscle strength bilaterally in four groups of muscles: hip flexors, knee flexors, knee extensors, and ankle dorsiflexors. The test was performed at the Screening Visit and at Study Visits 1, 2, 4, 7, 8, 9 and 11. The strength of each muscle group was rated on the modified BMRC scale: 5=Normal muscle strength; 4.5=Voluntary movement against major resistance applied by the examiner, but not normal; 4=Voluntary movement against moderate resistance applied by the examiner; 3.5=Voluntary movement against mild resistance applied by the examiner; 3=Voluntary movement against gravity but not resistance; 2=Voluntary movement present but not able to overcome gravity; 1=Visible or palpable contraction of muscle but without limb movement; and 0=Absence of any voluntary contraction. Spasticity in each subject was assessed using the Ashworth Spasticity Score. The Ashworth Spasticity Exam was performed and recorded at the Screening Visit and at Study Visits 1, 2, 4, 7, 8, 9 and 11.

Protocol Specified Responder Analysis. To supplement the primary analysis, a categorical "responder" analysis was also conducted. Successful response was defined for each subject as improvement in walking speed (percent change from baseline) of at least 20%. Subjects who dropped out prior to the stable dose period were considered non-responders. The proportions of protocol specified responders were compared among treatment groups using the Cochran-Mantel-Haenszel test, controlling for center.

Post hoc analysis of this study suggested that a relatively highly selective criterion for a likely treatment responder would be a subject with a faster walking speed for at least three visits during the double blind treatment period as compared to the maximum value among a set of five non-treatment visits (four before treatment and one after discontinuation of treatment). The four visits before initiation of double-blind treatment provided an initial baseline against which to measure the consistency of response during the four double-blind treatment visits. The inclusion of the follow-up visit as an additional component of the comparison was useful primarily in excluding those subjects who may be false positives, i.e., did not show the expected loss of improvement after coming off the drug. Treatment differences in the proportion of theses post hoc responders were analyzed using the Cochran-Mantel-Haenszel (CMH) test, controlling for center.

To validate the clinical meaningfulness of the post hoc responder variable, (post hoc) responders were compared against the (post hoc) non-responders, on the subjective variables: (i) Change from baseline in MSWS-12 over the double-blind; (ii) SGI over the double-blind; and (iii) Change from baseline in the CGI over the double-blind; to determine if subjects with consistently improved walking speeds during the double-blind could perceive improvement relative to those subjects who did not have consistently improved walking speeds. For the subjective variables, differences between responder status classification (responder or non-responder) were compared using an ANOVA model with effects for responder status and center.

Results. A total of 206 subjects were randomized into the study: 47 were assigned to placebo, 52 to 10 mg bid Fampridine-SR (10 mg bid), 50 to 15 mg bid Fampridine-SR (15 mg bid), and 57 to 20 mg bid Fampridine-SR (20 mg bid). The disposition of subjects is presented in Table 5 below.

TABLE 5

Summary of subject disposition (all randomized population)

| | Treatment Group: N (%) | | | | |
| --- | --- | --- | --- | --- | --- |
| | Placebo | 10 mg bid | 15 mg bid | 20 mg bid | Total |
| Subjects Randomized | 47 | 52 | 50 | 57 | 206 |
| Took at Least One Dose (Included in Safety Analysis) | 47 (100%) | 52 (100%) | 50 (100%) | 57 (100%) | 206 (100%) |
| ITT Population | 47 (100%) | 51 (98.1%) | 50 (100%) | 57 (100%) | 205 (99.5%) |
| Discontinued Subjects | 2 (4.3%) | 2 (3.8%) | 1 (2.0%) | 6 (10.5%) | 11 (5.3%) |

Note:
Percentages are based on the number of randomized subjects.

All 206 randomized subjects took at least one dose of study medication and were included in the safety population. One subject (subject #010/07 10 mg bid group) was excluded from the ITT population (lost to follow-up after 8 days of placebo run-in). A total of 11 subjects discontinued from the study.

The population consisted of 63.6% females and 36.4% males. The majority of the subjects were Caucasian (92.2%), followed by Black (4.9%), Hispanic (1.5%), those classified as 'Other' (1.0%), and Asian/Pacific Islander (0.5%). The mean age, weight, and height of the subjects were 49.8 years (range: 28-69 years), 74.44 kilograms (range: 41.4-145.5 kilograms), and 168.84 centimeters (range: 137.2-200.7 centimeters), respectively. Most of the subjects (52.4%) had a diagnosis type of secondary progressive with about equal amounts of relapsing remitting (22.8%) and primary progressive (24.8%) subjects. The mean duration of disease was 12.00 years (range: 0.1-37.5 years) while the mean Expanded Disability Status Scale (EDSS) at screening was 5.77 units (range: 2.5-6.5 units). The treatment groups were comparable with respect to all baseline demographic and disease characteristic variables.

Results for the key efficacy variables at baseline for the ITT population are further summarized in Table 6 below.

TABLE 6

Summary of key efficacy variables at baseline (ITT population)

| Parameter | Treatment Group: Mean (SD) | | | | Treatment. p-value |
|---|---|---|---|---|---|
| | Placebo N = 47 | 10 mg bid N = 51 | 15 mg bid N = 50 | 20 mg bid N = 57 | |
| Walking Speed (ft/sec) | 1.87 (0.902) | 1.94 (0.874) | 1.99 (0.877) | 2.04 (0.811) | 0.752 |
| LEMMT | 4.05 (0.690) | 3.98 (0.661) | 4.00 (0.737) | 3.98 (0.634) | 0.964 |
| SGI | 4.38 (0.795) | 4.32 (0.999)* | 4.56 (1.110) | 4.25 (0.969) | 0.413 |
| MSWS-12 | 75.71 (16.566) | 76.31 (16.186) | 74.60 (17.671) | 76.83 (18.124) | 0.923 |

*One subject did not have a baseline value.

With respect to the 205 subjects in the ITT population, mean values for baseline walking speed, LEEMT, SGI, and MSWS-12 were approximately 2 feet per second, 4 units, 4.5 units, and 76 units, respectively. The treatment groups were comparable with respect to these variables as well as all the other efficacy variables at baseline.

Figure 2:
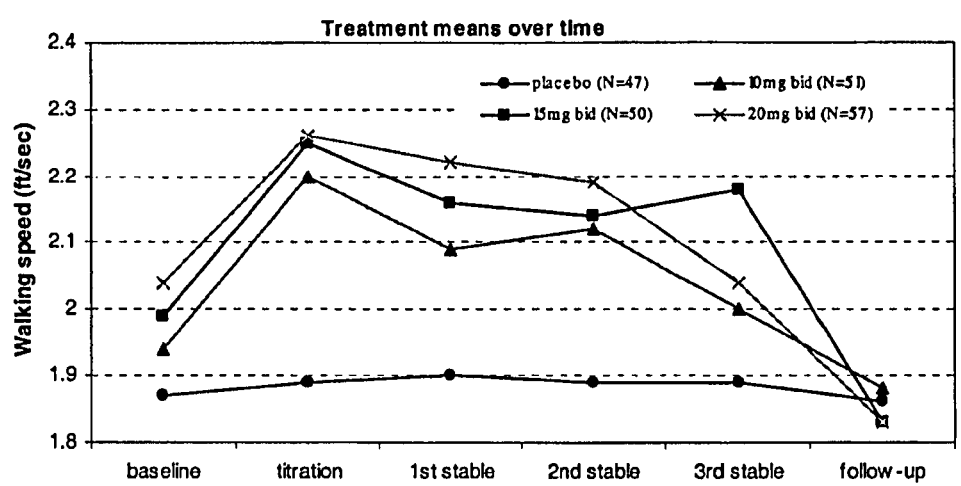
FIG. 2 is a graph of the average walking speeds (ft/sec) by study day (observed cases, ITT population).

Descriptive statistics for the average walking speed (ft/sec) by study day based on the Timed 25-Foot Walk are presented in Table 7 and FIG. 2. The timed 25 foot walk showed a trend toward increased speed during the stable dose period for all three dose groups, though the average improvement declined during the treatment period.

TABLE 7

Average walking speeds (ft/sec) by study day (observed cases, ITT population)
Summary Statistics Over Time

| Treatment | | Study day | | | | | |
|---|---|---|---|---|---|---|---|
| | | base | titration | 1st stbl | 2nd stbl | 3rd stbl | follow-up |
| placebo | Mean | 1.87 | 1.89 | 1.90 | 1.89 | 1.89 | 1.86 |
| | (SD) | (0.902) | (0.876) | (0.908) | (0.891) | (0.914) | (0.933) |
| | N# | 47 | 47 | 46 | 46 | 45 | 45 |
| 10 mg bid | Mean | 1.94 | 2.20 | 2.09 | 2.12 | 2.00 | 1.88 |
| | (SD) | (0.874) | (0.979) | (0.955) | (1.043) | (1.016) | (0.970) |
| | N | 51 | 51 | 51 | 51 | 50 | 48 |
| 15 mg bid | Mean | 1.99 | 2.25 | 2.16 | 2.14 | 2.18 | 1.83 |
| | (SD) | (0.877) | (0.995) | (0.986) | (0.957) | (0.932) | (0.952) |
| | N | 50 | 49 | 49 | 48 | 48 | 47 |
| 20 mg bid | Mean | 2.04 | 2.26 | 2.22 | 2.19 | 2.04 | 1.83 |
| | (SD) | (0.811) | (0.936) | (0.893) | (0.936) | (0.996) | (0.822) |
| | N | 57 | 55 | 52 | 51 | 49 | 55 |

The treatment sample sizes presented in the figure legend represent the number of ITT subjects. Sample sizes at individual time points may be smaller than those in the ITT population due to dropouts or missed assessments.

During double-blind treatment, all the Fampridine-SR groups exhibited mean walking speeds between 2.00 and 2.26 feet per second, while the mean value in the placebo group was consistently about 1.90 feet per second. It should be noted that, at the third stable-dose visit, both the 10 mg bid and 20 mg bid group means dropped-off from what would be expected under the assumption that treatment benefit is consistent over time. This may or may not have been due to chance; further studies should provide additional evidence for either case. After double-blind medication was discontinued, all the treatment groups converged to approximately the same mean value at follow-up.

Figure 3:
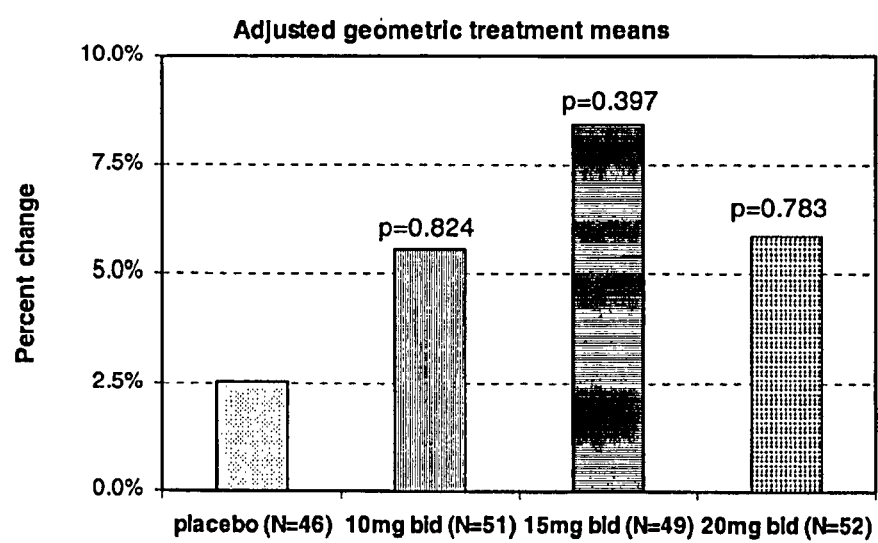
FIG. 3 is a histogram of the percent change in average walking speed during the 12-week stable dose period (observed cases, ITT population).

Results for the primary efficacy variable (percent change in average walking speed during the 12-week stable dose period relative to baseline based on the 25-foot walk) are summarized in FIG. 3. The timed 25 foot walk showed a trend toward increased speed during the stable dose period for all three dose groups, though the average improvement declined during the treatment period, as shown in FIG. 3. The mean percent changes in average walking speed during the 12-week stable dose period (based on adjusted geometric mean change of the log-transformed walking speeds) were 2.5%, 5.5%, 8.4%, and 5.8% for the placebo, 10 mg bid, 15 mg bid, and 20 mg bid groups, respectively. There were no statistical differences between any Fampridine-SR groups and the placebo group.

Figure 4:
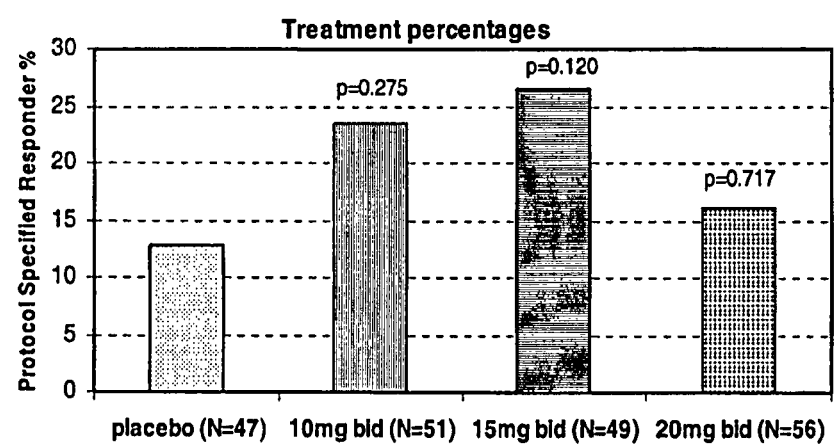
FIG. 4 is a histogram of the percentage of protocol specified responders (subjects with average changes in walking speed during the 12-week stable dose period of at least 20%) by treatment group [(observed cases, ITT population]).

Results for the protocol specified responder analysis (subjects with average changes in walking speed during the 12 weeks of stable double-blind treatment of at least 20%) are summarized in FIG. 4. The percentages of subjects with average changes in walking speed during the 12-week stable dose period of at least 20% (pre-defined responders) were 12.8%, 23.5%, 26.5%, and 16.1% for the placebo, 10 mg bid, 15 mg bid, and 20 mg bid groups, respectively. There were no statistically significant differences between any of the Fampridine-SR groups and the placebo group.

Figure 5:
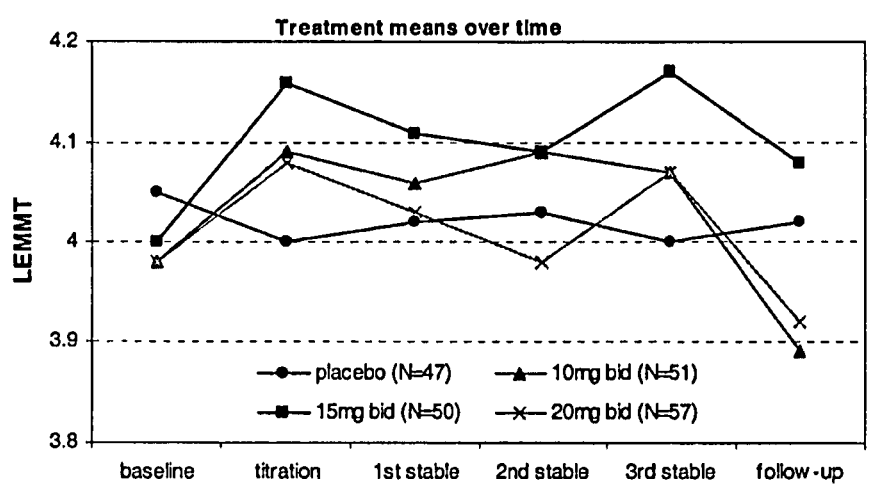
FIG. 5 is a graph of LEMMT by study day (observed cases, ITT population).

Descriptive statistics for the average overall Lower Extremity Manual Muscle Testing (LEMMT) by study day are presented in Table 8 and in FIG. 5.

TABLE 8

Average overall LEMMT by Study Day
Summary Statistics Over Time

| Treatment | | Study day | | | | | |
|---|---|---|---|---|---|---|---|
| | | base | titration | 1st stbl | 2nd stbl | 3rd stbl | follow-up |
| placebo | Mean | 4.05 | 4.00 | 4.02 | 4.03 | 4.00 | 4.02 |
| | (SD) | (0.690) | (0.705) | (0.687) | (0.696) | (0.679) | (0.738) |
| | N# | 47 | 46 | 46 | 46 | 45 | 45 |
| 10 mg bid | Mean | 3.98 | 4.09 | 4.06 | 4.09 | 4.07 | 3.89 |
| | (SD) | (0.661) | (0.641) | (0.650) | (0.685) | (0.642) | (0.631) |
| | N | 51 | 50 | 51 | 51 | 50 | 49 |
| 15 mg bid | Mean | 4.00 | 4.16 | 4.11 | 4.09 | 4.17 | 4.08 |
| | (SD) | (0.737) | (0.653) | (0.645) | (0.659) | (0.618) | (0.674) |
| | N | 50 | 49 | 49 | 49 | 49 | 46 |
| 20 mg bid | Mean | 3.98 | 4.08 | 4.03 | 3.98 | 4.07 | 3.92 |
| | (SD) | (0.634) | (0.639) | (0.659) | (0.714) | (0.649) | (0.650) |
| | N | 57 | 54 | 52 | 52 | 48 | 55 |

The treatment sample sizes presented at individual time points may be smaller than those in the ITT population due to dropouts or missed assessments.

During double-blind treatment, all the Fampridine-SR groups exhibited a numerical pattern of larger mean LEMMT scores than placebo (except the 20 mg bid group at the $2^{nd}$ stable dose visit). After double-blind medication was discontinued, with the exception of the 15 mg bid group, all the group means were lower than they were at baseline.

Figure 6:
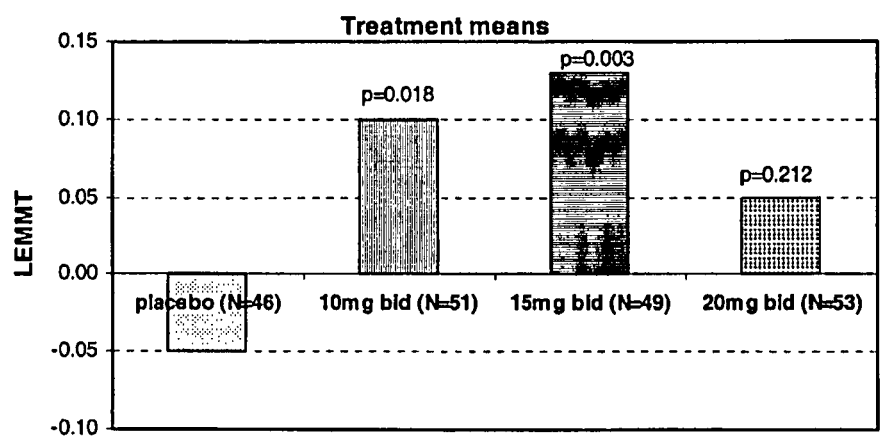
FIG. 6 is a histogram of change in LEMMT during the 12-week stable dose period (observed cases, ITT population).

Results for the average change in LEMMT during the 12-week stable dose period relative to baseline are summarized in FIG. 6. The mean changes in overall LEMMT during the 12-week stable dose period were −0.05 units, 0.10 units, 0.13 units, and 0.05 units for the placebo, 10 mg bid, 15 mg bid, and 20 mg bid groups, respectively. Improvements in LEMMT were significantly greater in the 10 mg bid and 15 mg bid groups compared to the placebo group; there was no significant difference between the 20 mg bid group and the placebo group.

No statistically significant differences were detected among treatment group based on any of the other secondary efficacy variables, as shown in Table 9.

Figure 8:
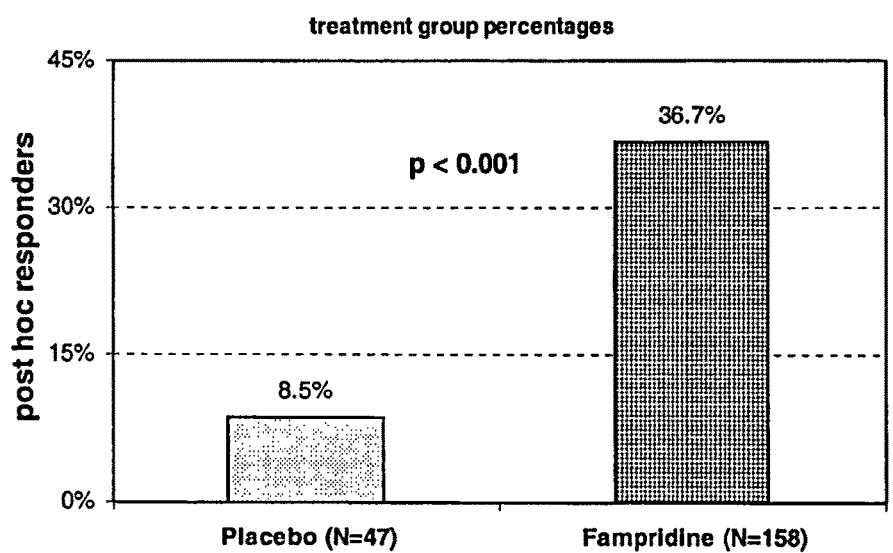
FIG. 8 is a histogram of the percentage of responders for placebo subjects vs. fampridine subjects pooled (ITT population) according to a responder analysis of the present invention.

Given that there was little difference in responsiveness between the three doses examined, more detailed analyses were performed comparing the pooled Fampridine-SR treated groups against the placebo-treated group. FIG. 8 summarizes, for the placebo and the pooled Fampridine-SR group, the percentage of post hoc responders. The number of subjects who met the post hoc responder criterion in the pooled Fampridine-SR treated group was 58 (36.7%) compared to 4 (8.5%) in the placebo-treated group, and this difference was statistically significant ($p<0.001$).

TABLE 9

Changes in secondary efficacy variables from baseline during the 12-week stable dose period

| | Treatment Group | | | |
|---|---|---|---|---|
| Parameter | placebo N = 47 | 10 mg bid N = 51 | 15 mg bid N = 50 | 20 mg bid N = 57 |
| Ashworth Score | | | | |
| N | 46 | 51 | 49 | 53 |
| Mean (SD) | −0.11 (0.377) | −0.04 (0.449) | −0.06 (0.375) | 0.02 (0.466) |
| p-value (each dose vs. placebo) | | 0.802 | 0.826 | 0.275 |
| CGI | | | | |
| N | 45 | 50 | 49 | 52 |
| Mean (SD) | 0.0 (0.66) | −0.2 (0.72) | −0.1 (0.85) | 0.0 (0.78) |
| p-value (each dose vs. placebo) | | 0.772 | 0.997 | 0.996 |
| SGI | | | | |
| N | 46 | 50 | 49 | 53 |
| Mean (SD) | −0.2 (0.96) | 0.0 (1.27) | −0.1 (1.11) | −0.1 (0.86) |
| p-value (each dose vs. placebo) | | 0.704 | 0.953 | 0.968 |
| PASAT | | | | |
| N | 46 | 51 | 49 | 53 |
| Mean (SD) | 2.17 (4.016) | 2.13 (3.394) | 0.90 (3.274) | 0.65 (4.590) |
| p-value (each dose vs. placebo) | | >0.999 | 0.306 | 0.218 |
| MSFC | | | | |
| N | 46 | 51 | 49 | 52 |
| Mean (SD) | 0.08 (0.205) | 0.10 (0.310) | 0.90 (0.224) | 0.06 (0.194) |
| p-value (each dose vs. placebo) | | 0.977 | >0.999 | 0.968 |
| MSWS-12 | | | | |
| N | 46 | 51 | 49 | 52 |
| Mean (SD) | −3.56 (14.548) | −5.53 (16.154) | −7.32 (16.295) | −5.76 (15.296) |
| p-value (each dose vs. placebo) | | 0.718 | 0.445 | 0.617 |

Note:
The treatment sample sizes presented in the treatment heading represent the number of ITT subjects. Sample sizes for individual variables may be smaller due to dropouts or missed assessments.
Note:
For each variable, the p-values (versus placebo) are Dunnett-adjusted.

While pre-planned analyses of the primary efficacy endpoint provided insufficient evidence of treatment benefits for any of the Fampridine-SR doses, subsequent analysis revealed the existence of a subset of subjects who responded to the drug with clinical meaningfulness. These subjects exhibited walking speeds while on drug that were consistently better than the fastest walking speeds measured when the subjects were not taking active drug.

Figure 7:
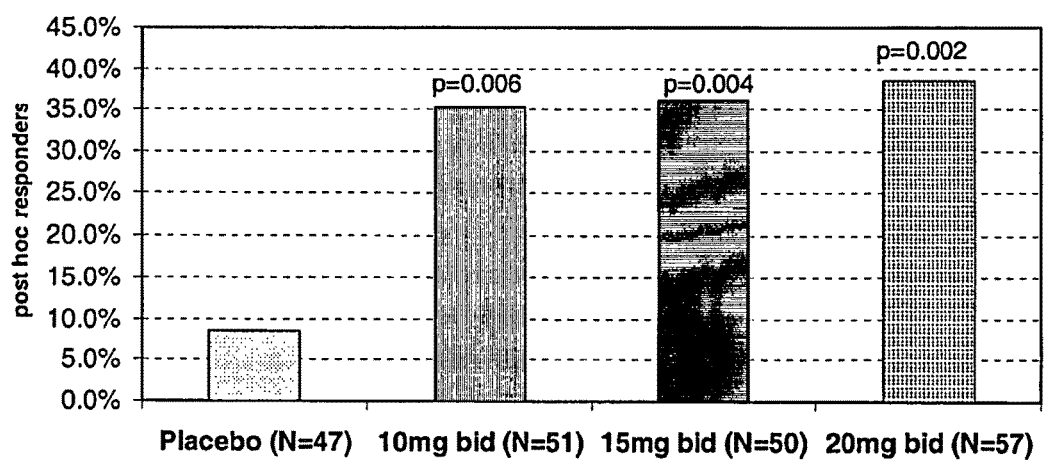
FIG. 7 is a histogram of the percentage of post hoc responders by treatment group (ITT population) according to a responder analysis of the present invention.

The post hoc responder rates based on consistency of improved walking speeds were significantly higher in all three active dose groups (35, 36 and 39%) compared to placebo (9%; $p<0.006$ for each dose group, adjusting for multiple comparisons) as shown in FIG. 7.

To validate the clinical meaningfulness of the post hoc responder variable, the 62 responders (58 fampridine and 4 placebo) were compared against the 143 non-responders (100 fampridine and 43 placebo) on the subjective variables to determine if subjects with consistently improved walking speeds during the double-blind could perceived benefit relative to those subjects who did not have consistently improved walking speeds. The results are summarized in FIG. 9 and indicate that consistency in walking speed had clinical meaningfulness for the subjects in this study since the responders had (over the double-blind period) significantly better changes from baseline in MSWS-12 and significantly better subjective global scores. In addition, the responders were rated marginally better than the non-responders by the clinicians during the double-blind. Thus, responders experienced clinically meaningful improvements in their MS symptoms, and treatment with fampridine significantly increased the chances of such a response.

To establish baseline comparability among the responder analysis groups, analyses were performed on the baseline demographic variables, key neurological characteristics and the relevant efficacy variables at baseline. In general, the responder analysis groups were comparable for all demographic and baseline characteristics variables.

Having demonstrated the clinical meaningfulness of consistently improved walking speeds during the double-blind as a criterion for responsiveness, the question of the magnitude of benefit becomes of interest. The fampridine non-responders, although providing no relevant efficacy information, do provide safety information regarding those individuals who are treated with fampridine but show no apparent clinical benefit. As such, responder analyses of these groups were performed.

Figure 10:
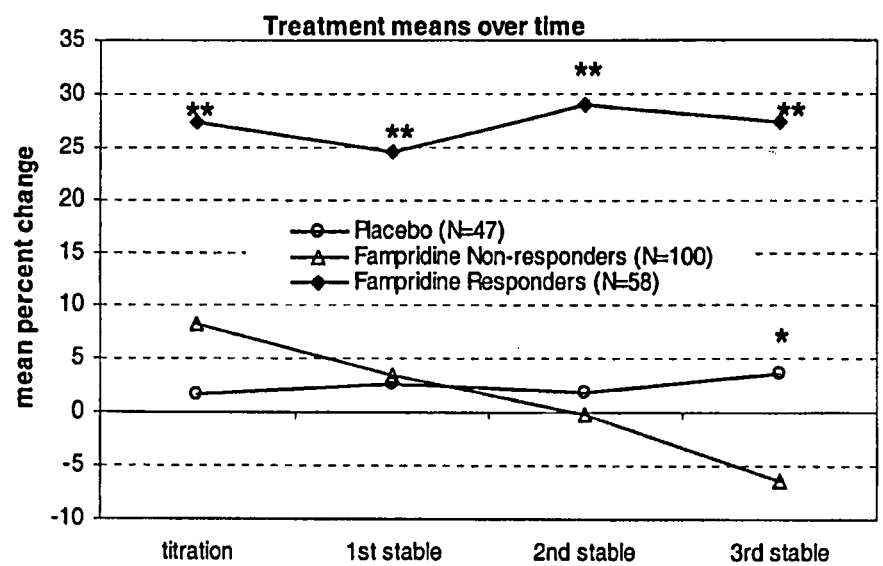
FIG. 10 is a graph of percent change in walking speed at each double-blind visit by responder analysis grouping (observed cases, ITT population).

With respect to magnitude of benefit, FIG. 10 and Table 12 below summarizes the percent changes in walking speed at each double-blind visit by responder analysis grouping. The mean improvement for the fampridine responders during the double-blind across 14 weeks of treatment ranged from 24.6% to 29.0% compared to 1.7% to 3.7% for the placebo group; this was highly significant (p<0.001) at every visit. Although providing no relevant efficacy information, results for the fampridine non-responders are also illustrated and show that there was, and could be, some worsening in walking speeds after 12-weeks when a non-responder is treated with fampridine. The improvement was stable (±3%) across 14 weeks of treatment, and was associated with improvement in two global measures (Subject Global Impression and Multiple Sclerosis Walking Scale-12). The four placebo responders showed a 19% improvement in walking speed but there were too few subjects in this group for meaningful statistical comparison. Response status was not significantly related to baseline demographics, including type or severity of MS. Adverse events and safety measures were consistent with previous experience for this drug.

TABLE 12

Summary of percent change in Walking Speed at each double-blind visit by responder analysis grouping.
Summary Statistics Over Time

| Treat- | | Study day | | | |
|---|---|---|---|---|---|
| ment | | titration | 1st stbl | 2nd stbl | 3rd stbl |
| Placebo | Mean | 1.7 | 2.6 | 1.8 | 3.7 |
| | (SEM) | (2.21) | (3.23) | (3.11) | (3.38) |
| | N# | 47 | 46 | 46 | 45 |
| Fampridine | Mean | 8.3 | 3.5 | −0.2 | −6.5 |
| Non-responders | (SEM) | (2.05) | (1.90) | (1.76) | (2.49) |
| | N | 97 | 94 | 93 | 89 |
| Fampridine | Mean | 27.4 | 24.6 | 29.0 | 27.3 |
| Responders | (SEM) | (2.43) | (2.44) | (4.31) | (3.52) |
| | N | 58 | 58 | 57 | 58 |
| FR vs. Placebo | p-value^ | <0.001 | <0.001 | <0.001 | <0.001 |
| FR vs. FNR | p-value^ | <0.001 | <0.001 | <0.001 | <0.001 |
| FNR vs. PBO | p-value^ | 0.080 | 0.884 | 0.497 | 0.022 |

ABBREVIATIONS: FR = Fampridine Responders; FNR = Fampridine Non-responders.
The treatment sample sizes presented at individual time points may be smaller than those in the ITT population due to dropouts or missed assessments.
The treatment sample sizes presented in the figure legend represent the number of ITT subjects. Sample sizes at individual time points may be smaller due to dropouts or missed assessments.
^P-values from t-tests of the least-squares means using the mean square error via an ANOVA model with effects for responder analysis grouping and center.

Figure 11:
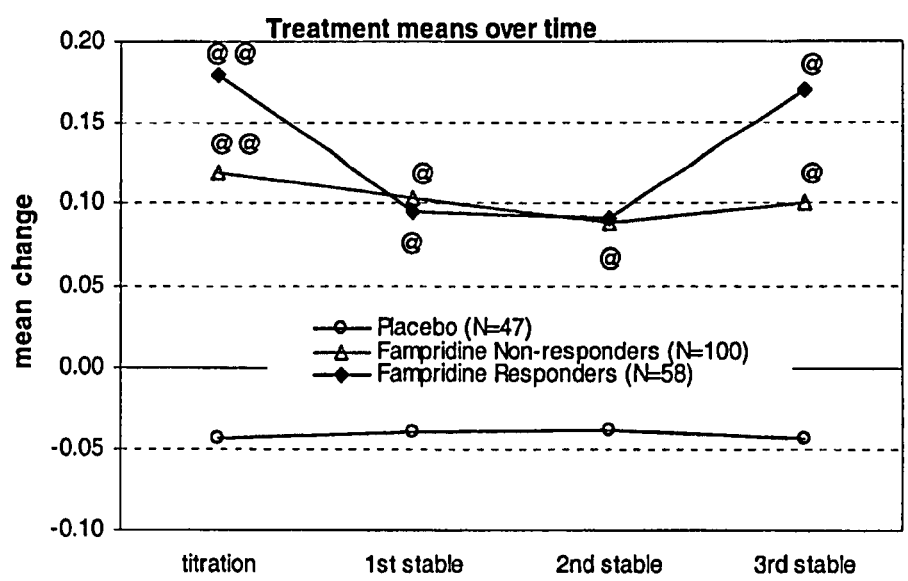
FIG. 11 is a graph of the change in LEMMT at each double-blind visit by responder analysis grouping (observed cases, ITT population).

FIG. 11 and Table 13 summarize the changes in LEMMT at each double-blind visit by responder analysis grouping. The mean improvement for the fampridine responders during the double-blind ranged from 0.09 to 0.18 units compared to −0.04 units at each visit for the placebo group; this was significant at every visit except the second stable dose visit (p=0.106). Although providing no relevant efficacy information, results for the fampridine non-responders are also illustrated and show that there was, and could be, some significant improvement in leg strength when non-responder is treated with fampridine. This suggests that although a clinically meaningful response can be linked to about 37% of subjects treated with Fampridine-SR, additional subjects may have functional improvements on variables other than walking speed.

TABLE 13

Summary of percent change in LEMMT at each double-blind visit by responder analysis grouping.
Summary Statistics Over Time

| Treat- | | Study day | | | |
|---|---|---|---|---|---|
| ment | | titration | 1st stbl | 2nd stbl | 3rd stbl |
| Placebo | Mean | −0.04 | −0.04 | −0.04 | −0.04 |
| | (SEM) | (0.035) | (0.042) | (0.039) | (0.042) |
| | N# | 46 | 46 | 46 | 45 |
| Fampridine | Mean | 0.12 | 0.10 | 0.09 | 0.10 |
| Non-responders | (SEM) | (0.028) | (0.033) | (0.036) | (0.038) |
| | N | 95 | 94 | 94 | 89 |
| Fampridine | Mean | 0.18 | 0.09 | 0.09 | 0.17 |
| Responders | (SEM) | (0.029) | (0.032) | (0.043) | (0.045) |
| | N | 58 | 58 | 58 | 58 |
| FR vs. Placebo | p-value^ | <0.001 | 0.023 | 0.106 | 0.004 |
| FR vs. FNR | p-value^ | 0.178 | 0.627 | 0.739 | 0.311 |
| FNR vs. PBO | p-value^ | <0.001 | 0.003 | 0.038 | 0.032 |

ABBREVIATIONS: FR = Fampridine Responders; FNR = Fampridine Non-responders.
The treatment sample sizes presented at individual time points may be smaller than those in the ITT population due to dropouts or missed assessments. Treatment sample sizes presented in the figure legend represent the number of ITT subjects. Sample sizes at individual time points may be smaller due to dropouts or missed assessments.
^P-values from t-tests of the least-squares means using the mean square error via an ANOVA model with effects for responder analysis grouping and center.

Figure 12:
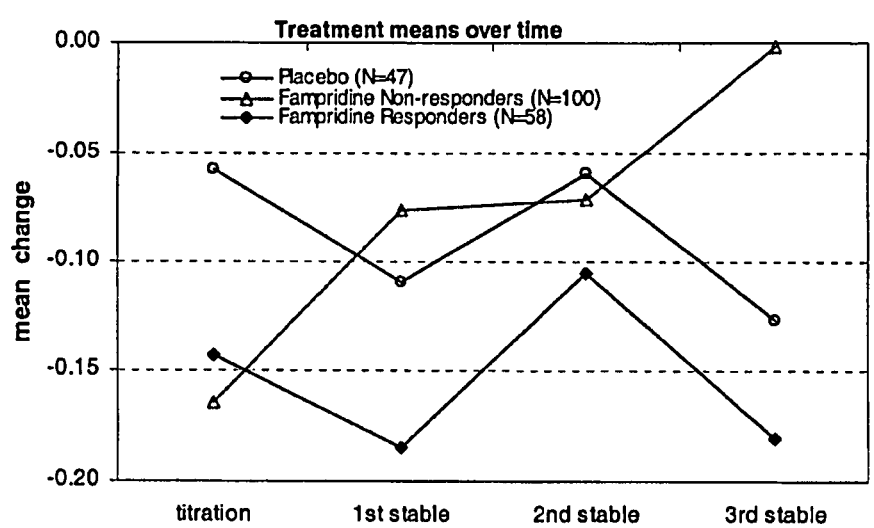
FIG. 12 is a graph of change in overall Ashworth Score at each double-blind visit by responder analysis grouping (observed cases, ITT population).

FIG. 12 and Table 14, below, summarize the changes in Overall Ashworth Score at each double-blind visit by responder analysis grouping. The mean reduction from baseline (indicative of improvement) for the fampridine responders during the double-blind ranged from −0.18 to −0.11 units compared to −0.11 to −0.06 for the placebo group. The fampridine responders were numerically superior to placebo but there was insufficient evidence to detect significant differences. Although appearing to provide little relevant efficacy information, results for the fampridine non-responders are also illustrated.

TABLE 14

Summary of change in overall Ashworth score at each double-blind visit by responder analysis grouping.
Summary Statistics Over Time

| Treat- | | Study day | | | |
|---|---|---|---|---|---|
| ment | | titration | 1st stbl | 2nd stbl | 3rd stbl |
| Placebo | Mean | −0.06 | −0.11 | −0.06 | −0.13 |
| | (SEM) | (0.069) | (0.073) | (0.070) | (0.073) |
| | N# | 46 | 46 | 46 | 45 |
| Fampridine | Mean | −0.16 | −0.08 | −0.07 | 0.00 |
| Non-responders | (SEM) | (0.044) | (0.053) | (0.054) | (0.056) |
| | N | 95 | 94 | 94 | 89 |

TABLE 14-continued

Summary of change in overall Ashworth score at each double-blind visit by responder analysis grouping.
Summary Statistics Over Time

| Treat-ment | | titration | 1st stbl | 2nd stbl | 3rd stbl |
|---|---|---|---|---|---|
| Fampridine | Mean | −0.14 | −0.18 | −0.11 | −0.18 |
| Responders | (SEM) | (0.058) | (0.066) | (0.060) | (0.055) |
| | N | 58 | 58 | 58 | 58 |
| FR vs. Placebo | p-value^ | 0.343 | 0.374 | 0.717 | 0.680 |
| FR vs. FNR | p-value^ | 0.675 | 0.210 | 0.911 | 0.064 |
| FNR vs. PBO | p-value^ | 0.151 | 0.823 | 0.772 | 0.189 |

ABBREVIATIONS: FR = Fampridine Responders; FNR = Fampridine Non-responders.
The treatment sample sizes presented at individual time points may be smaller than those in the ITT population due to dropouts or missed assessments.
^P-values from t-tests of the least-squares means using the mean square error via an ANOVA model with effects for responder analysis grouping and center.

Adverse events most commonly reported prior to treatment were accidental injury, reported by 12 (5.8%) subjects, nausea, reported by 9 (4.4%) subjects, and asthenia, diarrhea, and paresthesia, each reported by 8 (3.9%) subjects. Six (2.9%) subjects also reported headache, anxiety, dizziness, diarrhea, and peripheral edema. These adverse events are indicative of the medical conditions affecting people with MS.

Conclusions. The data does not appear to support either a number of anecdotal reports or expectations from preclinical pharmacology that doses higher than about 10 to 15 mg b.i.d., and even about 10 mg b.i.d., should be associated with greater efficacy. The data presented below in Table 15 support this, based on the new responder analysis methodology.

TABLE 15

Comparison of 10 mg vs. 15 mg among Responders

| | 10 mg (N = 51) | 15 mg (N = 50) |
|---|---|---|
| Responders N (%) | 18 (35.3) | 18 (36.0) |
| Average % CFB in Walk Speed: Mean (SD) | 27.6% (18.39) | 29.6% (22.43) |
| % Change in Walk Speed by Visit: minimum-maximum | 26%-32% | 27%-31% |
| Average SGI | 4.8 (1.09) | 4.7 (1.09) |
| Average Change in MSWS-12 * | −11.1 (21.9) | −7.8 (19.6) |

* For the average change in the MSWS-12, a negative score is indicative of subjective improvement.

A responder analysis based on consistency of improvement provides a sensitive, meaningful approach to measuring effects on the timed 25 foot walk and may be used as a primary endpoint for future trials. This data suggest that for responsive subjects (approximately 37%), treatment with fampridine at doses of 10-20 mg bid produces substantial and persistent improvement in walking.

Efficacy. There are no notable differences between 10 mg bid and 15 mg bid among subjects who respond to drug. In fact, the largest difference, favors the 10 mg bid group (see MSWS-12 result).

Safety. With respect to safety, there are three considerations: There was an apparent decline below baseline walking speed at the last visit on drug in the fampridine non-responders in the 10 mg bid and 20 mg bid groups, but not the 15 mg bid group. This may or may not be significant, but is not clearly dose related. There was an apparent rebound effect, with walking speed dropping below baseline, among fampridine treated subjects at the two week follow-up visit; this occurred in the 15 and 20 mg but not the 10 mg bid group. Serious AE's were more frequent in the 15 mg and 20 mg bid groups 10% and 12% rates vs. 0% rate in 10 mg bid and 4% in placebo groups. This may or may not be significant, but the risk of potentially related SAEs, particularly seizures appears to be dose-related from all available data and based on mechanism of action. Based on this data, it would appear that a 10 mg bid dose is preferred because of its favorable risk to benefit ratio compared with the 15 and 20 mg doses.

Although the present invention has been described in considerable detail with reference to certain preferred embodiments thereof, other versions are possible. Therefore the spirit and scope of the appended claims should not be limited to the description and the preferred versions contain within this specification.

We claim:

1. A method of improving walking in a human multiple sclerosis patient in need thereof comprising:
  (a) measuring walking performance of the patient in a test administered prior to treatment of the patient with 4-aminopyridine;
  (b) treating the patient with 4-aminopyridine over a period of time;
  (c) measuring walking performance of the patient in a plurality of tests administered during said period of time;
  (d) selecting a patient who exhibits an improved walking performance during a majority of the plurality of tests administered during said period of time as compared to the test administered prior to treatment of the patient with 4-aminopyridine; and
  (e) orally administering to said patient selected in step (d) a sustained release composition of 10 milligrams of 4-aminopyridine twice daily for a time period of at least two weeks.

2. The method of claim 1, wherein said test is a Timed 25 Foot Walk.

3. The method of claim 1, wherein said test is a 12-Item MS Walking Scale (MSWS-12).

4. The method of claim 1, wherein the time period in step (e) comprises 12 weeks.

5. The method of claim 1, wherein the treating in step (b) comprises orally administering a sustained release composition of 10 milligrams of 4-aminopyridine twice daily.

6. The method of claim 1, wherein the twice daily administering in step (e) is administering approximately every 12 hours.

7. The method of claim 1, wherein said sustained release composition provides a mean $T_{max}$ in a range of about 2 to about 5.2 hours after administration to the patient.

8. The method of claim 1, wherein said sustained release composition is a tablet.

9. A method of increasing walking speed in a human multiple sclerosis patient in need thereof comprising:
  (a) measuring walking speed of the patient in a test administered prior to treatment of the patient with 4-aminopyridine;
  (b) treating the patient with 4-aminopyridine over a period of time;
  (c) measuring walking speed of the patient in a plurality of tests administered during said period of time;
  (d) selecting a patient who exhibits an improved walking speed during a majority of the plurality of tests administered during said period of time as compared to the test administered prior to treatment of the patient with 4-aminopyridine; and (e) orally administering to said patient selected in step (d) a sustained release composition of 10 milligrams of 4-aminopyridine twice daily for a time period of at least two weeks.

10. The method of claim 9, wherein said test is a Timed 25 Foot Walk.

11. The method of claim 9, wherein the time period in step (e) comprises 12 weeks.

12. The method of claim 9, wherein the treating in step (b) comprises orally administering a sustained release composition of 10 milligrams of 4-aminopyridine twice daily.

13. The method of claim 9, wherein the twice daily administering in step (e) is administering approximately every 12 hours.

14. The method of claim 9, wherein said sustained release composition provides a mean $T_{max}$ in a range of about 2 to about 5.2 hours after administration to the patient.

15. The method of claim 9, wherein said sustained release composition is a tablet.

16. A method of improving walking in a human multiple sclerosis patient in need thereof comprising:
(a) identifying the patient as a responder to treatment with 4-aminopyridine based on consistency of improvement in walking of the patient over time rather than magnitude of the improvement in walking in response to treatment with 4-aminopyridine, by a method comprising treating the patient with 4-aminopyridine over a period of time and repeatedly testing for consistency of improvement in walking of the patient over said period of time; and
(b) orally administering to said patient identified in step (a) a sustained release composition of 10 milligrams of 4-aminopyridine twice daily for a time period of at least two weeks.

17. The method of claim 16, wherein the improvement in walking is an increase in walking speed.

18. The method of claim 16, wherein the improvement in walking is measured by MSWS-12.

19. The method of claim 16, wherein the time period in step (b) comprises 12 weeks.

20. The method of claim 16, wherein the treating in step (a) comprises orally administering a sustained release composition of 10 milligrams of 4-aminopyridine twice daily.

21. The method of claim 16, wherein the twice daily administering in step (b) is administering approximately every 12 hours.

22. The method of claim 16, wherein said sustained release composition provides a mean $T_{max}$ in a range of about 2 to about 5.2 hours after administration to the patient.

23. The method of claim 16, wherein said sustained release composition is a tablet.

24. A method of increasing walking speed in a human multiple sclerosis patient in need thereof comprising:
(a) identifying the patient as a responder to treatment with 4-aminopyridine based on consistency of improvement in walking speed of the patient over time rather than magnitude of increase in walking speed of the patient, in response to treatment with 4-aminopyridine, wherein the identifying comprises treating the patient with 4-aminopyridine over a period of time and repeatedly testing for consistency of improvement in the walking speed of the patient over said period of time, wherein said testing comprises measuring walking speed of the patient using a Timed 25 Foot Walk during said period of time; and
(b) orally administering to said patient identified in step (a) a sustained release composition of 10 milligrams of 4-aminopyridine twice daily for a time period of at least two weeks.

25. The method of claim 24, wherein the time period in step (b) comprises 12 weeks.

26. The method of claim 24, wherein the treating in step (a) comprises orally administering a sustained release composition of 10 milligrams of 4-aminopyridine twice daily.

27. The method of claim 24, wherein the twice daily administering in step (b) is administering approximately every 12 hours.

28. The method of claim 24, wherein said sustained release composition provides a mean $T_{max}$ in a range of about 2 to about 5.2 hours after administration to the patient.

29. The method of claim 24, wherein said sustained release composition is a tablet.

* * * * *